United States Patent
Jude-Fishburn et al.

(10) Patent No.: US 10,806,794 B2
(45) Date of Patent: *Oct. 20, 2020

(54) PROTEASE INHIBITORS HAVING ENHANCED FEATURES

(71) Applicant: Nektar Therapeutics, San Francisco, CA (US)

(72) Inventors: C. Simone Jude-Fishburn, Redwood City, CA (US); Laurie A. VanderVeen, San Mateo, CA (US); Timothy A. Riley, Worcester, MA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/107,689

(22) Filed: Aug. 21, 2018

(65) Prior Publication Data

US 2018/0353609 A1 Dec. 13, 2018

Related U.S. Application Data

(63) Continuation of application No. 15/228,793, filed on Aug. 4, 2016, now Pat. No. 10,092,656, which is a (Continued)

(51) Int. Cl.
*A61K 31/655* (2006.01)
*A61K 31/34* (2006.01)
(Continued)

(52) U.S. Cl.
CPC .......... *A61K 47/55* (2017.08); *A61K 31/4402* (2013.01); *A61K 31/4433* (2013.01);
(Continued)

(58) Field of Classification Search
CPC ............ A61K 31/4402; A61K 31/4709; A61K 31/4433; A61K 31/34; A61K 31/635
(Continued)

(56) References Cited

U.S. PATENT DOCUMENTS

| | | |
|---|---|---|
| 5,672,662 A | 9/1997 | Harris et al. |
| 8,598,364 B2 | 12/2013 | Riggs-Sauthier et al. |

(Continued)

FOREIGN PATENT DOCUMENTS

| | | |
|---|---|---|
| FR | 2 773 994 | 7/1999 |
| WO | WO 02/098949 | 12/2002 |

(Continued)

OTHER PUBLICATIONS

Chen et al., "Synthesis and Properties of ABA Amphiphiles", J. Org. Chem., vol. 64, pp. 6870-6873, (1999).
(Continued)

*Primary Examiner* — Shengjun Wang
(74) *Attorney, Agent, or Firm* — Jacqueline F. Mahoney

(57) ABSTRACT

Provided herein (among other things) are protease inhibitor compounds having enhanced features, along with methods for administering such compounds. For example, the subject compounds can be administered without concomitant administration of a CYP3A4 inhibitor, have increased therapeutic index and/or increased potency, and are low-resistance inducing in nature.

7 Claims, 4 Drawing Sheets

Related U.S. Application Data continuation of application No. 13/119,079, filed as application No. PCT/US2009/005208 on Sep. 17, 2009, now abandoned.

(60) Provisional application No. 61/198,934, filed on Nov. 12, 2008, provisional application No. 61/192,417, filed on Sep. 17, 2008, provisional application No. 61/192,439, filed on Sep. 17, 2008, provisional application No. 61/192,459, filed on Sep. 17, 2008.

(51) Int. Cl.
| | |
|---|---|
| A61K 47/55 | (2017.01) |
| A61K 31/4402 | (2006.01) |
| A61K 31/4433 | (2006.01) |
| A61K 31/635 | (2006.01) |
| A61K 38/05 | (2006.01) |
| A61K 47/60 | (2017.01) |

(52) U.S. Cl.
CPC .......... *A61K 31/635* (2013.01); *A61K 38/05* (2013.01); *A61K 47/60* (2017.08)

(58) Field of Classification Search
USPC ................................. 514/357, 470, 345, 318
See application file for complete search history.

(56) References Cited

U.S. PATENT DOCUMENTS

| 9,107,956 B2 | 8/2015 | Riggs-Sauthier et al. |
| 2004/0224900 A1 | 11/2004 | Bailey et al. |
| 2005/0136031 A1 | 6/2005 | Bentley et al. |
| 2011/0195940 A1 | 8/2011 | Jude-Fishburn et al. |
| 2017/0028077 A1 | 2/2017 | Jude-Fishburn et al. |

FOREIGN PATENT DOCUMENTS

| WO | WO 2005/000360 | 1/2005 | |
| WO | WO-2006108879 A2 * | 10/2006 | ........... C07D 417/12 |
| WO | WO 2008/112289 | 9/2008 | |
| WO | WO 2010/033226 | 3/2010 | |

OTHER PUBLICATIONS

Flexner, "Dual Protease Inhibitor Therapy in HIV-Infected Patients: Pharmacologic Rationale and Clinical Benefits", Annu. Rev. Pharmacol. Toxicol., vol. 40, pp. 649-674, (2000).
Gunaseelan et al., "Synthesis of Poly(ethylene gylcol)-Based Saquinavir Prodrug Conjugates and Assessment of Release and Anti-HIV-1 Bioactivity Using a Novel Protease Inhibition Assay", Bioconj. Chem., vol. 15, pp. 1322-1333, (2004).
Hammer et al., "Treatment for Adult HIV Infection", JAMA, vol. 296, No. 7, pp. 827-843, (Aug. 16, 2006).
Havlir et al., "Atazanivir: New Option for Treatment of HIV Infection," Reviews of Anti-Infective Agents, vol. 38, pp. 1599-1604, (Jun. 1 2004).
Kempf et al., "Antiviral and Pharmacokinetic Properties of C2 Symmetric Inhibitors of the Human Immunodeficiency Virus Type I Protease", Antimicrob. Agents and Chemtherp., vol. 35, No. 11, pp. 2209-2214, (Nov. 1991).
Matsumoto et al., "Design, Synthesis, and Biological Evaluation of Anti-HIV Double Drugs: Conjugates of HIV Protease Inhibitors with a Reverse Transcriptase Inhibitor through Spontaneously Cleavable Linkers", Bioorganic & Med. Chem., vol. 9.
McQuade, "A Synthetic HIV-1 Protease Inhibitor with Antiviral Activity Arrests HIV-Like Particle Maturation", Science, vol. 247, pp. 454-456, (1990).
MMWR, "The Global HIV/AIDS Pandemic, 2006", CDC Prevention, vol. 55, No. 31, pp. 841-844, (Aug. 11, 2006).
Molina et al., "Once-daily atazanivir/ritonavir versus twice-daily lopinavir/ritonavir, each in combination with tenofovir and emtricitabine, for management of antiretroviral-naïve HIV-1-infected patients: 48 week efficacy and safety results of the CASTLE study," The Lancet, vol. 372, pp. 646-655, (2008).
Moyle et al., "Principles and practice of HIV-protease inhibitor pharmacoenhancement", HIV Medicine, vol. 2, pp. 105-113, (2001).
Pauwels et al., "Rapid and automated tetrazolium-based colorimetric assay for the detection of anti-HIV compounds", J. of Virol. Meth., vol. 20, pp. 309-321, (1988).
Rathbun et al., "Low-Dose Ritonavir for Protease Inhibitor Pharmacokinetic Enhancement", Ann. Pharmacother., vol. 36, pp. 702-706, (2002).
Sanne et al., "Results of a Phase 2 Clinical Trial at 48 Weeks (AI424-007): A Dose-Ranging, Safety, and Efficacy Comparative Trial of Atazanivir at the Three Doses in Combination with Didanosine and Stavudine in Antiretroviral-Naïve Subjects", JAIDS.
Yu et al., "Dual protease inhibitor therapy in the management of the HIV-1", Exp. Opin. on Pharmacother., vol. 1, No. 7, pp. 1331-1342, (2000).
Zeldin et al., "Pharmacological and therapeutic properties of ritonavir-boosted protease inhibitor therapy in HIV-infected patients", J. of Antimicrob. Chemother., vol. 53, pp. 4-9, (2004).
PCT International Search Report and Written Opinion corresponding to PCT Application No. PCT/US2009/005208 dated Apr. 20, 2010.
PCT International Preliminary Report on Patentability corresponding to PCT Application No. PCT/US2009/005208 dated Mar. 31, 2011.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-1$^{st}$, (Jan. 2003).
NOF Corporation, PEG Derivatives, Phospholipid and Drug Delivery Materials for Pharmaceuticals, 27 pages, Catalogue 2003-2$^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).

(56) References Cited

OTHER PUBLICATIONS

Shearwater Corporation, Polyethylene Glycol and Derivatives for Biomedical Applications, 20 pages, Catalog—(Jul. 2001).

* cited by examiner

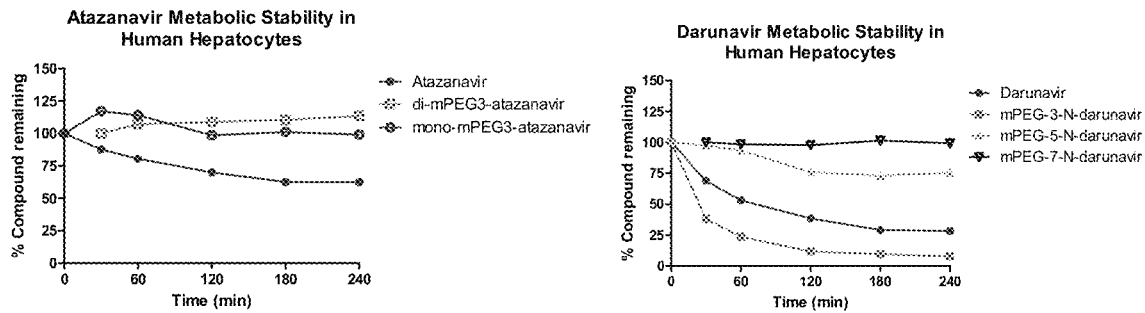
FIG. 3A
FIG. 3B
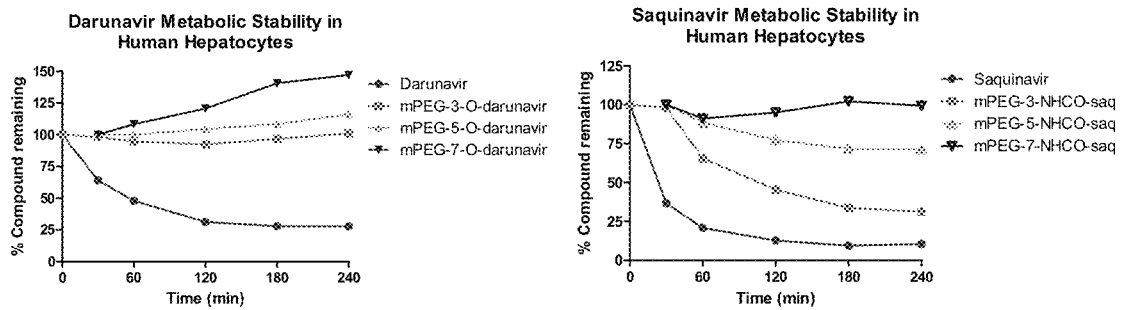
FIG. 3C
FIG. 3D
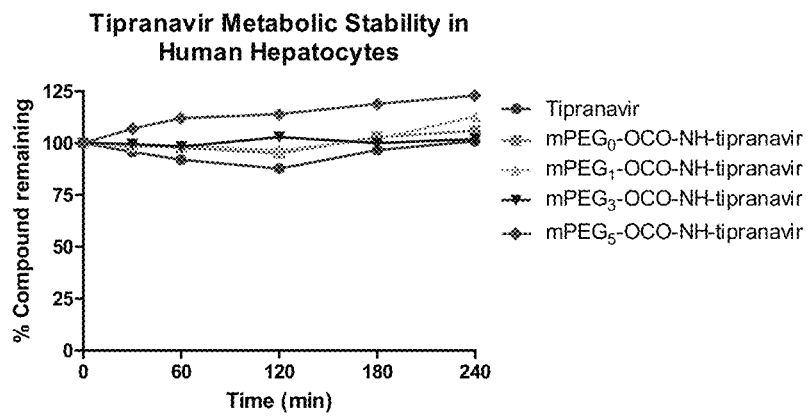
FIG. 3E

PROTEASE INHIBITORS HAVING ENHANCED FEATURES

CROSS REFERENCE TO RELATED APPLICATIONS

This application is a continuation of U.S. patent application Ser. No. 15/228,793, filed Aug. 4, 2016, now granted as U.S. Pat. No. 10,092,656, which is a continuation of U.S. patent application Ser. No. 13/119,079, filed Apr. 27, 2011, now abandoned, which is a 35 U.S.C. § 371 application of International Application No. PCT/US2009/005208, filed Sep. 17, 2009, designating the United States, which claims the benefit of priority under 35 U.S.C. § 119 (e), to U.S. Provisional Application No. 61/198,934, filed Nov. 12, 2008, U.S. Provisional Application No. 61/192,417, filed Sep. 17, 2008, U.S. Provisional Application No. 61/192,459, filed Sep. 17, 2008, and U.S. Provisional Application No. 61/192,439, filed Sep. 17, 2008, the disclosures of which are all incorporated herein by reference in their entireties.

FIELD OF THE INVENTION

This invention provides (among other things) protease inhibitor compounds having enhanced features, along with methods for administering such compounds. The subject compounds can be administered without concomitant administration of a CYP3A4 inhibitor, have increased therapeutic index and/or increased potency, and are low-resistance inducing in nature. The methods and active agents described herein relate to and/or have applications in (among others) the fields of pharmacotherapy, physiology, organic chemistry and polymer chemistry.

BACKGROUND

Since the first cases of acquired immunodeficiency syndrome (AIDS) were reported in 1981, infection with human immunodeficiency virus (HIV) has grown to pandemic proportions, resulting in an estimated 65 million infections and 25 million deaths. See Aug. 11, 2006, *MMWR* 55(31): 841-844 (Center for Disease Control and Prevention). Protease inhibitors represent an important class of compounds used to treat individuals infected with HIV, although these compounds can also treat individuals suffering from other viral infections (e.g., Hepatitis C).

With respect to HIV, protease inhibitors act to inhibit the HIV viral proteases that are necessary for the proteolytic cleavage of the gag and gag/pol fusion polypeptides necessary for the generation of infective viral particles. Thus, by inhibiting this proteolytic cleavage, protease inhibitors diminish the ability of larger HIV-fusion polypeptide precursors to generate the mature form of protein necessary for effective viral replication. McQuade et al. (1990) *Science* 247(4941):454-456.

Protease inhibitor-based therapy is acknowledged as an initial treatment for patients presenting symptomatic HIV disease and in non-symptomatic patients after the CD4 cell count is below 350/µL but before a level of 200/µL. Hammer et al. (2006) *JAMA* 296(7):827-843. In such cases, a protease inhibitor-based regimen will include a protease inhibitor (typically boosted with ritonavir) along with a combination of two nucleoside (or nucleotide) reverse transcriptase inhibitors. Id.

These conventional HIV protease inhibitors, as well as other protease inhibitors, have relatively low potency and/or relatively low (or narrow) therapeutic index.

HIV and other protease inhibitors having a relatively high potency and/or relatively high (or wide) therapeutic index would represent an improvement over conventional HIV protease inhibitors.

Moreover, although protease inhibitors serve an important role in treating patients suffering from HIV as well as hepatitis virues (e.g., hepatitis C virus), their use has been hampered by challenges associated with (among other things) limited oral bioavailability and lack of patient compliance due to the frequency of dosing and tolerability issues. Zeldin et al. (2004) *J. Antimicrob. Chemother.* 53:4-9. The lack of patient compliance, in turn, may lead to the development of resistant viral strains among patients treated with single PI regimens. Id.

In order to prevent or overcome resistance, concomitant administration with ritonavir—an inhibitor of cytochrome P-450 (CYP-450) and a protease inhibitor itself—has been used and has shown demonstrated efficacy in clinical studies. See Rathburn et al. (2002) *Ann. Pharmacother.* 36:702-706, Moyle et al. (2001) *HIV Medicine* 2:105-113, Flexner (2000) *Ann. Rev. Pharm. Tox.* 40:649-674, and Yu et al. (2000) *Expert Opin. Pharmacother.* 1:1331-1342. Interestingly, the dose of ritonavir administered in "boosted" protease inhibitor-based regimens is generally considered subtherapeutic. See Moyle et al. (2001) *HIV Medicine* 2:105-113.

Finally, sustained treatment with HIV protease inhibitors, however, has been found to lead to the generation of resistant HIV strains, which no longer respond to the protease inhibitor therapy. Such resistance is believed to be a consequence of mutations arising during viral replication that eventually lead to amino acid changes, which alter the binding interaction of the viral protease with the protease inhibitor and thus render the drug ineffective at preventing viral replication. In view of the chronic nature of HIV infection, the generation of resistant strains over the course of long-term therapy is particularly troubling.

The present disclosure seeks to address these and other needs in the art.

SUMMARY

In one or more aspects, a method is provided, the method comprising administering a HIV protease inhibitor conjugate to an individual infected with HIV, wherein the HIV protease inhibitor conjugate has an increased therapeutic index and/or increased potency. Preferably, the administering step has a dose (on a molar basis) of an HIV protease inhibitor conjugate that is both (i) different than (and preferably lower than) the corresponding HIV protease inhibitor in unconjugated form, and (ii) retains at least the same (or substantially the same) HIV protease inhibitor activity on a molar basis in a suitable model or patient.

In one or more embodiments, the administering step has a dose (on a molar basis) of an HIV protease inhibitor conjugate that provides greater HIV protease inhibitor activity on a molar basis in a suitable model or patient than the same dose (on a molar basis) of the corresponding HIV protease inhibitor in unconjugated form.

In yet another aspect, provided is a method comprising increasing the potency of a small drug molecule such as an HIV protease inhibitor by covalently attaching a water-soluble oligomer to the small drug molecule.

In one or more aspects, a compound is provided, the compound comprising a small drug molecule covalently attached to a water-soluble oligomer, wherein the potency of the small drug molecule covalently attached to the water-soluble oligomer has a greater potency than the small drug molecule in unconjugated form.

In yet a further aspect, a method is provided, the method comprising administering a potent protease inhibitor (e.g., an HIV protease inhibitor or a hepatitis virus protease inhibitor such as a HCV protease inhibitor) therapy to an individual infected with a virus, wherein said potent protease inhibitor therapy does not include co-administration of a CYP3A4 inhibitor.

In one or more related embodiments, the potent protease inhibitor is administered in a CYP3A4-competent biological system.

In one or more additional aspects, a method is provided, the method comprising administering an HIV protease inhibitor conjugate as a protease inhibitor monotherapy to a biological system infected with HIV, wherein: (i) in a biological model in which the HIV protease inhibitor conjugate is periodically added in a given molar amount over time, and in the same biological model in which a corresponding HIV protease inhibitor in unconjugated form is periodically added over time in the same given molar amount, the biological model in which the corresponding HIV protease inhibitor in unconjugated form is added is more likely to exihibit HIV protease resistance, and (ii) the HIV protease inhibitor conjugate retains at least the same (or substantially the same) HIV protease inhibitor activity on a molar basis in a suitable model or patient.

These and other objects, aspects, embodiments and features of the invention will become more fully apparent when read in conjunction with the following detailed description.

BRIEF DESCRIPTION OF THE DRAWINGS

FIG. 1A (Saquinavir, SQV); FIG. 1B (mPEG7-NHCO-Saquinavir); FIG. 1C (Nevirapine); FIG. 1D (Ritonavir); FIG. 1E (Chicago Sky Blue).

FIG. 2A (Atazanavir, di-$mPEG_{3,5,7}$-atazanavir); FIG. 2B (Darunavir, $mPEG_{3,5,7}$-N-darunavir); FIG. 2C (Tipranavir, $mPEG_{3,5,7}$-amide-tipranavir); FIG. 2D (Saquinavir, $PEG_{3,5,7}$N-Saquinavir).

FIGS. 3A-3E are graphs showing the stability of $PEG_{oglio}$-protease inhibitor conjugates and protease inhibitor molecules expressed as values (percent compound remaining) normalized to the 30 minute timepoint. FIG. 3A (Atazanuvir, di-mPEG3-atazanavir, mono-mPEG3-atazanavir); FIG. 3B (Darunavir, mPEG-3-N-darunavir, mPEG-5-N-darunavir, mPEG7-0-darunavir); FIG. 3C (Darunavir, mPEG-3-O-darunavir, mPEG-5-O-darunavir, mPEG-7-O-darunavir; FIG. 3D (Saquinavir, mPEG3-NHCO-saquinavir, mPEG5-NHCO-saquinavir, mPEG7-NHCO-saquinavir); and FIG. 3E (Tipranavir, mPEG0-OCO—NH-tipranavir, mPEG1-OCO—NH-tipranavir, mPEG3-OCO—NH-tipranavir, and mPEG5-OCO—NH-tipranavir) as further described in Example 2. Values obtained using 1 µM test compound concentration.

FIG. 4B (CYP2D6 Bactosome Stability, Atazanavir, di-mPEG3-atazanavir); FIG. 4C (CYP3A4 Bactosome Stability, Darunavir, mPEG-3-N-darunavir, mPEG-5-N-darunavir, mPEG7-O-darunavir); FIG. 4D (CYP2D6 Bactosome Stability, Darunavir, mPEG-3-N-darunavir, mPEG-5-N-darunavir, mPEG7-O-darunavir), FIG. 4E (CYP3A4 Bactosome Stability, Saquinavir, mPEG3-NHCO-saquinavir, mPEG5-NHCO-saquinavir, mPEG7-NHCO-saquinavir); and FIG. 4F (CYP2D6 Bactosome Stability, Saquinavir, mPEG3-NHCO-saquinavir, mPEG5-NHCO-saquinavir, mPEG7-NHCO-saquinavir).

DETAILED DESCRIPTION

Figure 1A:
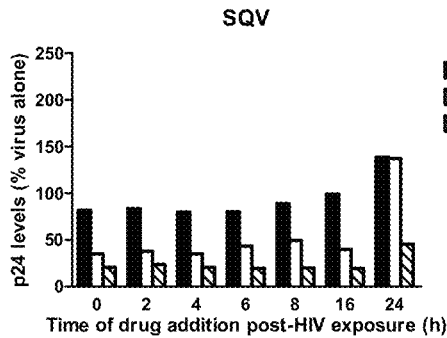
FIGS. 1A-1E provide five graphs showing p24 levels in response to PI (protease inhibitor) and $PEG_{oglio}$-PI addition at various times after high MOI HIV-1 infection, as further described in Example 1. CEM-SS cells were infected with HIV-1 for one hour, and then washed free from excess virus. Test compounds were added at various times after infection, and p24 levels were measured by ELISA at 30 hours post-infection. Values are derived from a single experiment performed in triplicate.

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

An "oligomer" is a molecule possessing from about 2 to about 50 monomers, preferably from about 2 to about 30 monomers. The architecture of an oligomer can vary. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" (also called an oligoethylene glycol) is one in which substantially all (and more preferably all) monomeric subunits are ethylene oxide subunits. The oligomer may, however, contain distinct end capping moieties or functional groups, e.g., for conjugation. Typically, PEG oligomers for use in the present invention will comprise one of the two following structures: "—$(CH_2CH_2O)_n$—" or "—$(CH_2CH_2O)_{n-1}CH_2CH_2$—," depending upon whether the terminal oxygen(s) has been displaced, e.g., during a synthetic transformation. For PEG oligomers, "n" varies from about 2 to 50, preferably from about 2 to about 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

A "reduced rate of metabolism" in reference to the present invention, refers to a measurable reduction in the rate of metabolism of a water-soluble oligomer-small molecule drug conjugate as compared to rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and must pass through the liver prior to reaching the systemic circulation. Because the liver is the primary site of drug metabolism or biotransformation, a substantial amount of drug can be metabolized before it ever reaches the systemic circulation. The degree of first pass metabolism, and thus, any reduction thereof, can be measured by a number of different approaches. For instance, animal blood samples can be collected at timed intervals and the plasma or serum analyzed by liquid chromatography/mass spectrometry for metabolite levels. Other techniques for measuring a "reduced rate of metabolism" associated with the first pass metabolism and other metabolic processes are known in the art, described herein and/or in the relevant literature, and/or can be determined by one of ordinary skill in the art. Preferably, a conjugate of the invention can provide a reduced rate of metabolism reduction satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally of greater than 25%, and preferably greater than 70%, where a compound's bioavailability is the fraction of administered drug that reaches the systemic circulation in unmetabolized form.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, carboxy, acyl, cyano. The substituted alkyl groups may be substituted once, twice or three times with the same or with different substituents.

"Lower alkyl" refers to an alkyl group containing from 1 to 6 carbon atoms, and may be straight chain or branched, as exemplified by methyl, ethyl, n-butyl, i-butyl, t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Pharmaceutically acceptable excipient" or "pharmaceutically acceptable carrier" refers to component that can be included in the compositions of the invention in order to provide for a composition that has an advantage (e.g., more suited for administration to a patient) over a composition lacking the component and that is recognized as not causing significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

An "aromatic-containing moiety" is a collection of atoms containing at least aryl and optionally one or more atoms. Suitable aromatic-containing moieties are described herein.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g., $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S).

"Pharmacologically effective amount," "physiologically effective amount," and "therapeutically effective amount" are used interchangeably herein to mean the amount of a water-soluble oligomer-small molecule drug conjugate present in a composition that is needed to provide a threshold level of active agent and/or conjugate in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

The term "biological system" is a collection of living cells and includes both a collection of living cells as well as living organisms. With respect to living organisms, the biological system includes mammalian individuals such as a patient, which refers to a living organism suffering from or prone to a condition that can be prevented or treated following the methods described herein.

"Optional" or "optionally" means that the subsequently described circumstance may but need not necessarily occur, so that the description includes instances where the circumstance occurs and instances where it does not.

Overview

As indicated above, the present disclosure is directed to the unexpected advantages and features of the subject protease inhibitor conjugates, and methods related thereto.

In a first aspect, the disclosure is directed to (among other things) a method comprising administering an HIV protease inhibitor conjugate to an individual infected with HIV, wherein the potent HIV protease has an increased therapeutic index and/or increased potency. Preferably, the administering step has a dose (on a molar basis) of an HIV protease inhibitor conjugate that: (a) is both (i) different than (and preferably lower than) the corresponding HIV protease inhibitor in unconjugated form, and (ii) retains at least the same (or substantially the same) HIV protease inhibitor activity on a molar basis in a suitable model or patient; and/or (b) provides greater HIV protease inhibitor activity on a molar basis in a suitable model or patient than the same dose (on a molar basis) of the corresponding HIV protease inhibitor in unconjugated form.

HIV proteases such as atazanavir may have an amphiphilic pocket close to the protease binding site. Current protease inhibitors bind to the binding site in a manner that does not engage the amphiphilic pocket specifically. Without wishing to be found by theory, conjugation of a flexible water-soluble oligomer to the protease inhibitor enables (relevant bonding patterns that lead to) higher affinity interaction between the protease inhibitor and the HIV protease. This is believed to lead to higher potency.

Further, toxicity effects mediated through interaction with other targets are not significantly altered. As such, the therapeutic index, defined as the ratio of toxic EC50 (TC50) to efficacious EC50, is thus increased. Examples of such HIV protease inhibitor conjugates include conjugates of atazanavir, darunavir and tipranavir, wherein such conjugates, as well as methods for their synthesis, are described herein and in PCT/US2008/003354 (WO2008/112289).

In accordance with one or more of the methods described herein, the potent HIV protease inhibitor must be administered. Any route suited for delivery of the potent HIV protease inhibitor to the biological system (e.g., individual) can be used. If, for example, the biological system is a cell culture, administration can simply involve adding, via a pipette or dropper (for example), an aliquot of liquid containing the potent HIV protease inhibitor. To the extent that the biological system is an individual infected with HIV, administering the potent HIV protease inhibitor can take place via oral administration, but other modes of administration are also contemplated, such as pulmonary, nasal, buccal, rectal, sublingual, transdermal, and parenteral.

In a second aspect, the present disclosure is directed to (among other things) a method comprising administering a potent protease inhibitor therapy to an individual infected with, wherein said potent protease inhibitor therapy does not include co-administration of a CYP3A4 inhibitor.

With respect to an HIV protease inhibitor, an active agent is an HIV protease inhibitor if it has inhibitory activity against the HIV viral proteases that are necessary for the proteolytic cleavage of the gag and gag/pol fusion polypeptides necessary for the generation of infective viral particles. Several active agents that act by this mechanism have been approved; such compounds include saquinavir, ritonavir, indinavir, amprenavir, lopinavir, atazanavir, fosamprenavir, tipranavir and darunavir. Assays known to those of ordinary skill in the art can be used to determine whether any given active agent is an HIV protease inhibitor (e.g., an HIV-1 protease inhibitor).

With regard to one or more embodiments, however, the protease inhibitor is not simply a conventional protease inhibitor. Rather, the protease inhibitor must qualify as a potent protease inhibitor, when indicated as such herein, such that concomitant administration with a CYP3A4 inhibitor is not required to effect protease inhibition in the biological system of interest.

As an initial matter, a potent HIV protease inhibitor acts via the same pharmacologic mechanism as known HIV protease inhibitors. Thus, while a potent HIV protease inhibitor shares the same mechanism of action as saquinavir, ritonavir, indinavir, amprenavir, lopinavir, atazanavir, fosamprenavir, tipranavir and darunavir, the potent HIV inhibitor for use in this particular aspect of the invention is generally not selected from the group consisting of saquinavir, ritonavir, indinavir, amprenavir, lopinavir, atazanavir, fosamprenavir, tipranavir and darunavir. Similarly, a potent hepatitis virus protease inhibitor (such as a HCV protease inhibitor) acts via the same pharmacologic mechanism as known hepatitis virus protease inhibitors. Thus, for example, while a potent HCV protease inhibitor shares the same mechanism of action as NS3 protease inhibitors (e.g., telaprevir, boceprevir and ITMN-191), the potent HIV inhibitor for use in the subject aspect of the present invention is generally not selected from the group consisting of telaprevir, boceprevir and ITMN-191.

A potent protease inhibitor (e.g., a potent HIV protease inhibitor or a potent hepatitis virus protease inhibitor such as a potent HCV protease inhibitor), however, is a protease inhibitor that remains substantially unchanged in (or is stable throughout) a four-hour in vitro hepatocyte stability assay. It is preferred that the potent protease inhibitor not only remains substantially unchanged in (or is stable throughout) a four-hour in vitro hepatocyte stability assay, but also (at equilibrium) substantially exists (that is, greater than 50% by weight exists) outside the hepatocyte cytoplasm. In the instances where a potent protease inhibitor does (at equilibrium) substantially exist inside the hepatocyte cytoplasm, the potent protease inhibitor is not substantially metabolized by cytochrome P450 3A4. While not wishing to be bound by theory, it is believed that an active agent having protease inhibitor activity is potent if it avoids degradation via cytochrome P450 3A4 enzyme-containing hepatocytes. Avoidance of degradation by cytochrome P450 3A4 enzyme-containing hepatocytes can occur following administration by, for example, the protease inhibitor localizing (at equilibrium) outside cytochrome P450 3A4 enzyme-containing cytoplasm of hepatocytes, or, if the protease inhibitor does substantially penetrate into the cytochrome P450 3A4 enzyme-containing cytoplasm of hepatocytes, the protease inhibitor is not substantially metabolized by the cytochrome P450 3A4 enzyme.

A protease inhibitor remains unchanged (or is stable) when the number and type of atoms and type of bond between those atoms making up the protease inhibitor at the beginning of the four-hour in vitro hepatocyte stability assay are the same at the end of the four hour in vitro hepatocyte stability assay. With respect to being "substantially unchanged," (or "stable") it is possible to determine whether an protease inhibitor is substantially unchanged (or stable) by performing the following test. First, it is necessary to perform the following calculation: {[(amount of the unchanged amount of the protease inhibitor following the four hour in vitro hepatocyte stability assay) subtracted from (amount of the beginning amount of the protease inhibitor introduced to the four hour in vitro hepatocyte stability assay)] divided by (amount of the beginning amount of the protease inhibitor introduced to the four-hour in vitro hepatocyte stability assay)} multiplied by 100 to provide a % value. If the % value result falls within one or more of the following ranges, then the protease inhibitor is "substantially unchanged" (or stable) and is a potent protease inhibitor (e.g., a potent HIV protease inhibitor or a potent hepatitis virus protease inhibitor such as a potent HCV protease inhibitor): less than 25% of the beginning amount is changed; less than 20% of the beginning amount is changed; less than 15% of the beginning amount is changed; less than 10% of the beginning is changed; less than 8% of the beginning amount is changed; less than 6% of the beginning amount is changed; less than 5% of the beginning amount is changed; less than 4% of the beginning amount is changed; less than 3% of the beginning amount is changed; less than 2% of the beginning amount is changed; and less than 1% of the beginning amount is changed. In some circumstances, there may be no detectable change.

In yet a further aspect, provided herein (among other things) is a method comprising administering an HIV protease inhibitor conjugate as a protease inhibitor monotherapy to a biological system infected with HIV, wherein in a biological model in which the HIV protease inhibitor conjugate is periodically added in a given molar amount over time, and in the same biological model in which a corresponding HIV protease inhibitor in unconjugated form is periodically added over time in the same given molar amount, (i) the biological model in which the corresponding HIV protease inhibitor is in unconjugated form is more likely to exihibit HIV protease resistance, and (ii) the conjugate retains at least the same (or substantially the same) HIV protease inhibitor activity on a molar basis in a suitable model or patient.

Protease Inhibitor Conjugates

Examples of HIV protease inhibitor conjugates include conjugates of atazanavir, darunavir and tipranavir, wherein such conjugates, as well as methods for their synthesis, are described herein and in PCT/US2008/003354. Examples of HIV protease inhibitor conjugates believed to be useful in one or more of the methods described herein are herein referred to as "potent HIV protease inhibitor."

In one or more embodiments, structures of HIV protease inhibitors are provided. These structures are preferably, although not necessarily, potent protease inhibitors. Exemplary HIV protease inhibitors include those of the following formula:

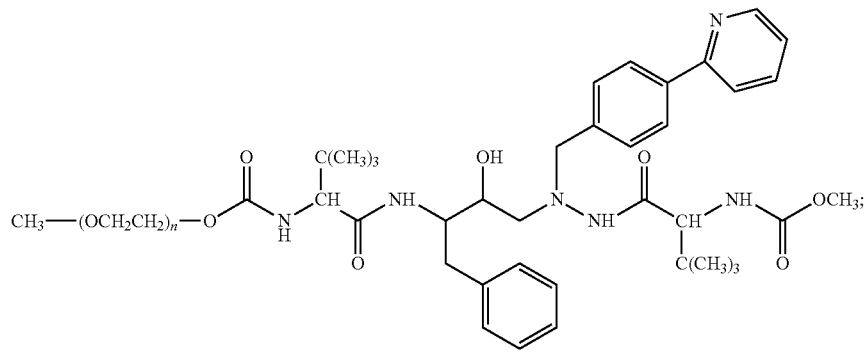

Mono-mPEGn-Atazanavir (n = 1, 3, 5, 6, 7)

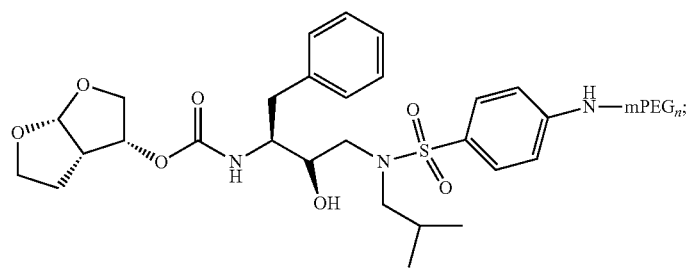

mPEGn-N-Darunavir
[wherein mPEG is ──(CH$_2$CH$_2$O)$_n$──CH$_3$ and n = 3, 5, 7]

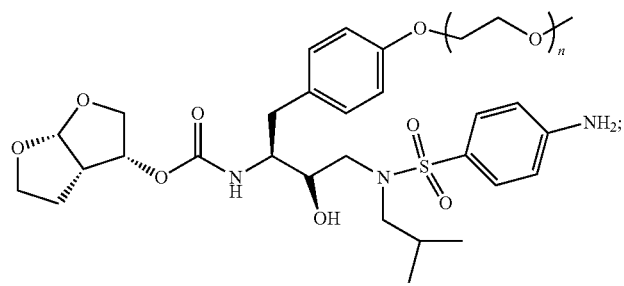

mPEGn-O-Darunavir (wherein n = 3, 5, 7)

-continued

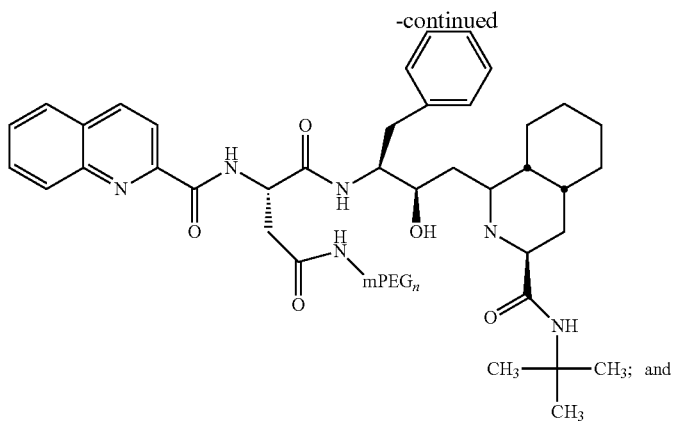

mPEGn-NHCO-Saquinavir
[wherein each mPEGn is ——(CH$_2$CH$_2$O)$_n$—CH$_3$ and n = 5 or 7]

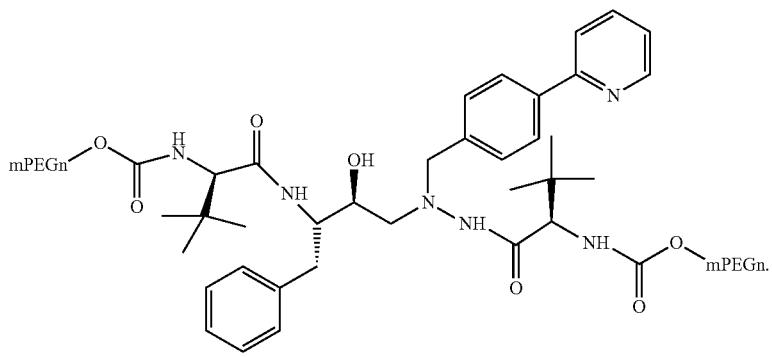

Di-mPEG3-Atazanavir
[wherein each mPEGn is ——(CH$_2$CH$_2$O)$_n$—CH$_3$ and n = 3]

Although the foregoing HIV protease inhibitors are nonlimiting examples of potent HIV protease inhibitors, any HIV protease inhibitor that qualifies as a "potent HIV protease inhibitor" can be used in one or more embodiments of the invention.

Exemplary potent HIV protease inhibitors are mono-mPEG3-atazanavir, mPEGn-N-darunavir (wherein n is 5 or 7), mPEGn-O-darunavir (wherein n is 3 or 5), mPEGn-NHCO-saquinavir (wherein n is 5 or 7), and di-mPEG3-atazanavir. Preferred potent HIV protease inhibitors include mono-mPEG3-atazanavir, mPEGn-N-darunavir (wherein n is 5 or 7), mPEGn-O-darunavir (wherein n is 3 or 5). Such potent HIV protease inhibitors, as well as methods for their synthesis, are described herein and in PCT/US2008/003354.

Candidates that may qualify as a potent HCV protease inhibitor in accordance with the definitions provided herein are described in U.S. provisional application entitled "Oligomer-Protease Inhibitor Conjugates," filed on Sep. 17, 2008 (Applicant's reference number: SHE0216.PRO) and assigned U.S. Provisional Patent Application No. 61/192,438.

Protease Inhibitors

An HIV protease inhibitor will generally have a molecular weight of less than 1000 Da. Exemplary molecular weights include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

An HIV protease inhibitor, if chiral, may be in a racemic mixture, or an optically active form, for example, a single optically active enantiomer, or any combination or ratio of enantiomers (i.e., scalemic mixture). In addition, the potent HIV protease inhibitor may possess one or more geometric isomers. With respect to geometric isomers, a composition can comprise a single geometric isomer or a mixture of two or more geometric isomers. A potent HIV protease inhibitor for use in the present invention can be in its customary active form, or may possess some degree of modification. For example, a potent HIV protease inhibitor may have a targeting agent, tag, or transporter attached thereto, prior to or after covalent attachment of an oligomer. Alternatively, the potent HIV protease inhibitor may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the potent HIV protease inhibitor does not include attachment to a lipophilic moiety.

Water Soluble Oligomer

The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric). Preferably, each oligomer is a co-oligomer of two monomers or, more preferably, is a homo-oligomer.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

A water-soluble, non-peptidic oligomer (e.g., "POLY" in the conjugate formula

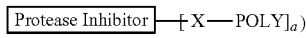

as described herein can have any of a number of different geometries. For example, the water-soluble, non-peptidic oligomer can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500 Daltons; below about 1450 Daltons; below about 1400 Daltons; below about 1350 Daltons; below about 1300 Daltons; below about 1250 Daltons; below about 1200 Daltons; below about 1150 Daltons; below about 1100 Daltons; below about 1050 Daltons; below about 1000 Daltons; below about 950 Daltons; below about 900 Daltons; below about 850 Daltons; below about 800 Daltons; below about 750 Daltons; below about 700 Daltons; below about 650 Daltons; below about 600 Daltons; below about 550 Daltons; below about 500 Daltons; below about 450 Daltons; below about 400 Daltons; below about 350 Daltons; below about 300 Daltons; below about 250 Daltons; below about 200 Daltons; below about 150 Daltons; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to about 1000 Daltons; and from about 75 to about 750 Daltons.

Preferably, the number of monomers in the water-soluble, non-peptidic oligomer falls within one or more of the following ranges (end points for each range provided are inclusive): between about 1 and about 30; between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers in series. In yet further embodiments, the oligomer (and the corresponding conjugate) possesses 21, 22, 23, 24, 25, 26, 27, 28, 29 or 30 monomers in series. Thus, for example, when the water-soluble, non-peptidic polymer includes $CH_3$—$(OCH_2CH_2)_n$—, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the small molecule protease inhibitor (in contrast to the step-wise addition of one or more monomers to effectively "grow" the oligomer onto the small molecule protease inhibitor), it is preferred that the composition containing an activated form of the water-soluble, non-peptidic oligomer be monodispersed. In those instances, however, where a bimodal composition is employed, the composition will possess a bimodal distribution centering around any two of the above numbers of monomers. Ideally, the polydispersity index of each peak in the bimodal distribution, Mw/Mn, is 1.01 or less, and even more preferably, is 1.001 or less, and even more preferably is 1.0005 or less. Most preferably, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication 2005/0136031.

Linker

The linker or linkage (through which the water-soluble, non-peptidic polymer is attached) at least includes a covalent bond, and often includes one or more atoms such as an oxygen, two atoms, or a number of atoms. A linker is typically but is not necessarily linear in nature. The linkage, "X"

(in [Protease Inhibitor]—[X—POLY]$_a$), is a stable linkage, and is preferably also enzymatically stable. Preferably, the linkage "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the linker "X" comprises an ether, amide, urethane, amine, thioether, urea, or a carbon-carbon bond. Functional groups such as those discussed below, and illustrated in the examples, are typically used for forming the linkages. The linkage may less preferably also comprise (or be adjacent to or flanked by) spacer groups. Spacers are most useful in instances where the bioactivity of the conjugate is significantly reduced due to the positioning of the oligomer relatively close to the residue of the small molecule drug, wherein a spacer can serve to increase the distance between oligomer and the residue of the small molecule drug.

More specifically, in selected embodiments, a spacer moiety, X, may be any of the following: "—" (i.e., a covalent bond, that may be stable or degradable, between the residue of the small molecule protease inhibitor and the water-soluble, non-peptidic oligomer), —C(O)O—, —OC(O)—, —CH$_2$—C(O)O—, —CH$_2$—OC(O)—, —C(O)O—CH$_2$—, —OC(O)—CH$_2$—, —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—NH—CH$_2$—CH$_2$—CH$_2$—CH$_2$—CH$_2$—, —CH$_2$—C(O)—NH—CH$_2$—CH$_2$—CH$_2$—CH$_2$—, —CH$_2$—CH$_2$—C(O)—NH—CH$_2$—CH$_2$—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—CH$_2$—, —CH$_2$—CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

For purposes of the present invention, however, a group of atoms is not considered a spacer moiety when it is immediately adjacent to an oligomer segment, and the group of atoms is the same as a monomer of the oligomer such that the group would represent a mere extension of the oligomer chain.

Conjugation

The linkage "X" connecting the water-soluble, non-peptidic oligomer within the conjugate is typically formed by reaction of a functional group on a terminus of the oligomer (or one or more monomers when it is desired to "grow" the oligomer onto the protease inhibitor) with a corresponding functional group within the protease inhibitor. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4. In addition, the carbon atom alpha to the —C(O)H moiety can optionally be substituted with alkyl.

Typically, the terminus of the water-soluble, non-peptidic oligomer not bearing a functional group is capped to render it unreactive. When the oligomer does include a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NETS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(═O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N═C═O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e. aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the protease inhibitor may not have a functional group suited for conjugation. In this instance, it is possible to modify the "original" protease inhibitor so that it does have the desired functional group. For example, if the protease inhibitor has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule protease inhibitor bearing a carboxyl group wherein the carboxyl group-bearing small molecule protease inhibitor is coupled to an amino-terminated oligomeric ethylene glycol, to provide a conjugate having an amide group covalently linking the small molecule protease inhibitor agonist to the oligomer. This can be performed, for example, by combining the carboxyl group-bearing small molecule protease inhibitor with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule protease inhibitor bearing a hydroxyl group wherein the hydroxyl group-bearing small molecule protease inhibitor is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

In another example, it is possible to prepare a conjugate of a small molecule protease inhibitor bearing a ketone group by first reducing the ketone group to form the corresponding hydroxyl group. Thereafter, the small molecule protease inhibitor now bearing a hydroxyl group can be coupled as described herein.

In still another instance, it is possible to prepare a conjugate of a small molecule protease inhibitor bearing an amine group. In one approach, the amine group-bearing small molecule protease inhibitor and an aldehyde-bearing oligomer are dissolved in a suitable buffer after which a suitable reducing agent (e.g., NaCNBH$_3$) is added. Following reduction, the result is an amine linkage formed between the amine group of the amine group-containing small molecule protease inhibitor and the carbonyl carbon of the aldehyde-bearing oligomer.

In another approach for preparing a conjugate of a small molecule protease inhibitor bearing an amine group, a carboxylic acid-bearing oligomer and the amine group-bearing small molecule protease inhibitor are combined, typically in the presence of a coupling reagent (e.g., DCC). The result is an amide linkage formed between the amine group of the amine group-containing small molecule protease inhibitor and the carbonyl of the carboxylic acid-bearing oligomer.

Exemplary conjugates of small molecule protease inhibitors (which may be "potent" or not) which can still have usefulness as having anti-HIV activity include:

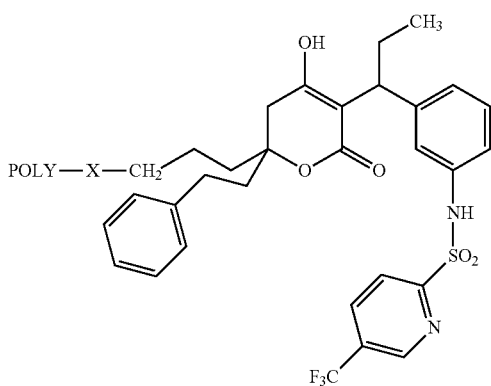

wherein, X is a spacer moiety and POLY is a water-soluble oligomer. Approaches for preparing the above compound are described in the Examples.

Assays for HIV Activity

To determine whether the small molecule protease inhibitor or the conjugate of a small molecule protease inhibitor and a water-soluble non-peptidic polymer has anti-HIV activity, it is possible to test such compounds. Anti-HIV activity can be tested as described in the Experimental. In addition, Anti-HIV activity can be tested in a human T-cell line by, for example, the method disclosed in Kempf et al. (1991) *Antimicrob. Agents Chemother.* 35(11):2209-2214, HIV-1$_{3B}$ stock ($10^{4.7}$ 50% tissue culture infection doses per ml) can be diluted 100-fold and incubated with MT-4 cells at $4 \times 10^5$ cells per ml for one hour at 37° C. (multiplicity of infection, 0.001 50% tissue culture infective dose per cell). The resulting culture is then washed twice, resuspended to $10^5$ cells per ml of medium, seeded in a volume of 1% dimethyl sulfoxide solution of compound in a series of half-log-unit dilutions in medium in triplicate. The virus control culture can be treated in an identical manner, except that no compound is added to the medium. The cell control is incubated in the absence of compound or virus. Optical density (OD) is then measured at day 5 by using 3-(4,5-dimethylthiazol-2-yl)-2,5-diphenyltetrazolium bromide (MTT) in a colorimetric assay. See Pauwels et al. (1988) *J Virol Methods* 20:309-321. Virus and control OD values are averaged over six determinations. Percent inhibition of HIV cytopathic effect (CPE) is calculated by the following formula: [(average OD−virus control OD/(cell control OD−virus control OD)]×100. Cytotoxicity is determined by the incubation in duplicate with serial dilutions of compound in the absence of virus. Percent cytotoxicity is determined according to the following formula: (average OD/cell control OD)×100. The EC$_{50}$ represents the concentration of compound that gave 50% inhibition of the cytopathic effect. The CCIC$_{50}$ is the concentration of compound which gives a 50% cytotoxic effect. It is noted that when conjugation of the water-soluble, non-peptidic oligomer occurs at the hydroxyl group located at 26 position of saquinavir, no anti-HIV activity is measured. See Table 1. While not wishing to be bound by theory, it appears that the availability of this hydroxyl group is required for activity (a "binding hydroxyl group"). As a consequence, it is preferred in some embodiments that the conjugate lacks attachment of the water-soluble, non-peptidic oligomer at a binding hydroxyl group. A "binding hydroxyl group" for any given protease inhibitor can be determined by one of ordinary skill in the art by, for example, experimental testing and/or by comparing the structure of the protease inhibitor of interest with the structure of saquinavir and determining which hydroxyl group in the protease inhibitor corresponds to the "binding hydroxyl group" at position 26 in saquinavir.

Pharmaceutical Compositions

The present invention also includes pharmaceutical preparations comprising an HIV protease inhibitor (whether "potent" or not) in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

Dosage Forms

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

Administration

The disclosure also provides a method for administering a conjugate as provided herein to a patient suffering from a condition that is responsive to treatment with the conjugate. As previously mentioned, in one aspect, the method comprises administering a potent HIV protease inhibitor. The mode of administration can be oral, but other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

Depending upon the subject method, any route suited for delivery of the potent protease inhibitor to the biological system (e.g., individual) can be used. If, for example, the biological system is a cell culture, administration can simply involve adding, via a pipette or dropper (for example), an aliquot of liquid containing the potent protease inhibitor. To the extent that the biological system is an individual infected with a virus, administering the potent protease inhibitor can take place via oral administration, but other modes of administration are also contemplated, such as pulmonary, nasal, buccal, rectal, sublingual, transdermal, and parenteral, wherein an individual infected with HIV is administered a potent HIV protease inhibitor and an individual infected with HCV is administered a potent HCV protease inhibitor.

In some instances the potent protease inhibitor (e.g., a HIV protease inhibitor or a hepatitis virus protease inhibitor such as a HCV protease inhibitor) is administered to an individual as part of a potent protease inhibitor therapy (e.g., a potent HIV protease inhibitor therapy or a potent hepatitis virus protease inhibitor therapy). By potent protease inhibitor therapy is meant a regimen in which at least one protease inhibitor is administered to effect some measure of protease inhibition in a biological system (e.g., an individual infected with HIV or an individual infected with HCV). Such a protease inhibitor therapy may also include one or more other drugs such as (i) a pharmacoenhancer of the potent protease inhibitor, (ii) a drug to allieviate a side effect of a potent HIV protease inhibitor, and/or (iii) a means to effect some measure of HIV protease inhibition in the biological system. It is also recognized, however, that one or more other active agents may also be administered to the biological system for reasons other than to effect protease inhibition; in which case, such other active agent(s) are not considered to be a part the potent HIV protease inhibitor therapy.

In one or more particular embodiments in which a potent protease inhibitor therapy is being administered to a biological system (e.g., individual), it is preferred that said potent protease inhibitor therapy does not include the co-administration of a CYP3A4 inhibitor. Conventionally, co-administration of the CYP3A4 inhibitor (e.g., ritonavir) would take place prior to, simultaneously with, or after administration of the protease inhibitor. In one or more embodiments of the present invention, however, the potent protease inhibitor therapy does not include such co-administration of a CYP3A4 inhibitor (ritonavir).

Ritonavir or other CYP3A4 inhibitors are often included as pharmacoenhancers in conventional protease inhibitor therapy to effectively supply a "boosting" strategy. The "boosting" strategy is believed to increase the exposure of the protease inhibitor by leveraging the CYP3A4 inhibitor's ability to inhibit cytochrome P-450 3A4-mediated metabolism of the protease inhibitor.

Although any CYP3A4 inhibitor can theoretically be used to inhibit cytochrome P450 3A4-mediated metabolism (including cytochrome P-450 3A4-mediated metabolism of the HIV protease inhibitor), the conventional approach has been the co-administration of ritonavir, which, in addition to its protease inhibitory activity, is a CYP3A inhibitor.

In one or more embodiments of the invention, provided is a method comprising administering a potent protease inhibitor (e.g., a potent HIV protease inhibitor or a potent hepatitis virus protease inhibitor such as a potent HCV protease inhibitor) to a CYP3A4-competent biological system.

By a CYP3A4-competent biological system is meant a cytochrome P450 3A4-containing biological system—containing a plurality of functional cytochrome P450 3A4 enzymes—in which a majority (i.e., greater than 50%) of that plurality are functioning and not inhibited by a CYP3A4 inhibitor. Thus, for example, a biological system (such as a cell culture) in which an excess of ritonavir (relative functional cytochrome P450 3A4 enzymes) was administered would not be considered a cytochrome P450 3A4-competent biological system. Also, a biological system (such as an individual infected with HIV and/or HCV) would not be considered a CYP3A4-competent biological system, for example, if the individual were taking ritonavir at 200 mg a day (either via a divided dose of 100 mg twice a day or 200 mg once a day). The biological system can be an in vitro cellular system as well as a human.

In instances where parenteral administration is utilized, it may be necessary to employ somewhat bigger oligomers (i.e., polymers) than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature and/or can be determined experimentally. Generally, a therapeutically effective amount is an amount within one or more of the following ranges: from 0.001 mg/day to 10000 mg/day; from 0.01 mg/day to 7500 mg/day; from 0.10 mg/day to 5000 mg/day; from 1 mg/day to 4000 mg/day; and from 10 mg/day to 2000 mg/day.

The unit dosage of any given potent HIV protease inhibitor (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the potent HIV protease inhibitor is that doing so provides HIV protease activity in a biological system without the need to co-administer a 3YP3A4 inhibitor, thereby reducing the complexities inherent with coordinating the administration of two agents to achieve relatively high and efficient HIV protease inhibition in a biological system. Such a benefit has utility in simplifying in vitro and in vivo assays. In addition, in a patient suffering from HIV, the methods described herein are expected to reduce the complexities of protease inhibitor-based therapies.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

The nomenclature used in the following examples corresponds to the following chemical structures.

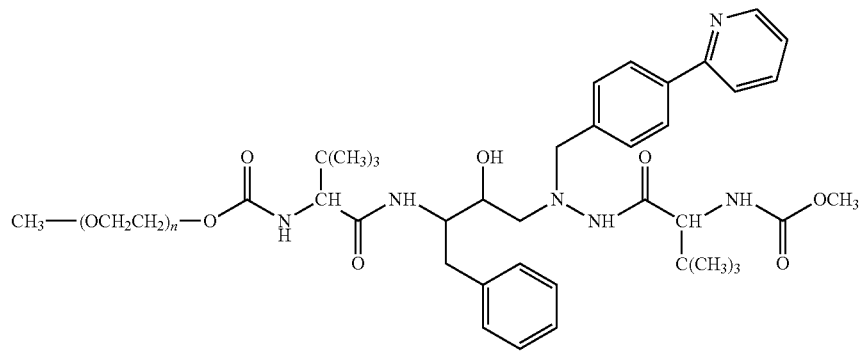

Mono-mPEGn-Atazanavir (n = 1, 3, 5, 6, 7)

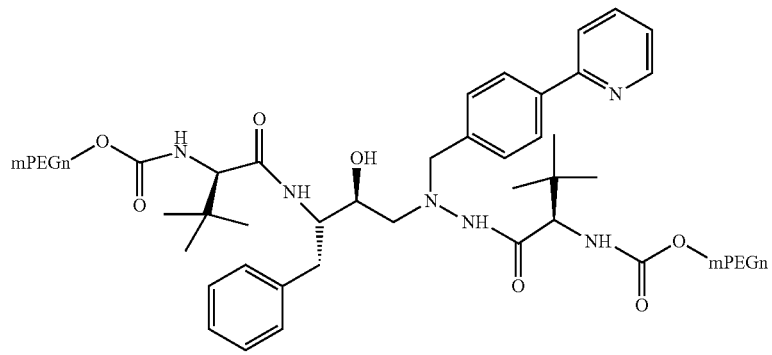

Di-mPEGn-Atazanavir

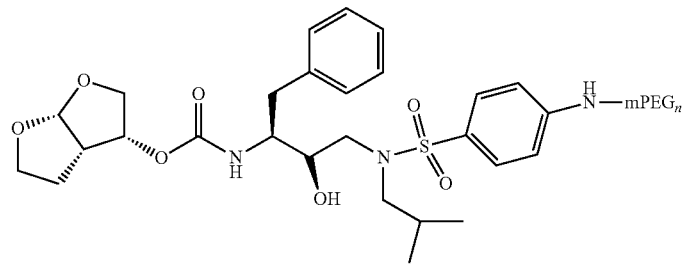

mPEGn-N-Darunavir (n - 3, 5, 7)

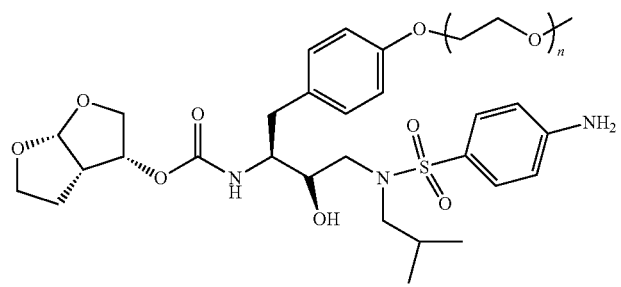
mPEGn-O-Darunavir (wherein n = 3, 5, 7)
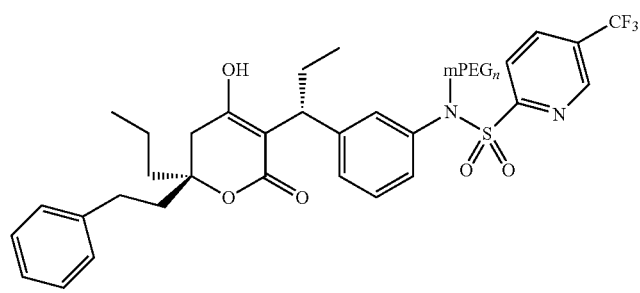
mPEGn-amide-Tipranavir
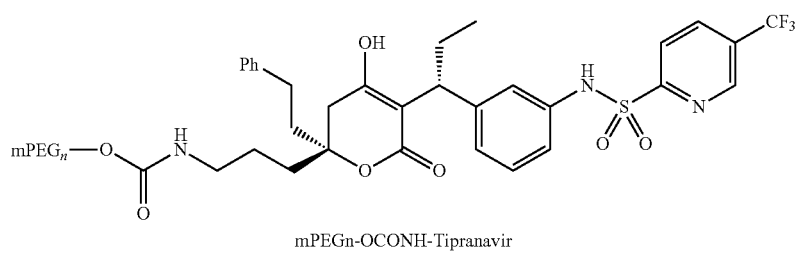
mPEGn-OCONH-Tipranavir
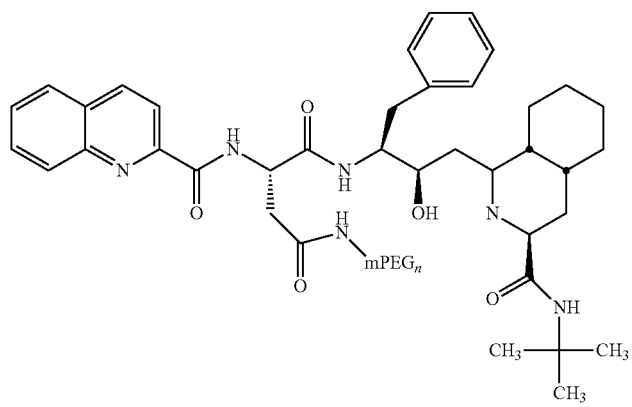
mPEGn-NHCO-Saquinavir The synthesis of these structures is provided in PCT preparation of these structures is provided herein and/or in PCT/US2008/003354 (WO2008/112289).

With respect to mono-mPEG3-Atazanavir, for example, the following synthesis was followed.

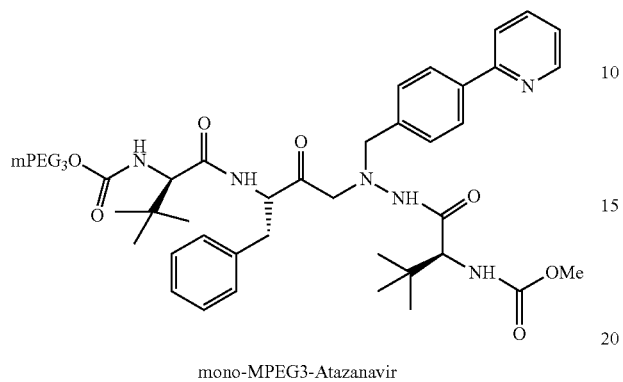

mono-MPEG3-Atazanavir

Materials

L-tert-Leucine, methyl chloroformate, tert-butyl carbazate, N-(3-Dimethylaminopropyl)-N'-ethylcarbodiimide (EDC), 1-hydroxybenzotriazole (HOBT), 4-methylmorpholine (NMM), ethyl acetate, 4 M HCl in dioxane, 37% HCl (aqueous), Z-L-Phe chloromethyl ketone, NaHCO$_3$, Sodium Iodide, acetonitrile, isopropyl alcohol, triethylamine, sodium cyanoborohydride, p-toluenesulfonic acid, tetrahydrofuran, DSC, DCM, 10% Pd—C, methanol, ethanol, TPTU, DIPEA, LTBA, diethyl ether.

Methods:

All reactions with air- or moisture-sensitive reactants and solvents were carried out under nitrogen atmosphere. In general, reagents and solvents were used as purchased without further purification. Analytical thin-layer chromatography was performed on silica F254 glass plates (Biotage). Components were visualized by UV light of 254 nm or by spraying with phosphomolybdic acid, or ninhydrin. Flash chromatography was performed on a Biotage SP4 system. $^1$H NMR spectra: Bruker 300 MHz; chemical shifts of signals are expressed in parts per million (ppm) and are referenced to the deuterated solvents used. MS spectra: rapid resolution Zorbax C18 column; 4.6×50 mm; 1.8 μm. HPLC method had the following parameters: column, Betasil C18, 5-μm (100×2.1 mm); flow, 0.5 mL/min; gradient, 0-23 min, 20% acetonitrile/0.1% TFA in water/0.1% TFA to 100% acetonitrile/0.1% TFA; detection, 230 nm. $t_R$ refers to the retention time.

Abbreviations: TPTU, O-(1,2-Dihydro-2-oxo-1-pyridyl)-N, N, N', N'-tetramethyluroniumtetrafluoroborate; DIPEA, N, N'-Diisopropylethylamine; DSC, N, N'-Disuccinimidyl carbonate.

The general synthetic scheme for preparing an aryl hydrazine (9) used in the preparation of mono-mPEG3-Atazanavir is provided below.

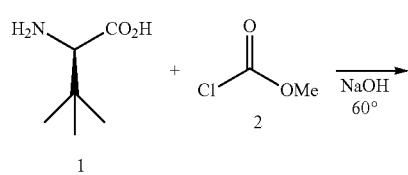

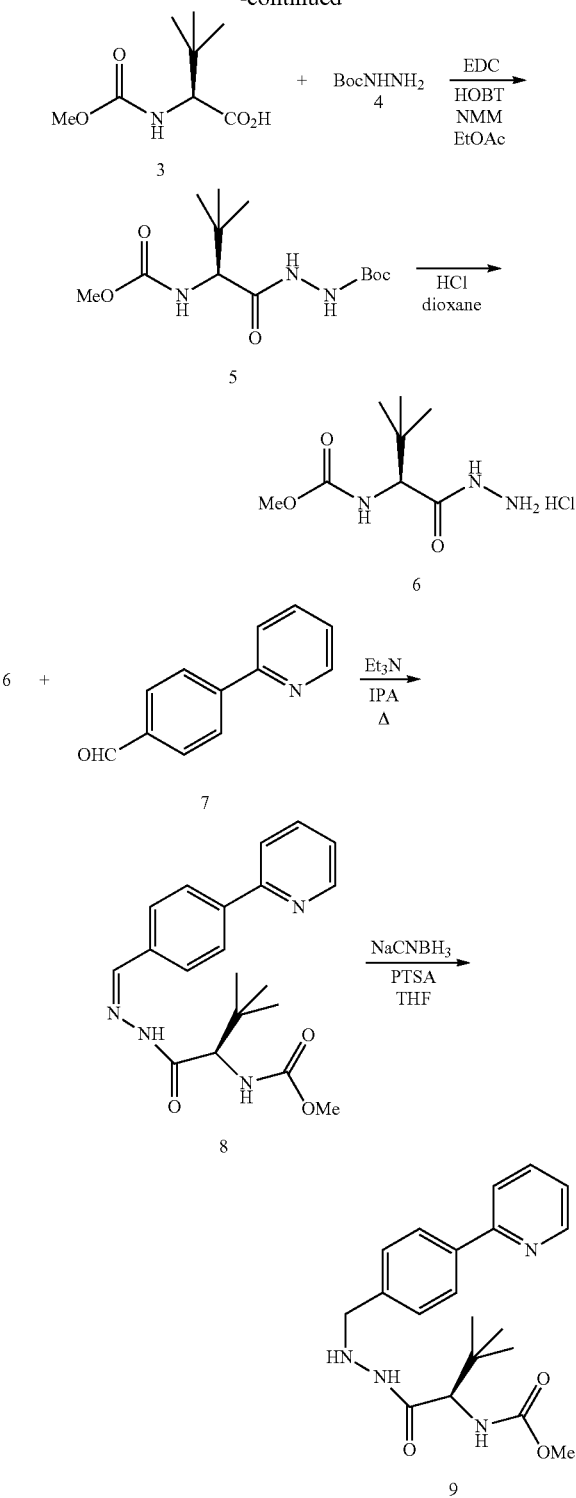

2-Methoxycarbonylamino-3,3-dimethyl-butyric Acid (3)

Into a 250 mL flask was placed L-tert-Leucine (5.0 gm, 38 mmol), 2N NaOH (66 mL), and methyl chloroformate (5.86 mL, 76 mmol, 2.0 equivalents). The reaction mixture was heated to 60° C., turning light-yellow. After approximately 20 hours, the heat was removed and the mixture cooled to room temperature, and then to 0° C. The reaction mixture was quenched at 0° C. with 2 N HCl (40 mL) to pH 1. The acidified mixture was transferred to a separatory funnel and extracted with ethyl acetate (3×50 mL). The combined organic layers were washed with water (2×150 mL), and saturated NaCl (150 mL), and then dried over Na$_2$SO$_4$. The organic layer was filtered and concentrated under reduced pressure to give a clear oil. The oil was azeotroped with toluene (3×50 mL), and then dried under high vacuum to give 6.4 gm (89%) of 3 as a white solid. $^1$H NMR (DMSO) δ 12.51 (bs, 1H), 7.28 (d, 1H), 3.80 (d, 1H), 3.53 (s, 3H), 0.93 (s, 9H); MS (M)$^+$=190; HPLC $t_R$ 2.8 minutes.

N'-(2-Methoxycarbonylamino-3, 3-dimethyl-butyryl)-hydrazinecarboxylic Acid tert-butyl Ester (5)

Methoxycarbonyl-L-tert-Leucine (3) (1.37 gm, 7.24 mmol) was dissolved in anhydrous ethyl acetate (21 mL). To the clear solution was added N-(3-dimethylaminopropyl)-N'-ethylcarbodiimide (EDC) (1.12 gm, 5.82 mmol, 1.1 equivalents). The suspension was stirred under nitrogen at room temperature. After ten minutes added HOBT (1.08 gm, 7.97 mmol, 1.1 equivalents), followed by 4-methyl-morpholine (1.35 mL, 12.32 mmol, 1.7 equivalents). After another 30 minutes, added t-butyl carbazate (1.05 gm, 7.97 mmol, 1.1 equivalents) and the light-yellow suspension continued stirring at room temperature. After 20 hours, the reaction mixture was diluted with ethyl acetate (50 mL) and transferred to a separatory funnel. The aqueous layer was partitioned with saturated NaHCO$_3$. The aqueous layer was extracted with ethyl acetate (3×50 mL). The combined organic layers were washed with saturated NaCl and dried over Na$_2$SO$_4$. After filtering and concentrating under reduced pressure, the residue was purified by Biotage chromatography (0 to 3% methanol/dichloromethane gradient) to give 2.05 gm (94%) of 5 as a white foam solid. $^1$H NMR (MeOD) δ 3.91 (bs, 1H), 3.62 (s, 3H), 1.42 (s, 9H), 0.98 (s, 9H); MS (M)$^+$=304; HPLC $t_R$ 5.5 minutes.

(1-Hydrazinocarbonyl-2, 2-dimethyl-propyl)-carbamic Acid Methyl Ester HCl (6)

Intermediate (5) (12.7 gm, 41 mmol) was dissolved in 1,4-dioxane (100 mL), followed by slow addition of 4.0 M HCl in dioxane (25 mL). The light-yellow mixture was stirred under nitrogen at room temperature. After 18 hours the cloudy mixture was concentrated under reduced pressure. The residue was azeotroped with toluene (3×30 mL), and then dried under high vacuum to give 10.9 gm of a white solid (quantitative). $^1$H NMR (DMSO) δ 11.23 (s, 1H), 7.41 (d, 1H), 7.22 (m, 1H), 3.98 (d, 1H), 0.92 (s, 9H); MS (M)$^+$=204; HPLC $t_R$ 0.67 minutes.

[2,2-Dimethyl-1-(4-pyridin-2-yl-benzylidene-hydrazinocarbonyl)-propyl]-carbamic Acid Methyl Ester (8)

Methoxycarbonyl-L-tert-Leucine hydrazine (6) (1.35 gm, 6.65 mmol) was taken up in i-PrOH (60 mL) and then added pyridyl benzaldehyde (7) (1.22 gm, 6.65 mmol). The yellow reaction mixture was heated to reflux (85° C.). After approximately two hours, TLC and HPLC showed the reaction was complete. The heat was removed and the thick yellow mixture was cooled to 0° C. The solvent was removed under reduced pressure. The yellow residue was taken up in DCM (250 mL) and partitioned with water. The aqueous layer was extracted with DCM (4×50 mL). The combined organics were washed with saturated NaHCO$_3$, water, 0.05 M HCl, and saturated NaCl (approximately 300 mL each). The organic layers were dried (Na$_2$SO$_4$), filtered and concentrated under reduced pressure to give a yellow solid. Purification by Biotage® chromatography (0 to 3% methanol/DCM gradient) gave 1.34 gm (55%) of 8 as a white solid. By NMR it is approximately a 1:1 mixture of cis-trans isomers. $^1$H NMR (CDCl$_3$) δ 10.30 (s, 1H), 9.80 (s, 1H), 8.64 (d, 1H), 8.60 (d, 1H), 8.11 (s, 1H), 8.04 (d, 2H), 7.98 (m, 2H), 7.85 (m, 6H), 7.83 (m, 2H), 7.22 (m, 2H), 5.92 (d, 1H), 5.56 (d, 1H), 5.32 (d, 1H), 4.10 (d, 1H), 3.64 (d, 6H), 1.02 (d, 18H); MS (M)$^+$=369; HPLC $t_R$ 2.9 minutes.

{2,2-Dimethyl-1-[N'-(4-pyridin-2-yl-benzyl)-hydrazinocarbonyl]-propyl}-carbamic Acid Methyl Ester (9)

Hydrazone (8) (1.10 gm, 2.98 mmol) was dissolved in anhydrous THF (30 mL). Then added solid NaCNBH$_3$ (0.40 gm, 5.97 mmol, 2.0 equivalents) all at once, followed by slow addition via syringe of PTSA (p-toluene sulfonic acid) (1.13 gm, 5.97 mmol, 2.0 equivalents) in THF (15 mL). There was bubbling observed during the PTSA addition. The cloudy mixture was heated to reflux (70° C.). After approximately 40 h, the cloudy reaction mixture was concentrated under reduced pressure and the white residue partitioned with DCM (30 mL) and water (50 mL). The aqueous layer was extracted with DCM (3×40 mL). The combined organic layers were washed with water, and saturated NaCl. The organic layers were dried (Na$_2$SO$_4$), filtered and concentrated under reduced pressure to give a white foam solid. Purification by Biotage® chromatography (0 to 3% methanol/DCM gradient) gave 0.34 gm (67%) of 9 as a white solid. $^1$H NMR (MeOD) δ 8.55 (s, 1H), 7.85 (m, 4H), 7.50 (d, 2H), 7.32 (m, 1H), 4.05 (s, 2H), 3.62 (s, 3H), 0.91 (s, 9H); MS (M)$^+$=371; HPLC $t_R$ 1.8 minutes.

The general synthetic scheme for preparing Cbz-Azaketo Isotere (11) used in the preparation of mono-mPEG3-Atazanavir is provided below.

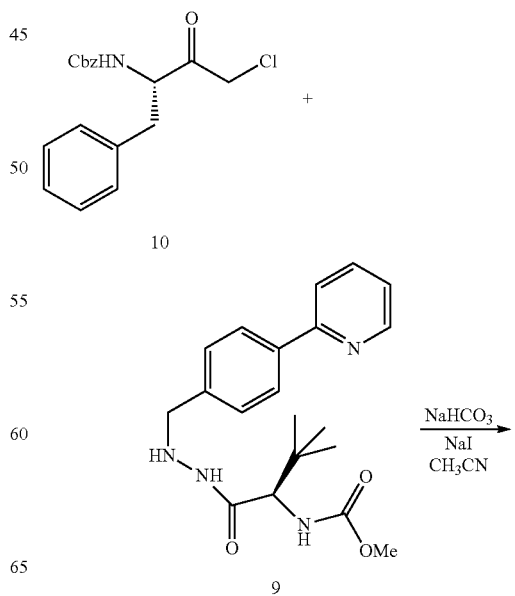

-continued

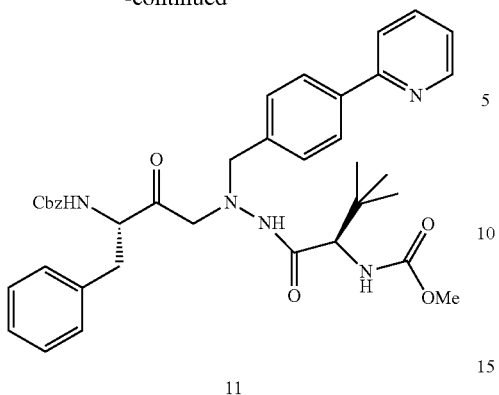

11

{1-Benzyl-3-[N'-(2-methoxycarbonylamino-3,3-dimethyl-butyryl)-N-(4-pyridin-2-yl-benzyl)-hydrazino]-2-oxo-propyl}-carbamic Acid Benzyl Ester (11)

Z-L-Phe chloromethyl ketone (0.67 gm, 2.01 mmol) was taken up in anhydrous acetonitrile (30 mL). Then added NaI (0.33 gm, 2.21 mmol, 1.1 equivalents), followed by NaHCO$_3$ (0.33 gm, 4.02 mmol, 2.0 equivalents). The solution was stirred for ten minutes at room temperature. Hydrazine (9) (0.82 gm, 2.21 mmol, 1.1 equivalents) in acetonitrile (20 mL) was then added via syringe. The cloudy yellow reaction mixture was heated to 60° C. After approximately 18 hours, the cloudy yellow mixture was cooled to room temperature. The solvent was removed under reduced pressure. The yellow residue was partitioned with DCM (30 mL) and water (90 mL). The aqueous layer was extracted with DCM (3×30 mL). The combined organic layers were washed with water, and saturated NaCl. The organic layers were dried (Na$_2$SO$_4$), filtered and concentrated under reduced pressure to give a white foam solid. Purification by Biotage® chromatography (0 to 3% methanol/DCM gradient; 15CV) gave 1.14 gm (85%) of 11 as a white solid. TLC R$_f$ (5% methanol/dichloromethane)=0.26; $^1$H NMR (CDCl$_3$) δ 8.69 (d, 1H), 7.92 (d, 2H), 7.72 (m, 2H), 7.44 (d, 2H), 7.26 (m, 10H), 7.11 (d, 2H), 4.70 (d, 1H), 4.12 (dd, 2H), 3.75 (dd, 2H), 3.62 (m, 1H), 3.57 (s, 3H), 2.99 (m, 1H), 2.87 (m, 1H), 1.45 (s, 1H), 1.03 (m, 2H), 0.81 (s, 9H). (s, 2H), 3.62 (s, 3H); MS (M)$^+$=666; HPLC t$_R$ 9.5 minutes.

The general synthetic scheme for preparing Cbz-Aza Isotere (12) used in the preparation of mono-mPEG3-Atazanavir is provided below.

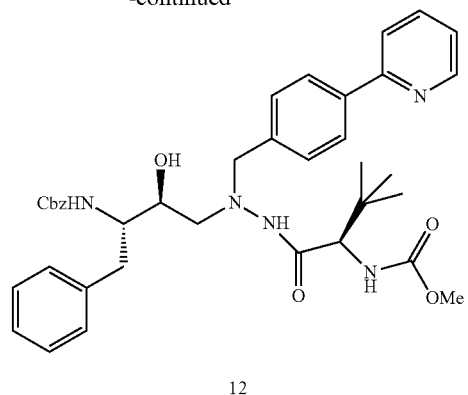

12

{1-Benzyl-2-hydroxy-3-[N'-(2-methoxycarbonylamino-3,3-dimethyl-butyryl)-N-(4-pyridin-2-yl-benzyl)-hydrazino]-propyl}-carbamic Acid Benzyl Ester (12)

The Cbz-azaketone (11) (0.84 gm, 1.26 mmol) was taken up in diethyl ether (15 mL) and cooled to 0° C. To the white suspension was added LTBA (Lithium tri-tert-butoxy-aluminum hydride) (0.80 gm, 3.15 mmol, 2.5 equivalents), at 0° C. The light-yellow suspension was stirred under nitrogen at 0° C. After one hour at 0° C., the cloudy yellow mixture was stored overnight at −20° C. The reaction mixture was quenched with water (0.9 mL), at 0° C. The solvent was removed under reduced pressure. The residue was partitioned with DCM (30 mL) and water (90 mL). The aqueous layer was extracted with DCM (3×30 mL). The combined organic layers were washed with water, and saturated NaCl. The organic layers were dried (Na$_2$SO$_4$), filtered and concentrated under reduced pressure to give a white foam solid. Purification by Biotage® chromatography (0 to 3% methanol/diethyl ether gradient; 20CV) gave 0.45 gm (54%) of 12 as a white solid. TLC R$_f$ (5% methanol/diethyl ether)=0.50; $^1$H NMR (CDCl$_3$) δ 8.64 (d, 1H), 7.88 (d, 2H), 7.74 (m, 1H), 7.65 (m, 1H), 7.35 (m, 2H), 7.20 (m, 14H), 5.20 (dd, 2H), 4.95 (m, 2H), 4.62 (d, 1H), 4.02 (d, 1H), 3.82 (d, 1H), 3.70 (m, 1H), 3.55 (m, 2H), 3.45 (m, 2H), 3.42 (s, 1H), 2.86 (m, 2H), 2.78 (m, 1H), 2.54 (d, 1H), 1.35 (s, 1H), 1.15 (m, 1H), 0.75 (m, 2H), 0.64 (s, 6H); MS (M)$^+$=668; HPLC t$_R$ 9.2 minutes.

The general synthetic scheme for preparing Amino-azaisotere (13) used in the preparation of mono-mPEG3-Atazanavir is provided below.

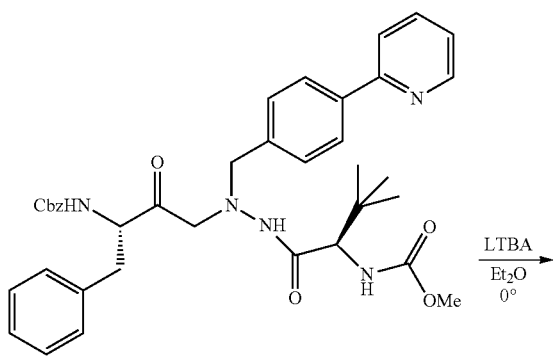

11

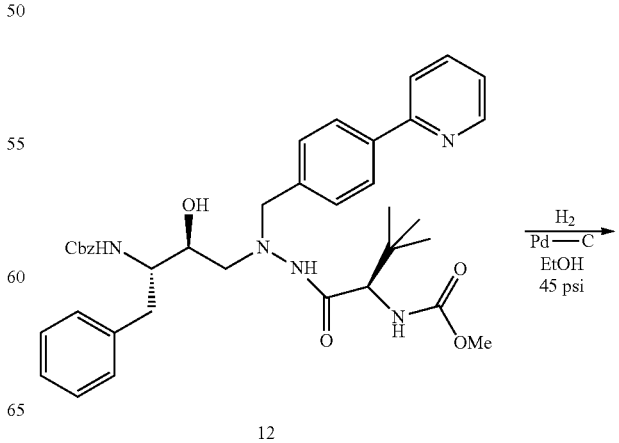

12

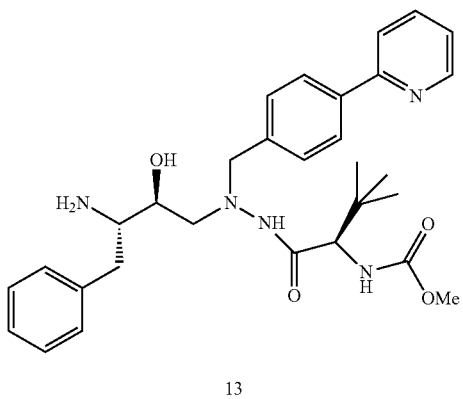

13

{1-[N'-(3-Amino-2-hydroxy-4-phenyl-butyl)-N'-(4-pyridin-2-yl-benzyl)-hydrazinocarbonyl]-2,2-dimethyl-propyl}-carbamic Acid Methyl Ester (13)

The Cbz-aza-isostere (12) (0.34 gm, 0.50 mmol) was taken up in absolute ethanol (150 mL) and charged with 10% Pd—C(0.10 gm). The mixture was subjected to hydrogenolysis, at 45 psi. After 18 hours the catalyst was filtered through celite. The cake was washed with ethanol (35 mL), and the filtrate was concentrated under reduced pressure to give 0.19 gm (70%) of 13 as a clear oil. TLC $R_f$ (5% methanol/dichloro-methane)=0.02; MS (M)$^+$=534; HPLC $t_R$ 3.9 min. The material was used in the next step without further purification.

The general synthetic scheme for preparing PEG-tert-Leucine reagent (16) and mono-mPEG$_3$-Atazanavir Conjugate (17) used in the preparation of mono-mPEG3-Atazanavir is provided below.

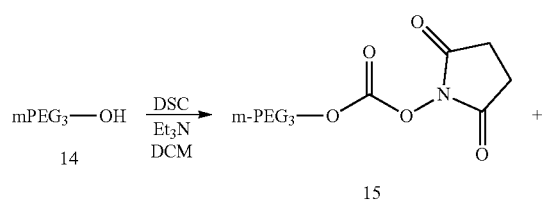

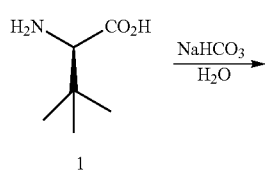

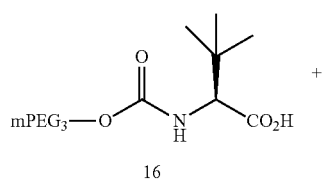

16

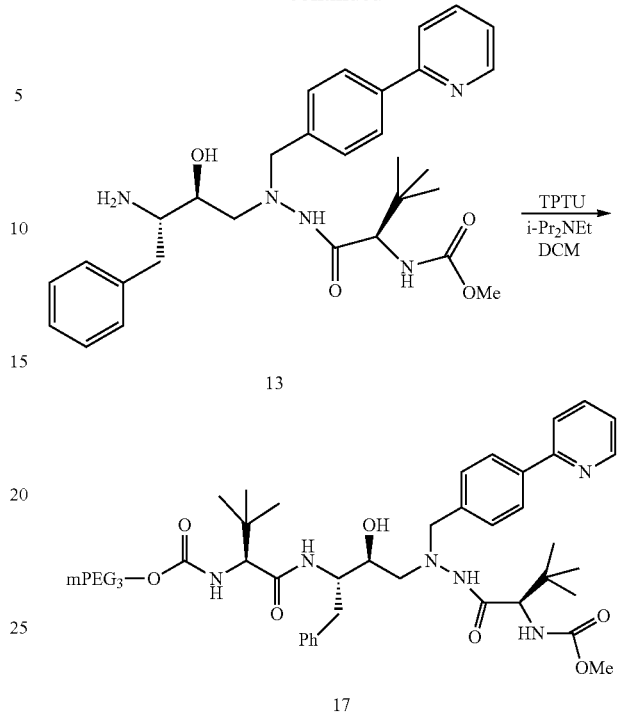

17 m-PEG-3-SC-carbonate (15)

Into a 100 mL flask was placed mPEG3-OH (14) (2.0 g, 12.1 mmol) and anhydrous dichloromethane (25 mL). The clear solution was cooled to 0° C., and then triethylamine (1.86 mL, 13.4 mmol, 1.1 equivalents) was added slowly. The solution was stirred for 15 minutes at 0° C., and then was added to a second flask containing a suspension of DSC (3.1 g, 12.1 mmol) in dichloromethane (20 mL). The reaction mixture was allowed to equilibrate to room temperature. After approximately 18 hours, the light-yellow reaction mixture was diluted with dichloromethane (60 mL), transferred to a separatory funnel, and partitioned with deionized water (100 mL). The aqueous layer was extracted with dichloromethane (4×80 mL). The combined organics were washed with water, saturated sodium bicarbonate, and saturated sodium chloride. The dried organic layer was filtered, concentrated under reduced pressure and dried overnight under high vacuum, to give 2.79 g (75%) of mPEG3-SC-carbonate as a light yellow oil. $^1$H NMR (CDCl$_3$) δ 4.40 (m, 2H), 3.80 (m, 2H), 3.70 (bs, 6H), 3.60 (m, 2H), 3.35 (s, 3H), 2.80 (s, 4H); LC/MS=306 (M+1).

mPEG-$_3$-L-tert-Leucine (16)

Into a 125 mL flask was placed L-tert-Leucine (1) (0.43 g, 3.27 mmol) and deionized water (12 mL). The solution was stirred for 30 min until clear, followed by the addition of solid sodium bicarbonate (1.27 g, 15.0 mmol, 4.6 equivalents). The cloudy solution was stirred at room temperature, under nitrogen. In a second flask the mPEG3-SC-carbonate (15) (1.24 g, 4.09 mmol, 1.25 equiv.) was taken up in deionized water (12 mL) and this solution was added all at once to the basic L-tert-Leucine solution. The cloudy light-yellow reaction mixture was stirred at room temperature, under nitrogen. After approximately 20 h, the clear mixture was cooled to 0° C., and carefully acidified with 2 N HCl to pH 1 (20 mL). The acidic mixture was transferred to a separatory funnel and partitioned with dichloromethane (50 mL) and additional water (50 mL). The aqueous layer was extracted with dichloromethane (4×50 mL). The combined organic layers were washed with water and saturated sodium chloride, and dried over sodium sulfate. The dried organic layer was filtered, concentrated under reduced pressure and dried under high vacuum overnight, to give 0.83 g (79%) of mPEG3-L-tert-Leucine (16) as a pale yellow oil. $^1$H NMR (CDCl$_3$) δ 5.45 (d, 1H), 4.26-4.35 (m, 2H), 4.14 (m, 1H), 3.70 (bs, 17H), 3.65 (m, 2H), 3.32 (s, 3H), 0.96 (s, 9H); LC/MS=322 (M+1).

{1-[N'-[2-Hydroxy-3-(2-{2-[2-(2-methoxy-ethoxy)-ethoxy]-ethoxycarbonylamino}-3,3-dimethyl-butyrylamino)-4-phenyl-butyl]-N'-(4-pyridin-2-yl-benzyl)-hydrazinocarbonyl]-2,2-dimethyl-propyl}-carbamic Acid Methyl Ester (17)

The mPEG3-tert-Leucine reagent (16) (0.34 gm, 1.06 mmol, 3.0 equivalents) was taken up in anhydrous dichloromethane (3.0 mL) and cooled to 0° C. TPTU (0.31 gm, 1.06 mmol, 3.0 equivalents) was added all at once, and the solution was stirred under nitrogen at 0° C. In a separate flask, the amino aza-isostere (13) (0.19 gm, 0.35 mmol) was taken up in anhydrous dichloromethane (3.0 mL) and diisopropylethylamine (0.37 mL, 2.13 mmol, 6.0 equivalents). This solution was added via syringe to the m-PEG$_3$-tert-Leucine solution, at 0° C. The ice bath was removed and the reaction mixture was allowed to equilibrate to room temperature. After approximately 18 hours at room temperature, the reaction mixture was diluted with dichloromethane (10 mL) and transferred to a separatory funnel, where it was partitioned with water (30 mL). The aqueous layer was extracted with dichloromethane (3×10 mL). The combined L-tert-Leucine (1), with methyl chloroformate (2), to give methoxycarbonyl-L-tert-Leucine (3). In addition to serving as an amino protecting group, the methoxycarbonyl-L-tert-Leucine moiety also establishes the correct stereochemistry of the t-butyl group. Reaction of (3) with tert-butylcarbazate gave the methoxycarbonyl-L-tert-Leucine-Boc protected hydrazine (5). Deprotection of the Boc group proceeded in quantitative yield to give the hydrazine hydrochloride salt (6). Reaction of the hydrazine salt (6) with the bis-aryl aldehyde (7) under reflux conditions gave bis-aryl hydrazone (8). Chemical reduction of the hydrazone (8), using sodium cyanoborohydride, provided the key building block bis-aryl hydrazine (9). With (9) in hand, an SN2 reaction with another intermediate, Cbz-chloromethyl ketone (10), gave Cbz-azaketone (11). Introduction of the required (S)-hydroxyl group was done via a diastereoselective reduction of (11) using the bulky reducing agent LTBA (lithium tri-tert-butoxyaluminum hydride) to give Cbz-aza-isostere (12). Removal of the Cbz protecting group was done under hydrogenolysis conditions (H$_2$, 10% Pd—C, 45 psi) to give the amino aza-isostere (13). The other intermediate for the mono-PEG$_3$-Atazanavir conjugate was the specialized PEG reagent containing the required stereochemistry for the Atazanavir conjugate. The synthesis began with m-PEGS-OH (14) reacted with N, N'-disuccinimidyl carbonate (DSC), to give m-PEG$_3$-DSC (15). Reaction with L-tert-Leucine gave the desired m-PEG$_3$-L-tert-Leucine reagent (16). Finally, under coupling conditions, the amino-aza-isostere (13) was reacted with m-PEG$_3$-L-tert-Leucine (16) to provide the mono-mPEG3-Atazanavir conjugate.

Using an approach similar to the one used to prepare mono-mPEG3-Atazanavir, Mono-mPEGn-Atazanavir conjugates of different PEG sizes (e.g., n=1, 5, 6 and 7) were prepared.

With respect to mPEGn-OCONH-Tripranavir conjugates, for example, the following synthesis was followed.

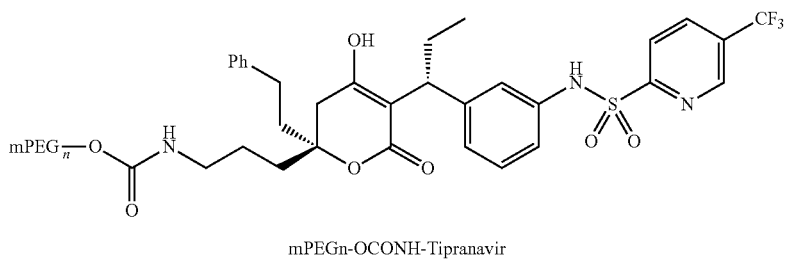

mPEGn-OCONH-Tipranavir organics were washed with water, and saturated NaCl (20 mL each). The organic layer was dried (Na$_2$SO$_4$), filtered, and concentrated under reduced pressure, to give a clear oil. Purification by Biotage® chromatography (0 to 3% methanol/dichloromethane gradient; 20CV) gave 0.21 gm (72%) of 17 as a white solid. TLC R$_f$ (8% methanol/dichloromethane)=0.32; $^1$H NMR (CDCl$_3$) δ 8.59 (d, 1H), 7.83 (d, 2H), 7.64 (m, 2H), 7.36 (m, 3H), 7.13 (m, 7H), 6.64 (m, 1H), 5.45 (d, 2H), 4.95 (m, 1H), 4.11 (m, 2H), 3.98 (m, 2H), 3.90 (m, 1H), 3.74 (m, 1H), 3.58 (m, 10H), 3.48 (m, 2H), 3.29 (s, 3H), 2.88 (m, 2H), 2.57 (m, 3H), 0.75 (s, 9H); MS (M)$^+$=668; HPLC t$_R$ 7.7 min.

Results and Discussion:

The synthesis of the bis-aryl hydrazine (9) is described above and represents an approach for preparing an intermediate useful for the preparing the atazanavir "core." The synthesis began with reaction of the chiral amino acid, N-Carbethoxyphthalimide, 4-Aminobutyraldehyde diethyl acetal, Cupper(I) bromide-dimethylsulfide complex (CuBr.DMS), Phenethylmagnesium chloride (1.0 M in THF), Boron trifluoride diethyl etherate (BF$_3$.Et$_2$O), Dimethylsulfoxide (DMSO), Trifluoroacetic acid, Dicyclohexylcarbodiimide (DCC), Butyllithium (1.6 M), Pyridinium chlorochromate (PCC), Magnesium bromide diethyl etherate (MgBr$_2$.OEt2), Potassium bis(trimethylsilyl)-amide (KHMDS, 0.5 M), Acetyl chloride, Titanium (IV) isopropoxide, Titanium chloride (TiCl$_4$), Potassium tert-butoxide (KOBu$^t$), 4-(Dimethylamine)-pyridine (DMAP), Hydrozine (NH$_2$NH$_2$), 2-Methoxyethanol, Tri(ethyleneglycol) monomethylether (95%), 4-Nitrophenyl chloroformate, Sodium hydroxide, N, N-diisopropylethylamine (DIPEA), Palladium 10% wt % on activated carbon, Methylamine, Triethylamine, Anhydrous methanol, and Pyridine were purchased from Sigma-Aldrich (St Louis, Mo.). mPEG5-OH were obtained from India Sai CRO. 5-Trifluoromethyl-2-pyridinesulfonyl chloride was purchased from Toronto research chemicals (North York, ON, Canada). DCM was distilled from $CaH_2$. Tetrahydrofuran (THF), ether, Ethyl acetate, and other organic solvents were used as they purchased.

A general synthetic scheme for preparing a ketone intermediate useful for preparing mPEGn-OCONH-Tripranavir conjugates is provided below.

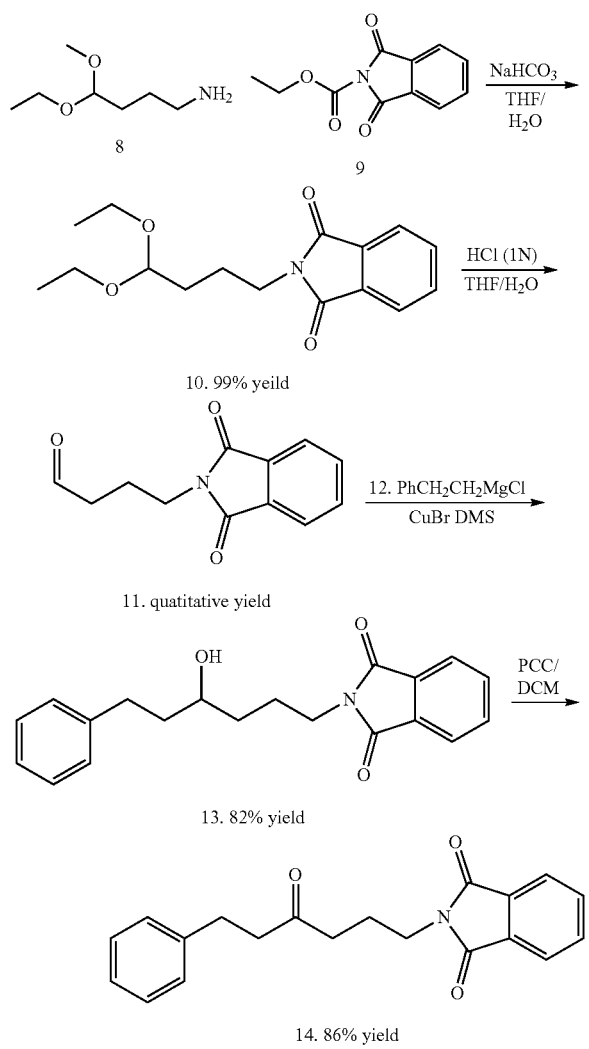

Phthalimide Protection:

Deionized water (50 mL) and THF (50 mL) were added in a 250-mL flask. $NaHCO_3$ (5.67 g, 67.5 mmol) and 4-aminobutyraldehyde diethyl acetal (8) (12.0 mL, 67.5 mmol) were suspended in this solution. N-carbethoxyphthalimide (9) (15.54 g, 70.9 mmol) was then added and the solution began become clear within 15 minutes. The reaction was kept at ambient temperature for two hours and was diluted with EtOAc (500 mL) and water (20 mL) to dissolve the salt precipitation. The organic phase was separated and washed with brine (100 mL×2). It was then dried over $Na_2SO_4$, filtered, and concentrated to a colorless crude product. The residue was loaded on Biotage column (40 M×2, 5-27% EtOAc in Hex in 16 CV) and a colorless product (10) was collected (95-100% yield). The product solidified after overnight high vacuo drying. $R_f$=0.43 (Hex:EtOAc=3:1), LC-MS (ESI, $MH^+$) 292.1. $^1H$ NMR (300 MHz, $CDCl_3$) δ 1.19 (6H, t, J=7.2 Hz), 1.65-1.80 (4H, m), 3.46-3.54 (2H, m), 3.58-3.74 (4H, m), 4.51 (1H, t, J=5.7 Hz), 7.70-7.74 (2H, m), 7.83-7.86 (2H, m).

Acidic Acetal Hydrolysis:

In a 250-mL flask, the above phthalimide was dissolved in THF (56 mL) at ambient temperature. Hydrochloric acid (1N, 18 mL) was added and the hydrolysis was monitored by TLC. It was completed in 5-6 hrs and stopped by carefully addition of $NaHCO_3$ saturated solution. The solution was diluted with EtOAc (300 mL) and the organic phase was washed with brine and dried over $Na_2SO_4$. After filtration, it was concentrated and the product was solidified during overnight high vacuo drying. $R_f$=0.22 (Hex:EtOAc=3:1), RP-HPLC (betasil C18, 0.5 mL/min, 30-100% ACN in 10 min) 4.65 min, LC-MS (ESI, $MH^+$) 218.1. $^1H$ NMR (300 MHz, $CDCl_3$) δ 2.02 (2H, p, J=6.9 Hz), 2.54 (2H, dt, J=0.9, 7.2 Hz), 3.75 (2H, t, J=6.6 Hz), 7.71-7.74 (2H, m), 7.84-7.87 (2H, m), 9.78 (1H, t, J=0.9 Hz).

Grignard-Cupper Alkylation:

In a 500-mL flask, Cupper(I) bromide DMS (7.2 g, 35.1 mmol) was dissolved in THF (43 mL) and the solution was cooled to −35° C. Phenylethyl magnesium chloride (1M, 35.1 mL, 35.1 mmol) was added dropwise in ten minutes. The Mg-cupper reagent was kept at −30 to −10° C. over 20 minutes before it was cooled down to −78° C. and above aldehdye (2.54 g, 11.7 mmol) in THF (20 mL) was added dropwise during 15 minutes. $BF_3.Et_2O$ (5.88 mL, 46.8 mL) was also added dropwise during six minutes. The reaction temperature was kept below −65° C. over 30 minutes and then warm up to 6° C. over 2.5 hours. It was stopped by adding $NH_4OH$ to pH=9. The solution was then diluted with $NH_4Cl$ (100 mL) and $Et_2O$ (250 mL). The separated ether phase was washed with $NaHCO_3$ and brine and dried over $Na_2SO_4$. After filtration, it was concentrated on vacuo and sample residue was purified on Biotage (40 M, 20-44% EtOAc in Hex) in 16 CV. A slight yellow color product (13) was solidified (3.30 g, 87% yield) after overnight vacuo. $R_f$=0.16 (Hex:EtOAc=1:1), RP-HPLC (betasil C18, 0.5 mL/min, 30-100% ACN in 10 min) 6.06 min, LC-MS (ESI, $MH^+$) 324.1. $^1H$ NMR (300 MHz, $CDCl_3$) δ 1.46-1.54 (2H, m), 1.72-1.88 (4H, m), 2.61-2.84 (2H, m), 3.63-3.69 (1H, m), 3.73 (2H, t, J=7.2 Hz), 7.15-7.29 (5H, m), 7.68-7.73 (2H, m), 7.81-7.87 (2H, m).

Moffatt Oxidation:

The above secondary alcohol (13) (3.07 g, 9.50 mmol) was dissolved in DCM (125 mL) at ambient temperature. DMSO (6.75, 95 mmol), pyridine (1.54 mL, 19.0 mL), TFA (1.55 mL, 20.9 mL) were added in the order. Finally DCC (7.84 g, 38.0 mmol) was added and the reaction was kept at ambient temperature for overnight. The reaction was diluted with $NH_4Cl$ and extracted with DCM (20 mL×2). The combine organic phase was washed with brine and dried over $Na_2SO_4$. The DCU together with drying agent was filterated and the residue was dried over with Silica gel (20 g). The silical gel was loaded on Biotage column and purified (6-40% EtOAc/Hex over 16 CV). A colorless solidified product (14) was collected (1.50 g, 75% yield) after overnight drying. $R_f$=0.33 (Hex:EtOAc=3:1), RP-HPLC (betasil C18, 0.5 mL/min, 30-100% ACN in 10 min) 7.52 minutes, LC-MS (ESI, $MH^+$) 322.1. $^1H$ NMR (300 MHz, $CDCl_3$) δ 1.96 (2H, p, J=6.9 Hz), 2.45 (2H, t, J=7.2 Hz), 2.73 (2H, t, J=6.9 Hz), 2.88 (2H, t, J=7.2 Hz), 3.70 (2H, t, J=6.6 Hz), 7.15-7.28 (5H, m), 7.70-7.73 (2H, m), 7.83-7.86 (2H, m).

PCC Oxidation:

In a 500-mL flask, the above secondary alcohol (13) (12.86 g, 39.8 mmol) was dissolved in DCM. PCC (8.6 g, 39.8 mmol) was added and the reaction was kept at room temperature. In three hours, the additional PCC (about 8%) was added based on the TLC of remaining of starting material. The reaction was kept over 40 hours and the product mixture was filtrated though celite/silica gel layer and washed with DCM. The combined DCM solution was concentrated and the product residue was loaded on a Biotage column (40M×2, 6-40% EtOAc/Hex in 16 CV). A colorless solid product (14) (10.72 g, 86%) was collected after high vacuo drying.

An approach for conducting basic C—C conjugation and ti-catalyzed C—C conjugation useful in preparing mPEGn-OCONH-Tripranavir conjugates is provided below.

MHz, CDCl$_3$) δ 0.61 (3H, t, J=7.2 Hz), 1.63 (3H, s), 3.07 (1H, dt, J=3.3, 10.8 Hz), 4.22 (1H, dd, J=3.9, 8.7 Hz), 4.61 (4H, s), 4.67 (1H, t, J=9.0 Hz), 4.98 (1H, d, J=10.5 Hz), 5.42 (1H, dd, J=3.6, 8.7 Hz), 6.54-6.64 (3H, m), 7.09 (1H, t, J=8.1 Hz), 7.21-7.39 (15H, m).

Ti-Catalyzed C—C Conjugation:

In a N$_2$-protected 250-mL flask, distilled DCM (50 mL) was added following by addition of Ti(OPr)$_4$ (982 μL, 3.35 mmol) and TiCl$_4$ (1.03 mL, 9.41 mmol) in order. The mixture was cooled down to −78° C. in acetone/dry-ice bath and a mixture of substrate (33) (5.86 g, 10.5 mmol) in DCM (16 mL) was dropwise added in ten minutes. The reaction was kept at this temperature for 5 min before DIPEA (2.37 mL, 13.6 mmol) was added slowly in 5 min. The reaction was warm up to 0° C. and kept in 30 minutes. It was recooled down to −78° C. and a mixture of ketone (14) (from PCC

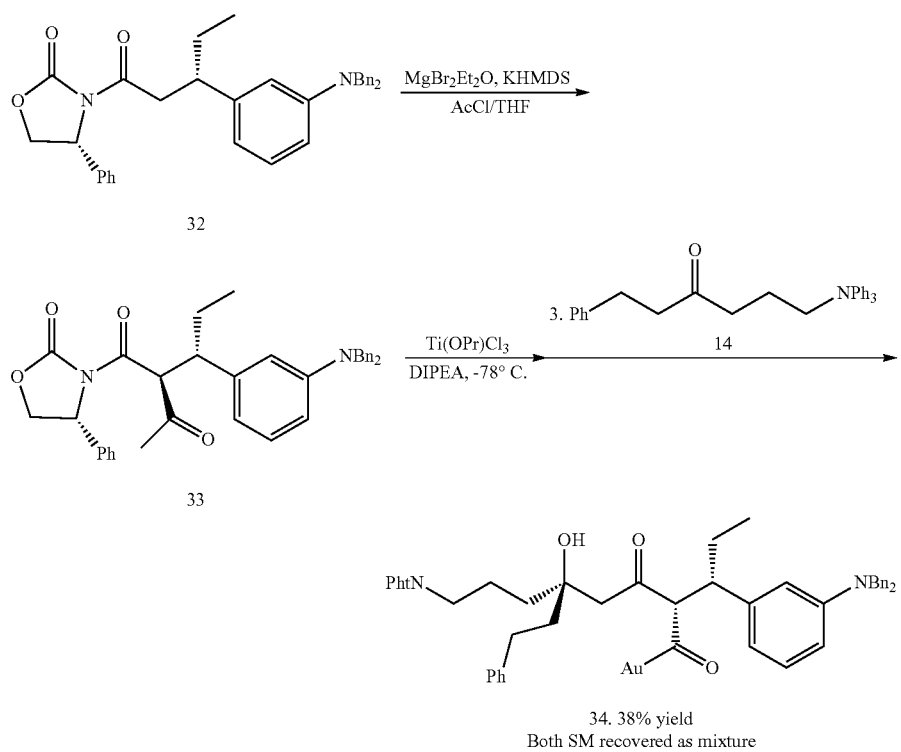

34. 38% yield
Both SM recovered as mixture

Base-Catalyzed Acetylation:

In a 250-mL flask, the substrate (32) (7.28 g, 14.05 mmol) and MgBr$_2$.OEt$_2$ (4.0 g, 15.5 mmol) were added. The flask was protected in dry N$_2$ and THF (68 mL) was added. The solution was cooled down to −78° C. in acetone/dry ice bath before KHMDS (0.5 M, 42.1 mL, 21.08 mmol) was dropwise added in ten minutes. The above mixture was kept at −78° C. for 30 minutes before acetyl chloride (1.50 mL, 21.08 mmol) was added in five minutes. The reaction mixture was warm up gradually during the overnight reaction. It was quenched by NH$_4$Cl (200 mL) and extracted with EtOAc (100 mL+50 mL×2). The combined organic phase was washed with brine and dry over Na$_2$SO$_4$. After filtration, it was concentrated and purified on the Biotage (40M×2, 6-16% EtOAc/Hex in 16 CV). The collected product gives a colorless foam product 33 (6.66 g, 85% yield) after vacuo drying. R$_f$=0.31 (Hex:EtOAc=3:1), RP-HPLC (betasil C18, 0.5 mL/min, 60-100% ACN in 10 minutes) 6.58 minutes; LC-MS (ESI, MH$^+$) 561.3. $^1$H NMR (300 oxidation, 3.36 g, 10.5 mmol) in DCM (10 mL) was added. The reaction mixture was warm up to 0° C. and kept in ice-water bath for another two hours. It was quenched by NH$_4$Cl (200 mL) and diluted with DCM (100 mL). The aqueous phase was extracted with DCM (50 mL×2) and the combined organic phase was washed with brine (150 mL). The organic phase was then dried over Na$_2$SO$_4$ and concentrated under the vacuo. The crude product mixture was purified on Biotage (40S×2, 12-42% EtOAc in Hex over 16 CV). The product (34) was solidified (3.48 g, 38% yield) after high vacuo. The starting material mixture also has been recovery (5.43 g, 47%). Since this product is a diasteromer mixture, the $^1$H NMR cannot be read and recorded. R$_f$=0.13 (Hex:EtOAc=3:1), RP-HPLC (betasil C18, 0.5 mL/min, 60-100% ACN in 10 minutes) 9.23 minutes; LC-MS (ESI, MH$^+$) 882.5.

An approach for the final steps for preparing mPEGn-OCONH-Tripranavir conjugates is provided below.

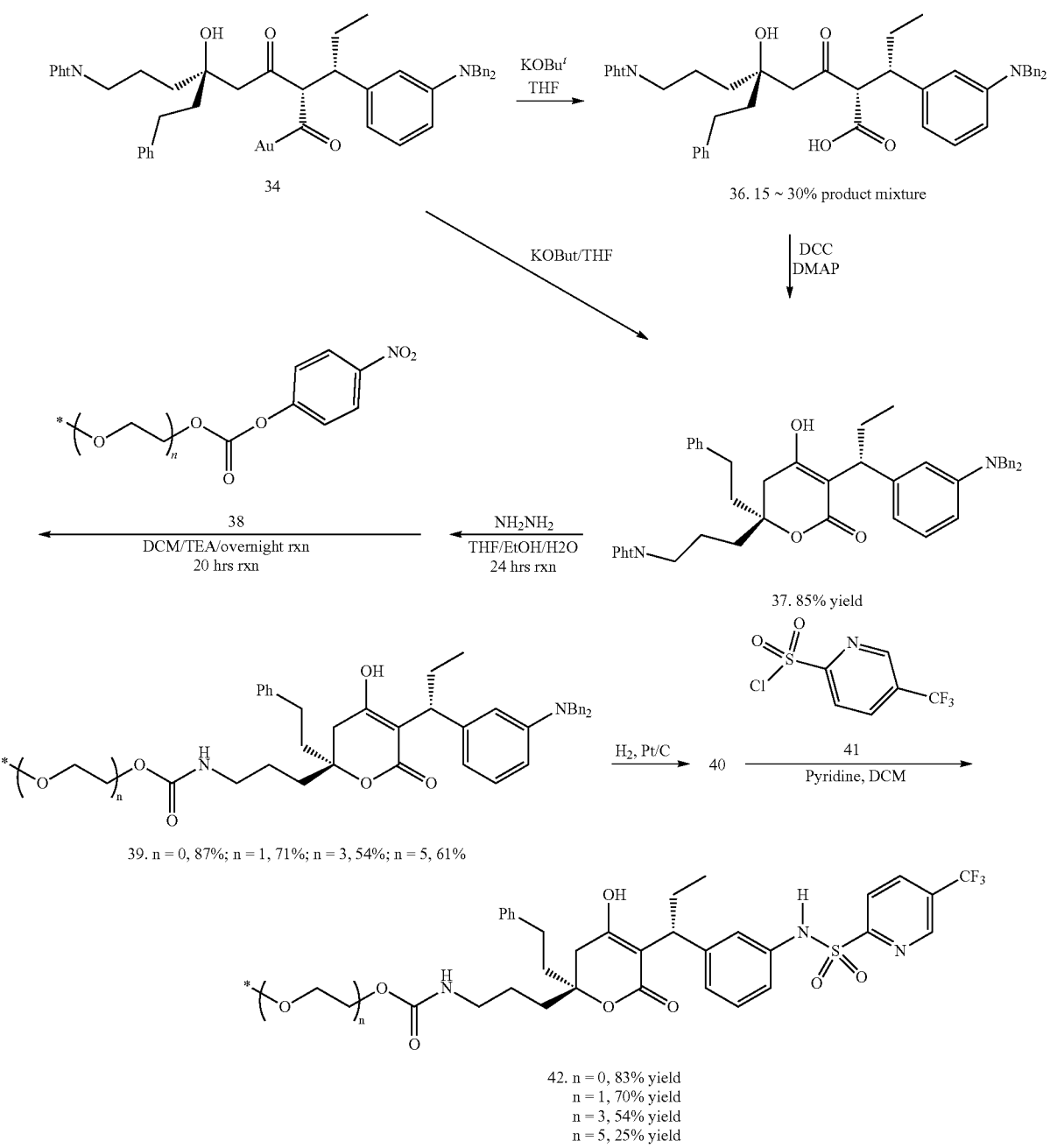

Basic Lactonization (2 Different Processes):

The starting material (34) (3.23 g, 3.66 mmol) was dissolved in THF (91 mL). The solution was cooled down to 0° C. in ice-water bath before KOBu$^t$ (1M, 4.21 mL, 4.21 mmol) was added. The reaction was kept at this temperature for 25 minutes and quenched with NH$_4$Cl aqueous solution (200 mL). EtOAc (200 mL) was added and the separated aqueous phase was extracted with EtOAc (50 mL×2). The combined organic phase was washed with brine (100 mL×2) and dried over Na$_2$SO$_4$. It was concentrated and the product mixture was performed DCC/DMAP lactonization without purification.

Lactonization Via DCC/DMAP:

The DCC/DMAP lactonization was applied based on the amount of free acid in the product mixture (36). The design was based on the hplc-UV detector in diluted solution (0.02 M). The DCC (6 eq of remaining free acid) and DMAP (25% of DCC) was added at ambient temperature. In general, this lactonization was accomplished in one hour and DCM was evaporated. The product residue was loaded on the Biotage column (40M, 15-48% EtOAc/Hex in 16 CV). The collected product (37) (1.82 g with 94% purity) and product mixture (858 mg, 59% purity) was obtained after high vacuo (84% total yield). R$_f$=0.10 (Hex:EtOAc=3:1), RP-HPLC (betasil C18, 0.5 mL/min, 30-100% ACN in 10 minutes) 5.16 minutes; LC-MS (ESI, MH$^+$) 718.3.

Phthalimide Deprotection:

The above lactone product (37) (507 mg, 0.705 mmol) was dissolved in THF (5.2 mL), EtOH (5.2 mL) and water (4 mL) was dropwise added until the solution start to be cloudy. NaHCO$_3$ (318 mg, 3 mmol) and NH$_2$NH$_2$ (342 μL, 7.05 mmol) was added. The reaction was kept at room temperature for six hours before another NH$_2$NH$_2$ (171 μL, 3.52 mmol) portion was added. After 23 hours, HPLC shows the starting material is less than 2%. The reaction was then stopped by adding NaHCO$_3$ (80 mL) and extracted with DCM (50 mL×3). The combined DCM solution was washed with brine and dried over Na$_2$SO$_4$. After filtration, it was concentrated and solidified during the high vacuo drying. The product residue was used in next step PEG conjugation without further purification. RP-HPLC (betasil C18, 0.5 mL/min, 30-100% ACN in 10 minutes) 6.50 minutes; LC-MS (ESI, MH$^+$) 589.3.

An approach for preparing mPEG carbonate (38) activation useful in the preparation of mPEGn-OCONH-Tripranavir conjugates is provided below.

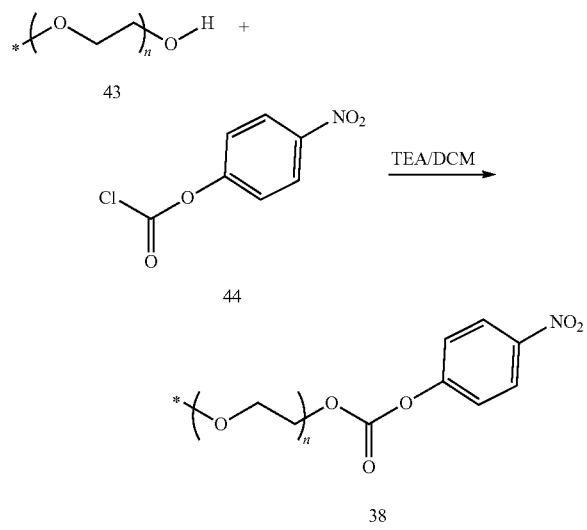

mPEG$_1$-4-nitrophenyl carbonate: In a 25-mL flask, 2-methoxyethanol (56 μL, 0.705 mmol) was added in DCM (5 mL). p-Nitrophenyl-chloroformate (44) (128 mg, 0.635 mmol) and TEA (147 μL, 1.06 mmol) was added. The reaction was kept at ambient temperature for 30 minutes. The DCM solution was concentrated to 3 mL in order to complete this reaction in next two hours. The reaction was stopped by addition of NH$_4$Cl (100 mL) and the product was extracted with DCM (30 mL×3). The combined DCM solution was dried over Na$_2$SO$_4$ and concentrated under the vacuo. The product (38) was used after high vacuo drying 10 minutes without further purification. RP-HPLC (betasil C18, 0.5 mL/min, 30-100% ACN in 10 minutes) 5.14 minutes.

mPEG$_0$-4-nitrophenyl carbonate: Methanol (10 eq), 4-nitropheyl chloroformate (1.1 eq), and TEA (1.5 eq). RP-HPLC (betasil C18, 0.5 mL/min, 30-100% ACN in 10 minutes) 4.84 minutes.

mPEG3-4-nitrophenyl carbonate: Substrate (0.439 mmol), 4-nitrophenyl-chloroformate (1.8 eq), and TEA (1.6 eq). RP-HPLC (betasil C18, 0.5 mL/min, 30-100% ACN in 10 minutes) 5.01 minutes; LC-MS (ESI, MH$^+$) 330.1.

mPEG$_5$-4-nitrophenyl carbonate: Substrate (0.439 mmol), 4-nitrophenyl-chloroformate (1.25 eq), and TEA (1.6 eq). RP-HPLC (betasil C18, 0.5 mL/min, 30-100% ACN in 10 minutes) 4.96 minutes; LC-MS (ESI, MH$^+$) 418.1. $^1$H NMR (500 MHz, CDCl$_3$) δ 3.38 (3H, s), 3.54-3.82 (18H, m), 4.43-4.45 (2H, m), 7.39 (2H, d, J=5.4 Hz), 8.28 (2H, d, J=5.4 Hz).

mPEG-Carbamate Conjugation mPEG$_1$-OCONH-core (39a): The product after phthalimide deprotecton (0.352 mmol) was dissolved in DCM (3 mL). The vacuo dried mPEG$_1$-p-nitrophenyl-carbonate (0.635 mmol) was transferred to the above solution with DCM (6 mL in total). TEA (147 μL, 1.05 mmol) was added and the reaction was kept at room temperature for 20 hours. After the reaction was completed, it was quenched with NH$_4$Cl aqueous solution and extracted with DCM (30 mL×3). The combined organic phase was dried over Na$_2$SO$_4$. After filtration, it was concentrated and the residue to loaded on Biotage column (25S, 20-75% of EtOAc in Hex in 16 CV). The desired product 39a was collected as the last portion and almost colorless product (172 mg) and a mixture (~16 mg, 71% yield in total) was collected. As a distereomeric mixture, $^1$H NMR cannot be read. R$_f$=0.15 (Hex: EtOAc=1:1), RP-HPLC (betasil C18, 0.5 mL/min, 30-100% ACN in 10 minutes) 8.65 minutes; LC-MS (ESI, MH$^+$) 691.2.

mPEG$_0$-OCONH-core (39b): Substrate (0.352 mmol), mPEG$_0$-p-nitrophenyl-carbonate (0.635 mmol), and TEA (147 μL). Biotage (25S, 20%-90% EtOAc in Hex in 16 CV). The colorless product (197 mg, 87% yield) and a mixture (30 mg) were collected. R$_f$=0.31 (Hex:EtOAc=1:1), RP-HPLC (betasil C18, 0.5 mL/min, 30-100% ACN in 10 min) 8.66 min; LC-MS (ESI, MH$^+$) 647.2.

mPEG3-OCONH-core (39c): Substrate (0.439 mmol), mPEG3-p-nitrophenyl-carbonate (0.702 mmol), and TEA (122 μL). Biotage (25S, 15-68% EtOAc in Hex in 16 CV). The colorless product (183 mg, 54% yield) was collected. R$_f$=0.55 (EtOAc), RP-HPLC (betasil C18, 0.5 mL/min, 30-100% ACN in 10 minutes) 8.27 minutes; LC-MS (ESI, MH$^+$) 779.5.

mPEG$_5$-OCONH-core (39d): Substrate (0.406 mmol), mPEG$_0$-p-nitrophenyl-carbonate (0.508 mmol), and TEA (113 μL). Biotage (25S, 15-68% EtOAc in Hex in 16 CV following by 2-7% MeOH in DCM in 16 CV). The colorless product (216 mg, 61% yield) and a mixture (29.5 mg) were collected. R$_f$=0.22 (EtOAc), RP-HPLC (betasil C18, 0.5 mL/min, 30-100% ACN in 10 minutes) 8.34 minutes; LC-MS (ESI, MH$^+$) 867.5.

Hydrogenolysis:

mPEG$_0$-OCONH-core-NH$_2$ (40a): The substrate (39a) mPEG$_0$-OCONH-core-NBn$_2$ (197.2 mg, 0.305 mmol) was dissolved in EtOAc (6.0 mL) and MeOH (6.0 mL) mixture solution. The solution vial was bubbling N$_2$ for exchange at lease 15 minutes before catalyst addition. Stop stirring, and the Pd/C catalyst (39 mg, 10 wt %×2) was added slowly. The system was evacuated and recharged with hydrogen gas (~50 psi) three times (stop stirring during vacuo). The hydrogenolysis was then kept at room temperature under 50 psi for 24 hrs to complete. After release the pressure, the reaction mixture was first checked with HPLC to see the completeness before a filtration was performed. The catalyst residue and filter paper was carefully washed with methanol. The solution was then evaporated and vacuo drying to give oil-like product (145.3 mg, >100% yield). No further purification is necessary. No proton NMR due to the diastereoisomer mixture and low solubility in CHCl$_3$. RP-HPLC (betasil C18, 0.5 mL/min, 20-60% ACN in 10 minutes) 7.03+7.44 minutes, LC-MS (ESI, MH$^+$) 467.3.

mPEG$_1$-OCONH-core-NH$_2$ (40b): RP-HPLC (betasil C18, 0.5 mL/min, 20-600% ACN in 10 minutes) 6.89+7.18 minutes; LC-MS (ESI, MH$^+$) 511.3.

mPEG₃-OCONH-core-NH₂ (40c): RP-HPLC (betasil C18, 0.5 mL/min, 20-60% ACN in 10 minutes) 7.20+7.43 minutes; LC-MS (ESI, MH⁺) 599.3.

mPEG₅-OCONH-core-NH₂ (40d): RP-HPLC (betasil C18, 0.5 mL/min, 30-100% ACN in 10 minutes) 4.05+4.29 minutes; LC-MS (ESI, MH⁺) 687.4.

Sulphonate Amide Conjugation:

mPEG₃-OCONH-Tipranavir-2 (42c): The free amine mPEG₃-OCONH-core-NH₂ (40c) (67.3 mg, 0.112 mmol) was dissolved in DCM (3.0 mL) under N₂ protection. After dissolving, the solution was cool down in an ice-water bath and sulphonyl chloride (27 mg, 0.112 mmol) was added. Pyridine (18 μL, 0.224 mmol) was then added and the reaction was kept at 0° C. for 30 minutes. Methyl amine (2M, 500 μL, 1.0 mmol) was added and the reaction was kept at this temperature for three hours. After HPLC show the reaction was completed, it was quenched with NH₄Cl (10 mL) and diluted with DCM and H₂O. The separated organic phase was washed with brine (10 mL×2). The organic phase was then dried over Na₂SO₄, filtrated, and concentrated. The crude product was purified on Biotage (40-90% EtOAc in Hex in 16 CV) provided a slightly yellowish solid product (42.6 mg) and a less pure product (6.6 mg) with the total yield about 54%. Proton NMR cannot read due to its diastereomer mixture. Isomer ratio=54/41. $R_f$=0.37 (EtOAc), RP-HPLC (betasil C18, 0.5 mL/min, 60-100% ACN in 8 minutes) 7.16+7.28 minutes; LC-MS (ESI, MH⁺) 808.3.

mPEG₀-OCONH-Tipranavir-2 (42a): The free amine mPEG₀-OCONH-core-NH₂ 40a (71.7 mg, 0.154 mmol), sulphonyl chloride (37.0 mg, 0.154 mmol), Pyridine (25 μL, 0.308 mmol). Biotage (20-80% EtOAc in Hex in 16 CV) provided a slightly yellowish solid product (51.5 mg). Isomer ratio=55/43. $R_f$=0.12 (Hex:EtOAc=1:1), RP-HPLC (betasil C18, 0.5 mL/min, 30-100% ACN in 10 minutes) 7.51+7.61 minutes; LC-MS (ESI, MH⁺) 676.2.

mPEG₁-OCONH-Tipranavir-2 (42c): The free amine mPEG₁-OCONH-core-NH₂ 40c (62.0 mg, 0.122 mmol), sulphonyl chloride (31.0 mg, 0.128 mmol), Pyridine (20 μL, 0.244 mmol). Biotage (25-90% EtOAc in Hex in 16 CV) provided a slightly yellowish solid product. Isomer ratio=58/40. $R_f$=0.06 (Hex:EtOAc=1:1); 0.72 (EtOAc), RP-HPLC (betasil C18, 0.5 mL/min, 30-100% ACN in 10 minutes) 7.49+7.60 minutes; LC-MS (ESI, MH⁺) 720.3.

mPEG₅-OCONH-Tipranavir-2 (42d): The free amine mPEG₅-OCONH-core-NH₂ 42d (156 mg, 0.227 mmol), sulphonyl chloride (64.0 mg, 0.254 mmol), Pyridine (42 μL, 0.254 mmol). Biotage (1-7% MeOH in DCM in 16 CV) provided a slightly yellowish solid product. Isomer ratio=56/41. $R_f$=0.06 (EtOAc), RP-HPLC (betasil C18, 0.5 mL/min, 30-100% ACN in 10 minutes) 7.26+7.37 minutes; LC-MS (ESI, MH⁺) 918.3.

Example 1

In Vitro Pharmacology

Enzyme Inhibition of Purified HIV-1 Protease

Protease inhibitors (PI) are used to treat HIV infection by preventing viral assembly and maturation through the inhibition of HIV-1 protease activity. Biochemical assays were performed to evaluate the potential of PEG-PI conjugates to inhibit HIV-1 protease activity, relative to their respective PI parent molecules. Activity assays were performed at using the SensoLyte 520 HIV-Protease Assay Kit (Anaspec Inc., San Jose, Calif.) and recombinant HIV-1 protease. Protease activity was monitored by the formation of a fluorescent reporter product generated during HIV-1 protease-mediated digestion of a quenched, fluorimetric substrate containing the p17/p24 Pr$^{gag}$ cleavage site. The results are summarized in Table 1.

TABLE 1

Inhibition Constants for HIV-1 Protease

| Compound | $IC_{50}$ ± SD (nM) |
|---|---|
| Atazanavir | 6.92 |
| (repeated tests) | 5.120 |
| | 7.601 ± 2.000 |
| | 7.366 ± 2.751 |
| | 1.553 |
| di-mPEG3-Atazanavir | 12.72 |
| (repeated tests) | 6.358 ± 2.474 |
| di-mPEG5-Atazanavir | 17.33 |
| di-mPEG6-Atazanavir | 15.63 |
| di-mPEG7-Atazanavir | 10.92 |
| mono-mPEG1-Atazanavir | 2.816 |
| mono-mPEG3-Atazanavir | 0.366 |
| (repeated tests) | 4.937 ± 3.588 |
| | 3.095 |
| mono-mPEG5-Atazanavir | 2.909 |
| mono-mPEG6-Atazanavir | 1.306 |
| mono-mPEG7-Atazanavir | 1.287 |
| Darunavir | 1.5 |
| (repeated tests) | 3.981 ± 1.259 |
| mPEG3-N-Darunavir | 5.3 |
| mPEG5-N-Darunavir | 1.1 |
| (repeated tests) | 3.841 ± 1.319 |
| mPEG7-N-Darunavir | 5.2 |
| (repeated tests) | 4.914 ± 1.410 |
| mPEG3-O-Darunavir | 0.475 |
| (repeated tests) | 4.588 ± 1.712 |
| mPEG5-O-Darunavir | 0.210 |
| (repeated tests) | 4.419 ± 2.667 |
| mPEG7-O-Darunavir | 0.358 |
| (repeated tests) | 3.620 ± 1.560 |
| Tipranavir | 7.2 |
| (repeated tests) | 1.957 |
| mPEG3-amide-Tipranavir | — |
| mPEG5-amide-Tipranavir | — |
| mPEG7-amide-Tipranavir | 12.2 |
| mPEG0-OCO—NH-Tipranavir | 0.292 |
| mPEG1-OCO—NH-Tipranavir | 0.188 |
| mPEG3-OCO—NH-Tipranavir | 0.617 |
| mPEG5-OCO—NH-Tipranavir | 0.462 |
| Saquinavir | 0.05 |
| (repeated tests) | 5.452 ± 2.410 |
| mPEG3-NHCO-Saquinavir | 0.07 |
| (repeated tests) | 4.321 ± 0.511 |
| mPEG5-NHCO-Saquinavir | 0.05 |
| (repeated tests) | 5.743 ± 2.097 |
| mPEG7-NHCO-Saquinavir | 0.05 |
| (repeated tests) | 4.177 ± 4.479 |
| Indinavir | 10.526 |

The $IC_{50}$ data reveal that PEG-modified PI compounds generally retained the ability to inhibit HIV-1 protease activity at levels comparable to that observed with their respective parent molecules and within nanomolar range $IC_{50}$ values that confirm significant inhibition of the purified HIV-1 protease. Interestingly, mono-mPEG3-ATZ displayed an increase in potency against HIV-1 protease compared to atazanavir.mono-mPEG(n)atazanavir, for n=1, 3, 5, 6, 7, displayed comparable or greater potency than the unconjugated atazanavir in this assay.

Cytoprotection in CEM-SS Cells Infected with HIV-1$_{RF}$

To evaluate whether conjugated protease inhibitors retain the ability to protect against HIV-1 infection, CEM-SS cells infected with the RF strain of HIV-1 were treated with test compounds for six days, and then cell viability was monitored using the tetrazolium dye XTT. Infection studies were performed and $EC_{50}$ values were calculated as the protease inhibitor concentration leading to 50% reduction in cell death compared to virus-infected cells without protease inhibitor. $TC_{50}$ values were calculated as the protease inhibitor concentration leading to 50% cell death in the absence of viral infection. A value for Therapeutic Index (TI) was calculated as $TC_{50}/EC_{50}$. In an initial experiment, saquinavir and mPEGn-NHCO-saquinavir were tested at a concentration range that was too high for $IC_{50}$ determination, so a second study was performed using a more appropriate concentration range. The results are summarized in Table 2.

The data demonstrate that for the majority of compounds, PEG conjugation led to a decrease in activity in the cell-based CEM-SS assay. By contrast, mono-mPEGatazanavir conjugates containing PEG sizes 1, 3, 5 and 6, demonstrated an approximate 10-fold increase in activity in the same assay compared with atazanavir, whereas mono-mPEG(7)atazanavir displayed comparable activity In several cases a PEG size-dependent loss in activity was observed; thus 5 and 7 ethylene glycol units in the compounds mPEG5-amide-tipranavir and mPEG7-amide-tipranavir effectively elimi-

TABLE 2

Activity of Compounds in Anti-HIV Cytoprotection Assay

| Compound | CEM-SS/ HIV-1$_{RF}$ EC$_{50}$ ± SD (μM) | CEM-SS TC$_{50}$ ± SD (μM) | TI |
|---|---|---|---|
| Atazanavir | 0.012 | 54.9 | 4578 |
| (repeated tests) | 0.036 | 71.2 | 1977 |
| | 0.015 ± 0.014 | 54.03 ± 16.78 | 3602 |
| | 0.021 ± 0.015 | 65.70 ± 30.15 | 3128 |
| | 0.015 ± 0.01 | 80.1 ± 15.2 | 7627.4 |
| | 0.0002 | >25.0 | >107758.6 |
| di-mPEG3-Atazanavir | 0.038 | 95.7 | 2519 |
| (repeated tests) | 0.12 ± 0.0058 | 96.3 ± 16.83 | 802.5 |
| di-mPEG5-Atazanavir | 1.11 | >200.0 | >181 |
| di-mPEG6-Atazanavir | 2.54 | 158.6 | 62.4 |
| di-mPEG7-Atazanavir | 8.35 | >200.0 | >24 |
| mono-mPEG1-Atazanavir | 0.002 ± 0.0006 | 49.1 ± 6.4 | 21432.3 |
| mono-mPEG3-Atazanavir | 0.003 | 90.7 | 30228 |
| (repeated tests) | <0.00066 | 72.53 ± 11.20 | >110000 |
| | 0.005 ± 0.001 | | |
| | 0.003 ± 0.002 | 114.8 ± 18.1 | 41198.6 |
| | 0.00057 | >25.0 | >44091.7 |
| mono-mPEG5-Atazanavir | 0.001 ± 0.0006 | 82.2 ± 4.4 | 68024. |
| | 0.001 | 113.3 | 113338.0 |
| mono-mPEG6-Atazanavir | 0.002 ± 0.0006 | 81.1 ± 6.0 | 36428.1 |
| | 0.012 | 110.1 | 9172.8 |
| mono-mPEG7-Atazanavir | 0.03 ± 0.02 | 133.8 ± 24.5 | 9146.4 |
| Darunavir | <0.0007 | 118.8 | >169714 |
| (repeated tests) | <0.00066 | 114.07 ± 6.17 | >172833 |
| | 0.001 ± 0.0009 | >0.5 | >500 |
| mPEG3-N-Darunavir | <0.0007 | 93.9 | >13414 |
| mPEG5-N-Darunavir | 0.011 | 40.7 | 3700 |
| (repeated tests) | 0.0047 ± 0.0021 | 30.53 ± 1.32 | 6496 |
| mPEG7-N-Darunavir | 0.014 | 167.6 | 11971 |
| (repeated tests) | 0.011 ± 0.00058 | 120.33 ± 20.28 | 10939 |
| mPEG3-O-Darunavir | 0.009 | >200.0 | >22222 |
| (repeated tests) | 0.001 ± 0.000 | 121.67 ± 10.26 | 121670 |
| mPEG-5-O-Darunavir | 0.019 | >200.0 | >10526 |
| (repeated tests) | 0.009 ± 0.002 | 146.03 ± 6.69 | 16226 |
| mPEG7-O-Darunavir | 0.047 | >200.0 | >4255 |
| (repeated tests) | 0.076 ± 0.044 | 155.70 ± 37.76 | 2049 |
| Tipranavir | 0.12 | 30.6 | 255 |
| (repeated tests) | 0.039 | 40.7 | 1042 |
| mPEG3-amide-Tipranavir | 0.08 | 1.3 | 16.25 |
| mPEG5-amide-Tipranavir | >200 | 12.8 | <0.064 |
| mPEG7-amide-Tipranavir | >200 | 14.5 | <0.0725 |
| mPEG0-OCO—NH-Tipranavir | 0.29 | 54.3 | 184.6 |
| mPEG1-OCO—NH-Tipranavir | 0.12 | 49.5 | 409.1 |
| mPEG3-OCO—NH-Tipranavir | 0.87 | 67.6 | 77.6 |
| mPEG5-OCO—NH-Tipranavir | 1.06 | 86.1 | 81.6 |
| Saquinavir | 0.006 | >0.1 | >16.6 |
| (repeated tests) | 0.00022 ± 0.00004 | 11.6 ± 1.11 | 52727 |
| mPEG3-NHCO-Saquinavir | 0.02 | >0.1 | >5.0 |
| (repeated tests) | <0.00017 | 18.03 ± 1.42 | >10606 |
| | 0.007 ± 0.001 | | |
| mPEG5-NHCO-Saquinavir | 0.02 | >0.1 | >5 |
| (repeated tests) | 0.00039 ± 0.00002 | 13.57 ± 5.80 | 34795 |
| mPEG7-NHCO-Saquinavir | 0.04 | >0.1 | >2.5 |
| (repeated tests) | 0.0043 ± 0.0023 | 25.17 ± 3.71 | 5853 |
| AZT | 0.004 ± 0.0006 | >1.0 ± 0.0 | >200. |

HIV-1 protease is generated in the cytoplasm of infected host cells, therefore protease inhibitors must cross cell membranes to reach their target and inhibit viral maturation.

nated the ability of tipranavir to protect CEM-SS cells against HIV-1 infection whereas mPEG3-amide-Tipranavir exhibited relatively strong cytoprotective properties.

Effects of Pre- and Post-Infection PI Treatment on CEM-SS Toxicity

The effects of pre- and post-infection PI treatment on CEM-SS toxicity were assessed. In pre-exposure assays, where compound was present prior to HIV-1 infection, CEM-SS cells were treated for 2, 8, or 24 hours with various concentrations of saquinavir or mPEG7-NHCO-Saquinavir, washed free from drug, then infected with HIV-1$_{RF}$ in the absence of test compounds. Cell toxicity was monitored six days after infection using XTT reagent. In the post-exposure assay, test compounds were added to cells 0, 24, 48, or 72 h after HIV-1 infection, and cell viability was measured six days post-infection. Control compounds run in parallel with test protease inhibitors included an entry inhibitor, Chicago Sky Blue, as well as the nucleoside reverse transcriptase inhibitor, azidothymidine (AZT), a non-nucleoside reverse transcriptase inhibitor, nevirapine, and the protease inhibitor, ritonavir.

Pre-treatment of cells with Chicago Sky Blue did not demonstrate antiviral activity at concentrations up to 10 µg/mL, whereas AZT, nivirapine, and ritonavir all exhibited sub-micromolar $EC_{50}$ values. Saquinavir yielded similar $EC_{50}$ values ≤0.05 µM at each pre-treatment time (Table 3). The mPEG-7-NHCO-Saquinavir conjugate was at least 9-fold less potent in protecting CEM-SS cells from HIV toxicity than saquinavir following pre-treatment, however this PEG-derivative exhibited similar potency to the marketed protease inhibitor, ritonavir, in the cell protection assay. There was no difference in the level of cytoprotection observed in response to saquinavir or mPEG$_7$-NHCO-Saquinavir whether cells were pre-treated for 2, 8, or 24 hours prior to HIV infection.

TABLE 3

Effect of Time of Addition of PI or PEG-PI on HIV$_{RF}$-Infection in CEM-SS Cells as Measured by Cell Viability (Efficacy and Toxicity Values Derived From Treatment of CEM-SS Cells With Test Compounds For Various Times Prior to HIV-1 Infection)

| Time of exposure pre-infection | Chicago Sky Blue | | | Nevirapine | | | AZT | | | Ritonavir | | | SQV | | | mPEG7-NHCO-SQV | | |
|---|---|---|---|---|---|---|---|---|---|---|---|---|---|---|---|---|---|---|
| | $EC_{50}$ (µg/ml) | $TC_{50}$ (µg/ml) | TI | $EC_{50}$ (µM) | $TC_{50}$ (µM) | TI | $EC_{50}$ (µM) | $TC_{50}$ (µM) | TI | $EC_{50}$ (µM) | $TC_{50}$ (µM) | TI | $EC_{50}$ (µM) | $TC_{50}$ (µM) | TI | $EC_{50}$ (µM) | $TC_{50}$ (µM) | TI |
| 2 h | >10.0 | >10.0 | — | 0.47 | >1.0 | >2.1 | 0.16 | >1.0 | >6.3 | 0.72 | >1.0 | >1.4 | 0.02 | >1.0 | >50.0 | 0.5 | >1.0 | >2.0 |
| 8 h | >10.0 | >10.0 | — | 0.20 | >1.0 | >5.0 | 0.36 | >1.0 | >2.8 | 0.75 | >1.0 | >1.3 | 0.05 | >1.0 | >20.0 | 0.54 | >1.0 | >1.9 |
| 24 h | >10.0 | >10.0 | — | 0.64 | >1.0 | >1.6 | 0.13 | >1.0 | >7.7 | 0.68 | >1.0 | >1.5 | 0.04 | >1.0 | >25.0 | 0.74 | >1.0 | >1.4 |

During post-infection experiments, where compound was added to cells 0, 24, 48, or 72 hours after HIV-1 infection, saquinavir demonstrated significant antiviral activity regardless of the time it was added to cells, albeit with reduced potency when addition was delayed to 72 hours post-infection (Table 4). The mPEG7-Saquinavir conjugate yielded similar $EC_{50}$ values at all exposure times, although was generally less potent than saquinavir. AZT and nevirapine demonstrated significant antiviral activity when added 24 hours after HIV exposure that decreased with each day the addition of compounds was delayed. In contrast, Chicago Sky Blue was efficacious only when added at the time of HIV-infection and had no effect when added at later times.

TABLE 4

Effect of Time of Addition of PI or PEG-PI on HIV$_{RF}$-Infection in CEM-SS Cells as Measured by Cell Viability (Efficacy and Toxicity Values Derived From Treatment of CEM-SS Cells With Test Compounds at Various Times Post-HIV-1 Exposure)

| Time of drug addition post-infection | Chicago Sky Blue | | | Nevirapine | | | AZT | | | Ritonavir | | | SQV | | | mPEG7-NHCO-SQV | | |
|---|---|---|---|---|---|---|---|---|---|---|---|---|---|---|---|---|---|---|
| | $EC_{50}$ (µg/mL) | $TC_{50}$ (µg/mL) | TI | $EC_{50}$ (µM) | $TC_{50}$ (µM) | TI | $EC_{50}$ (µM) | $TC_{50}$ (µM) | TI | $EC_{50}$ (µM) | $TC_{50}$ (µM) | TI | $EC_{50}$ (µM) | $TC_{50}$ (µM) | TI | $EC_{50}$ (µM) | $TC_{50}$ (µM) | TI |
| 0 h | 1.84 | 8.2 | 4.5 | 0.005 | >1.0 | >200.0 | 0.006 | >1.0 | >167.0 | 0.04 | >1.0 | >25.0 | <0.003 | >1.0 | >333.0 | 0.05 | >1.0 | >20.0 |
| 24 h | >10.0 | 4.9 | — | 0.01 | >1.0 | >100.0 | 0.02 | >1.0 | >50.0 | 0.03 | >1.0 | >33.3 | 0.004 | >1.0 | >250.0 | 0.05 | >1.0 | >20.0 |
| 48 h | >10.0 | 5.5 | — | 0.05 | >1.0 | >20.0 | 0.21 | >1.0 | >4.8 | 0.07 | >1.0 | >14.3 | 0.005 | >1.0 | >200.0 | 0.05 | >1.0 | >20.0 |
| 72 h | >10.0 | 5.6 | — | 0.2 | >1.0 | >5.0 | >1.0 | >1.0 | — | 0.26 | >1.0 | >3.9 | 0.01 | >1.0 | >100.0 | 0.09 | >1.0 | >11.1 |

These findings are in agreement with previously described findings demonstrating reduced cytoprotection by PEG-Saquinavir conjugates during HIV-1-infection in CEM-SS cells when compared to saquinavir (see Table 2).

Figure 1B:
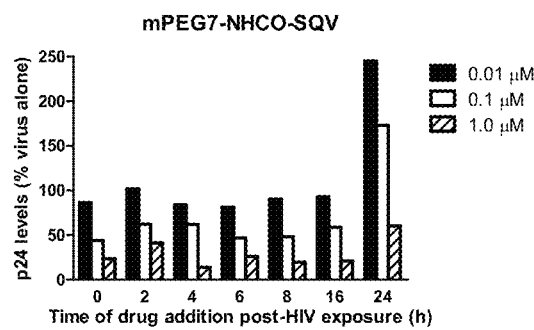
Figure 1C:
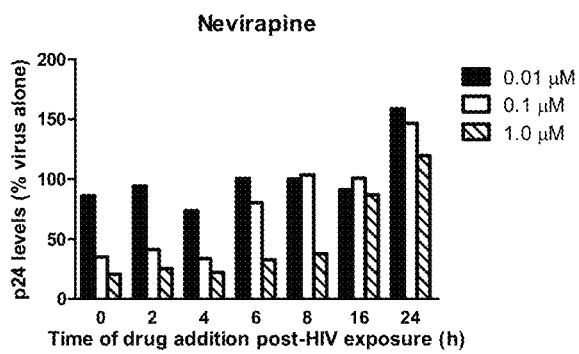
Figure 1D:
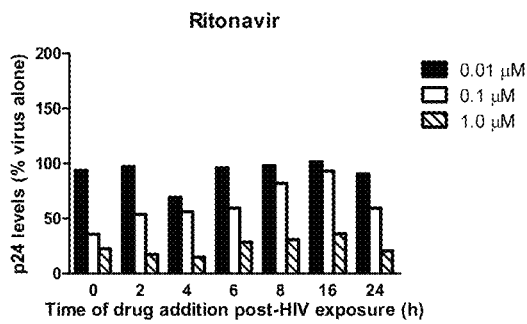
Figure 1E:
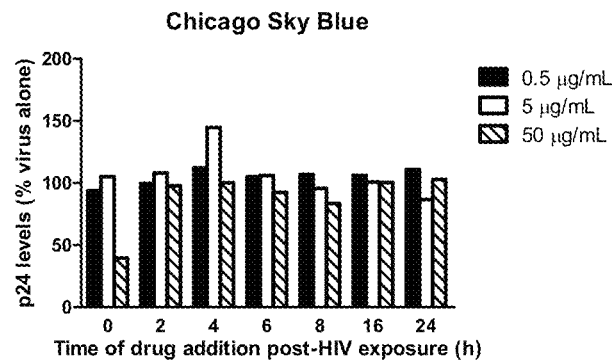
Figure 2A:
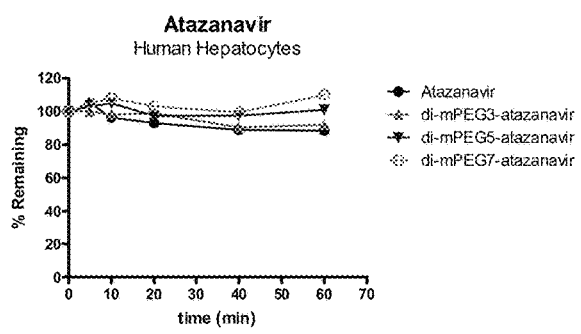
FIGS. 2A-2D are graphs comparing the metabolic stability of $PEG_{oglio}$-protease inhibitor conjugates and protease inhibitor molecules following incubation with cryopreserved human hepatocytes, as further described in Example 2. Values were obtained using 3 µM test compound concentration.
Figure 2B:
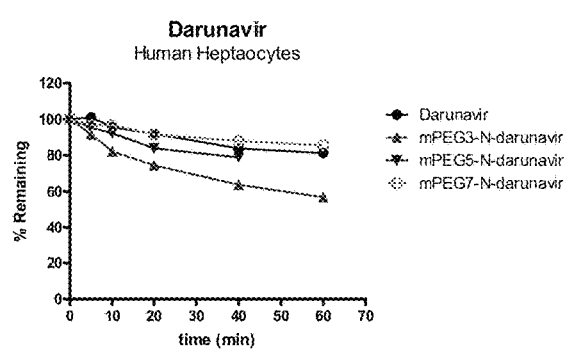
Figure 2C:
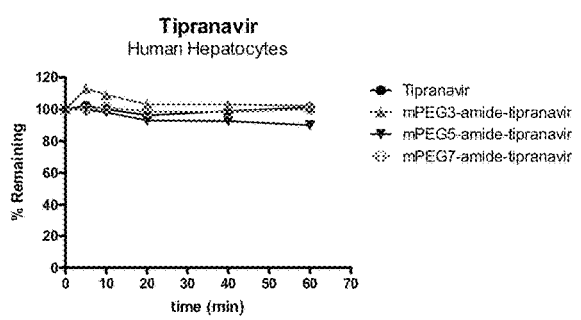
Figure 2D:
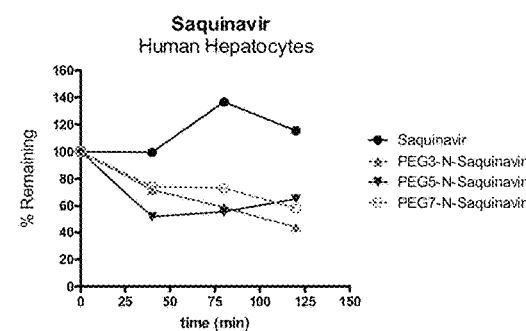

Effect of PEG-PI Compounds on Viral Replication During High Multiplicity of Infection CEM-SS Cells The cytoprotective effect against HIV of the PEG-protease inhibitor conjugates was evaluated during a single round of high multiplicity of infection ("MOI") HIV-1 infection in CEM-SS cells. CEM-SS cells were incubated for one hour with a single high MOI dose of HIV-1$_{RF}$. Cells were washed to remove free virus, then test compounds were added to cells at 0, 2, 4, 6, 8, 16, or 24 hours after HIV-1 infection. To monitor viral replication, cell supernatants were analyzed at 30 hours post-infection for levels of the HIV capsid protein p24 (FIG. 1). Saquinavir and mPEG$_7$-NHCO-Saquinavir demonstrated similarly potent antiviral activity at 0.1 µM when added up to 16 hours post-infection, and at 1 µM when added up to 24 hours post-infection, as evidenced by reduced p24 expression in comparison to virus-alone controls. Chicago Sky Blue did not affect p24 levels when added to cells at any time after HIV-infection, even at 50 µg/mL. Nevirapine inhibited viral replication at 1 µM when added to cells up to four hours post-infection, and at 10 µM when added up to eight hours post-infection. Ritonavir also exhibited antiviral activity at 0.1 and 1 µM up to six and 24 hours post-infection, respectively.

In concert with p24 analysis, cell supernatants collected from cells exposed to test compounds at 8, 16, or 24 hours post-infection were used to infect naïve CEM-SS cells. Cell viability was measured six days post-infection as a measure of virus infectivity (Table 5).

gradient. Viable cells were induced to proliferate in the presence of PHA-P and recombinant human IL-2 for 72 hours. PBMCs pooled from three donors were cultured with test compounds in the presence of the HT/92/599 clinical subtype B HIV-1 for seven days, followed by measurement of reverse transcriptase activity in cell supernatants using a radioactive incorporation polymerization assay. Cell supernatant containing HIV-1 viral was incubated for 90 minutes at 37° C. with a reaction mixture containing EGTA, Triton X-100, Tris (pH 7.4), DTT, MgCl$_2$, poly rA, oligo dT, and tritiated thymidine triphosphate (TTP). Incorporation of TTP into DNA was monitored by spotting the reaction mixture onto a DEAE filter mat, followed by washes with 5% phosphate buffer, distilled water, and 70% ethanol, and subsequent drying of the mat. Radioactivity was measured using a Wallac 1450 Microbeta Trilux liquid scintillation counter using Opti-Fluor O. Test compound-associated toxicity was measured in PBMCs cultured for seven days in the absence of virus using XTT reagent. Saquinavir and mPEG5-NHCO— and mPEG7-NHCO-Saquinavir conjugates were protective against HIV-1, yielding EC$_{50}$ values of 0.009, 0.02, and 0.12 µM, respectively (Table 6). The test compounds did not alter viability of PBMCs at test concentrations up to 1 µM. TI was calculated as TC$_{50}$/EC$_{50}$.

TABLE 5

Percent Infectivity of HIV-1 Virions Generated Following Addition of Test Compounds at Various Times After HIV-1 Infection in Comparison to Virus-Alone Control as Measured by Viability in CEM-SS Cells.

| Time of drug addition | Chicago Sky Blue | | | Nevirapine | | | Ritonavir | | | SQV | | | mPEG7-NHCO-SQV | | |
|---|---|---|---|---|---|---|---|---|---|---|---|---|---|---|---|
| post-infection | 0.5 µg/mL | 5 µg/mL | 50 µg/mL | 0.1 µM | 1 µM | 10 µM | 0.01 µM | 0.1 µM | 1 µM | 0.01 µM | 0.1 µM | 1 µM | 0.01 µM | 0.1 µM | 1 µM |
| 8 h | 100.0 | 100.0 | 100.0 | 100.0 | 100.0 | 10.0 | 42.9 | 1.0 | 0.1 | 100.0 | 5.6 | 0.1 | 117.0 | 0.1 | 0.1 |
| 16 h | 177.8 | 331.2 | 562.3 | 117.0 | 100.0 | 177.8 | 331.2 | 3.7 | 0.1 | 117.0 | 10.0 | 7.8 | 177.8 | 37.0 | 1.4 |
| 24 h | 266.4 | 100.0 | 100.0 | 128.0 | 177.8 | 177.8 | 100.0 | 26.6 | 0.1 | 404.8 | 128.0 | 12.8 | 100.0 | 266.4 | 10.0 |

The infectivity of virions collected from cells exposed to 0.1 or 1 µM SQV at 8 and 16 hours post-infection was reduced by at least 90% when compared to virus-only control cells. Additionally, virus produced by cells exposed to 1 µM saquinavir at 24 hours post-infection exhibited nearly 90% reduction in infectivity compared to virus-only controls. Cells treated with 0.1 µM mPEG7-NHCO-SQV at 8 or 16 hours post-infection reduced virus infectivity to 63 and 99.9% of virus-alone controls, respectively, while 1 µM mPEG7-NHCO-Saquinavire treatment reduced infectivity ≥90% when added up to 24 hours post-infection.

Effect of PEG-PI Compounds on Viral Replication in Human Peripheral Blood Mononuclear Cells and Monocytes Fresh human peripheral blood mononuclear cells (PBMCs) obtained from a commercial source were purified following centrifugation using a Ficoll-Hypaque density

TABLE 6

Effect of Test Compounds on HIV-1 Reverse Transcriptase Activity Following Infection in Fresh Human PBMCs

| Compound | PBMC/HIV-1$_{HT/92/599}$ EC$_{50}$ ± SD (µM) | PBMC TC$_{50}$ ± SD (µM) | TI |
|---|---|---|---|
| Atazanavir | 0.025 ± 0.006 | 114.5 | 4580 |
| (repeated tests) | 0.033 ± 0.006 | 129.4 | 3921 |
| | 0.113 ± 0.009 | >0.5 | >4.4 |
| | 0.00294 ± 0.00889 | >1.0 | >340.1 |
| | <0.02 | 166.4 | >8320 |
| | 0.002 | >1.0 | >500.0 |
| di-mPEG3-Atazanavir | 0.39 ± 0.06 | 146 | 374 |
| mono-mPEG1-Atazanavir | <0.02 | 135.9 | >6795 |
| mono-mPEG3-Atazanavir | <0.02 | 109.7 | >5485 |
| (repeated tests) | 0.03 ± 0.00 | >0.5 | >16.7 |
| | 0.02037 ± 0.004522 | >1.0 | >49.1 |
| | 0.02 | >1.0 | >50.0 |
| | 0.0187 ± 0.0099 | >1.0 | >53.5 |

TABLE 6-continued

Effect of Test Compounds on HIV-1 Reverse Transcriptase
Activity Following Infection in Fresh Human PBMCs

| Compound | PBMC/HIV-$1_{HT92/599}$ EC$_{50}$ ± SD (µM) | PBMC TC$_{50}$ ± SD (µM) | TI |
|---|---|---|---|
| mono-mPEG5-Atazanavir | 0.05343 ± 0.0113 | >1.0 | >18.7 |
| (repeated tests) | 0.0533 ± 0.0055 | 147.7 | 2771 |
|  | 0.02 | >10.0 | >500.0 |
| mono-mPEG6-Atazanavir | 0.1085 ± 0.036314 | >1.0 | >9.2 |
| (repeated tests) | 0.1167 ± 0.0055 | 146.0 | 1251 |
|  | 0.06 | >10.0 | >166.67 |
| mono-mPEG7-Atazanavir | 0.1633 ± 0.03 | 187.2 | 1146 |
| Darunavir | <0.02 | 189.8 | >9490 |
| (repeated tests) | 0.009 ± 0.001 | >0.5 | >55.6 |
| mPEG5-N-Darunavir | <0.02 | 71.6 | >3580 |
| (repeated tests) | 0.033 ± 0.005 | >0.5 | >15.2 |
| mPEG7-N-Darunavir | 0.073 ± 0.012 | >200 | >2740 |
| mPEG3-O-Darunavir | 0.027 ± 0.006 | >200 | >7407 |
| mPEG-5-O-Darunavir | 0.09 ± 0.008 | >200 | >2222 |
| mPEG7-O-Darunavir | 0.25 ± 0.027 | >200 | >800 |
| Saquinavir | 0.009 | >1.0 | >111.1 |
| (repeated tests) | <0.02 | 12.5 | >625 |
|  | 0.023 ± 0.006 | >0.5 | >21.7 |
| mPEG3-NHCO-Saquinavir | <0.02 | 31.5 | >1575 |
| (repeated tests) | 0.053 ± 0.011 | >0.5 | >9.43 |
| mPEG5-NHCO-Saquinavir | 0.02 | >1.0 | >50.0 |
| (repeated tests) | <0.02 | 30.7 | >1503 |
|  | 0.036 ± 0.026 | >0.5 | >13.9 |
| mPEG7-NHCO-Saquinavir | 0.12 | >1.0 | >8.3 |
| (repeated tests) | 0.073 ± 0.022 | 53.6 | 734 |

Mononuclear cells were isolated from fresh human peripheral blood cells by Ficoll-Hypaque density gradient by centrifugation at 600 g for 30 minutes. Banded peripheral blood mononuclear cells (PBMCs) were aspirated from the resulting interface and washed with phosphate buffered saline by low speed centrifugation. Viable cells were diluted to 4×106 cells/mL in Hanks Balanced Salt Solution with 10% heat-inactivated human AB serum, then 100 L of the cell suspension was plated to individual wells of a 96-well flat-bottom plate. Cells were allowed to attach for 2 to 12 h at 37° C., then washed with Dulbecco's phosphate buffered saline (DPBS). Monocyte-macrophage monolayer formation was induced by incubation in growth medium (RPMI 1640 medium supplemented with 10% fetal bovine serum, 2 mmol/L L-glutamine, 100 Units/mL penicllin and 10 µg/mL streptomycin) for 7 days. Residual PBMCs were removed by washing the cell monolayers with DPBS. After washing, test compound diluted in growth medium was added to cells. Immediately following test compound addition, HIV-1 virus was added to the cells at multiplicity of infection (MOI)= 0.05-0.10. After 7 days in culture, HIV-1 replication was quantified by ELISA measurement of cell-free HIV-1 viral capsid protein (p24) in the tissue culture supernatant of treated monocyte-macrophage monolayers. ELISA to quantify p24 was performed according to manufacturer's instructions (Perkin Elmer, Waltham, Mass.). The quantity of free HIV-1 p24 antigen in the sample was determined by comparing its absorbance at 490 nm to that of control standards.

Fresh human monocytes were infected with the BaL strain of HIV-1 in the presence of test compounds. After seven days in culture, HIV-1 replication was evaluated by measurement of HIV-1 viral capsid protein (p24) in the tissue culture supernatant (Table 7). Saquinavir and both PEG-Saquinavir conjugates demonstrated antiviral activity, although a PEG-size dependent increase in EC$_{50}$ values was observed. Likewise, darunavir conjugates demonstrated fairly strong potency, albeit somewhat lower than that of the unconjugated darunavir. However, as seen in the earlier tests, PEG-atazanavir displayed increased potency compared with unconjugated atazanavir, AZT protected against HIV-1 infection with an EC$_{50}$ value of 0.001 µM, Test compounds were not toxic to human monocytes at test concentrations up to 1 µM. A TI was calculated as described above using TC$_{50}$ values derived from cell toxicity data in response to test compounds in the absence of viral infection.

TABLE 7

Effect of Test Compounds on HIV-1 p24 Levels
Following Infection in Fresh Human Monocyte
(Monocyte/Macrophages)

| Compound | Monocyte/HIV-$1_{BaL}$ EC$_{50}$ (µM) | TC$_{50}$ (uM) | TI |
|---|---|---|---|
| AZT | 0.001 | >1.0 | >1000.0 |
| (repeated test) | 4.667 ± 2.168 | >200.0 |  |
| Saquinavir | 0.04 | >1.0 | >25.0 |
| mPEG5-NHCO-Saquinavir | 0.06 | >1.0 | >16.7 |
| mPEG7-NHCO-Saquinavir | 0.12 | >1.0 | >8.3 |
| Atazanavir | 1.877 ± 1.661 | 173 | 92.2 |
| (repeated tests) | <0.02 | 128.9 | >6445 |
| mono-mPEG1-Atazanavir | <0.02 | 159.1 | >7955 |
| mono-mPEG3-Atazanavir | 0.593 ± 0.364 | >200.0 | >337.3 |
|  | 0.0266 ± 0.0054 | 138.4 | 5203 |
| mono-mPEG5-Atazanavir | 0.0566 ± 0.0122 | 120.8 | 2134 |
| mono-mPEG6-Atazanavir | 0.0433 ± 0.0204 | 130.2 | 3007 |
| mono-mPEG7-Atazanavir | 0.1366 ± 0.0601 | 132.2 | 967.8 |
| Darunavir | <0.02 | >200.0 |  |
| mPEG5-N-Darunavir | 0.303 ± 0.366 | >200.0 |  |
| mPEG7-N-Darunavir | 0.577 ± 0.423 | >200.0 |  |
| mPEG3-O-Darunavir | 1.030 ± 1.453 | >200.0 |  |
| mPEG5-O-Darunavir | 0.263 ± 0.155 | >200.0 |  |

Example 2

In Vitro Biological Assays

Absorption

Physicochemical properties of PEG-saquinavir compounds were measured. A slight decrease in log P value was calculated for mPEG$_7$-NHCO-Saquinavir compared to saquinavir. Saquinavir had a C log P value of 3.49 and mPEG$_7$-NHCO-Saquinavir had a C log P value of 2.92.

Absorption properties of various compounds were measured using bi-directional permeability assays in Caco-2 cells. Results provided in Table 8. Conjugation resulted in a size-dependent reduction in the absorptive (apical (A)→basolateral (B)) permeability. The efflux ratio is calculated as the ratio of the $P_{app(B \to A)}/P_{app(A \to B)}$. Saquinavir produced efflux ratios of 24 and 6.93 in two different assays, consistent with saquinavir being a substrate for transporters. Conjugation increased the efflux ratio of saquinavir in a size-dependent manner compared to saquinavir in unconjugated form. At 7 PEG units, the largest PEG size tested, the efflux ratio was significantly increased compared to saquinavir. For Darunavir conjugates, an interesting difference was observed related to the site of conjugation. Thus PEGn-N-Darunavir conjugates displayed comparable A→B permeability and Efflux Ratios to the darunavir, with only the mPEG7-N-Darunavir exhibiting reduced permeability and a slightly increased efflux ratio. By contrast, mPEGn-O-Darunavir conjugates with PEG sizes as low as 3 and 5 units displayed lower permeability and increased efflux compared with darunavir. For atazanavir, conjugation of a single PEG moiety resulted in a PEG size-dependent decrease in permeability. Thus a progressive decrease in A→B permeability occurs with PEG sizes 1, 3 and 5. However, beyond PEG size 5, little further reduction in permeability is seen, and PEG-5,6 and 7-atazanavir conjugates display similar A→B permeability. Conjugation of two PEG moieties to atazanavir, however, further reduces the A→B permeability, although no difference was measured between two PEG-5 moieties and two PEG-7 moieties conjugated to a single atazanavir molecule. These data suggest that incorporation of small PEG moieties decreases the overall permeability of protease inhibitors, although for the mono-PEGylated conjugates this decrease represents up to a single order of magnitude change compared with the unconjugated parent. While the precise mechanism for decreased permeability is not known, it is possible that PEG conjugation to protease inhibitors increases their interaction with efflux transporters to decrease drug concentration in cells, thus limiting their transepithelial permeability.

TABLE 8

Permeability of PEG-PI Compounds Through Caco-2 Monolayers

| Compound | PEG units | A→B, ×10$^{-6}$ (cm/s) | Efflux ratio (B→A/A→B) |
|---|---|---|---|
| Saquinavir | 0 | 1.9 | 24 |
| N-Saquinavir | 0 | 5.1 | 6.93 |
| mPEG3-NHCO-Saquinavir | 3 | 4.21 | 5.73 |
| mPEG5-NHCO-Saquinavir | 5 | 1.66 | 13.99 |
| mPEG7-NHCO-Saquinavir | 7 | 0.255 | 52.94 |
| Darunavir | 0 | 2.55 | 17 |
| mPEG3-N-Darunavir | 3 | 2.52 | 13 |
| mPEG5-N-Darunavir | 5 | 1.07 | 21 |
| mPEG7-N-Darunavir | 7 | 0.32 | 34 |
| mPEG3-O-Darunavir | 3 | 0.51 | 32 |
| mPEG7-O-Darunavir | 7 | 0.19 | 33 |
| Atazanavir | 0 | 2.05 | 20 |
| (repeated test) | | 2.04 | 15 |
| di-mPEG5-Atazanavir | 2 × 5 | 0.06 | >10.8 |
| di-mPEG7-Atazanavir | 2 × 7 | 0.06 | >3.6 |
| mono-mPEG1-Atazanavir | 1 | 1.25 | 26 |
| mono-mPEG3-Atazanavir | 3 | 0.53 | 44 |
| mono-mPEG5-Atazanavir | 5 | 0.12 | 88 |
| mono-mPEG6-Atazanavir | 6 | 0.11 | 68 |
| mono-mPEG7-Atazanavir | 7 | 0.10 | 52 |

Metabolism
Interaction of Protease Inhibitors with CYP Enzymes

CYP450 inhibition assays identify and quantify the extent that a test compound inhibits key cytochrome P450 enzymes in liver microsomes. Inhibition studies are performed by incubating multiple concentrations of test compound (0.1-25 µM) with individual CYP isoform-specific probe substrates in buffer (0.1 M phosphate buffer, pH 7.4) containing human liver microsomes (0.1 mg/mL). The final concentration of organic solvent in all incubations is 0.25%. Samples are incubated at 37° C., and NADPH (1 mM final concentration) is added to initiate the reaction. Following five minutes incubation, the reactions are terminated by the addition of methanol containing internal standard then centrifuged at 2500 rpm for 20 minutes at 4° C. Aliquots of the supernatant are diluted with formic acid in deionized water (final formic acid concentration=0.1%) and analyzed for the presence of probe metabolite by liquid chromatography-tandem mass spectrometry or fluorescence, depending on the probe substrate used. Standard in vitro probe substrates for CYP enzymes include: CYP1A2, Phenacetin, 7-ethoxyresorufin; CYP2A6, Coumarin; CYP2B6, Bupropion; CYP2C8, Paclitaxel; CYP2C9, Diclofenac, Tolbutamide, S-Warfarin; CYP2C19, S-Mephenytoin, Omeprazole; CYP2D6, Bufurolol, Dextromethorphan; CYP2E1, Chlorzoxazone; CYP3A4, Midazolam, Testosterone.

Examination of the effect of protease inhibitors or the PEG-PI conjugates on prototypical CYP450 enzyme activity suggests that conjugation causes a change in the route of metabolic interaction. The affinity for CYP3A4 was decreased for the di-mPEGn-Atazanavir, mono-mPEGn-Atazanavir, mPEGn-O-Darunavir, and mPEGn-N-Darunavir conjugates when in competition with the prototypical CYP3A4 substrates, midazolam and testosterone. See Table 9A. In contrast, PEG-derivatives of tipranavir appear to have increased affinity for CYP3A4 during competition studies with midazolam, although no change in affinity was observed with testosterone. The affinity of mono-mPEGn-Atazanavir conjugates was decreased compared to atazanavir for other CYP enzymes important in metabolism of HIV protease inhibitors, including CYP2C9, CYP2D6, and CYP1A2 (see Tables 9B-D). It is important to note that these experiments are performed using microsomes in a cell-free system; they therefore reflect the metabolic path that would likely operate following penetration to the cell interior and do not include the component of cell permeation. Saquinavir and conjugates of saquinavir were not tested in these studies.

TABLE 9A

Inhibition of CYP3A4-mediated Prototypical Reactions

| Compound | CYP3A4 IC50 (µM) Testosterone | CYP3A4 IC50 (µM) Midazolam |
|---|---|---|
| Atazanavir (repeated tests) | 2.5 | 11.0 |
| | 1.43 | 1.10 |
| di-mPEG3-Atazanavir | 23.4 | >50.0 |
| di-mPEG5-Atazanavir | >50.0 | >50.0 |
| di-mPEG7-Atazanavir | >50.0 | >50.0 |
| mono-mPEG1-Atazanavir | 10.4 | 2.56 |
| mono-mPEG3-Atazanavir | 12.8 | 2.85 |
| mono-mPEG5-Atazanavir | >25 | 9.35 |
| mono-mPEG6-Atazanavir | >25 | 16.7 |
| mono-mPEG7-Atazanavir | >25 | 20.1 |
| Darunavir (repeated tests) | 0.9 | 0.9 |
| | 0.648 | 0.682 |
| mPEG3-N-Darunavir | 3.1 | 1.2 |
| mPEG5-N-Darunavir | 4.0 | 2.7 |
| mPEG7-N-Darunavir | 12.9 | 5.4 |
| mPEG3-O-Darunavir | 4.90 | 2.59 |
| mPEG5-O-Darunavir | >25 | >2.5 |
| Tipranavir | 2.1 | 10.7 |
| mPEG3-amide-Tipranavir | ~2.1 | 2.5 |
| mPEG5-amide-Tipranavir | 2.8 | 1.7 |
| mPEG7-amide-Tipranavir | ~4.0 | 2.6 |

TABLE 9B

Inhibition of CYP2C9-mediated Prototypical Reactions

| Compound | CYP2C9 IC50 (µM) Tolbutamide |
|---|---|
| Atazanavir | 10.3 |
| mono-mPEG1-Atazanavir | >25 |
| mono-mPEG3-Atazanavir | 24.6 |
| mono-mPEG5-Atazanavir | 23.7 |
| mono-mPEG6-Atazanavir | >25 |
| mono-mPEG7-Atazanavir | >25 |

TABLE 9C

Inhibition of CYP2D6-mediated Prototypical Reactions

| Compound | CYP2D6 IC50 (μM) Dextromethorphan |
|---|---|
| Atazanavir | 14.9 |
| mono-mPEG1-Atazanavir | 18.3 |
| mono-mPEG3-Atazanavir | >25 |
| mono-mPEG5-Atazanavir | 22.2 |
| mono-mPEG6-Atazanavir | >25 |
| mono-mPEG7-Atazanavir | >25 |

TABLE 9D

Inhibition of CYP1A2-mediated Prototypical Reactions

| Compound | CYP1A2 IC50 (μM) Phenacetin |
|---|---|
| Atazanavir | 20.6 |
| mono-mPEG1-Atazanavir | >25 |
| mono-mPEG3-Atazanavir | >25 |
| mono-mPEG5-Atazanavir | >25 |
| mono-mPEG6-Atazanavir | >25 |
| mono-mPEG7-Atazanavir | >25 |

Metabolic Stability of PEG-PI Conjugates in Human Microsomes

The human liver microsome-mediated biotransformation of PEG-PI compounds was determined by monitoring the loss of the substrate as a function of time. (Table 10). Test compounds (3 μM final concentration) were preincubated with pooled (male and female) human liver microsomes (0.5 mg/mL final protein concentration) in buffer (0.1M phosphate buffer, pH 7.4) at 37° C. Reactions were initiated by the addition of NADPH (1 mM final concentration), and allowed to continue for 0, 5, 15, 30, and 45 minutes. Reactions are terminated by the addition of 50 μL methanol containing internal standard then centrifuged at 2500 rpm for 20 minutes at 4° C. Sample supernatants are analyzed by liquid chromatography-tandem mass spectrometry.

TABLE 10

Metabolic Half-life in Human Liver Microsomes

| Compound | $CL_{int}$ (μL/min/mg protein) ± SEM | $t_{1/2}$ (min) |
|---|---|---|
| Atazanavir | 70.6 ± 3.14 | 19.6 |
| (repeated tests) | 101 ± 6.35 | 13.7 |
|  | 16.8 ± 3.27 | 82.7 |
| di-mPEG3-Atazanavir | 190 ± 18.3 | 7.31 |
| mono-mPEG1-Atazanavir | 181 ± 0.640 | 7.65 |
| mono-mPEG3-Atazanavir | 248 ± 31.7 | 5.58 |
| (repeated test) | 172 ± 1.39 | 8.04 |
| mono-mPEG5-Atazanavir | 108 ± 9.75 | 12.9 |
| mono-mPEG6-Atazanavir | 112 ± 1.10 | 12.3 |
| mono-mPEG7-Atazanavir | 71.0 ± 5.63 | 19.5 |
| Darunavir | 97.5 ± 4.59 | 14.2 |
| (repeated tests) | 108 ± 5.80 | 12.8 |
| mPEG3-N-Darunavir | 385 ± 0.718 | 3.60 |
| mPEG5-N-Darunavir | 440 ± 19.0 | 3.15 |
| mPEG7-N-Darunavir | 356 ± 7.74 | 3.89 |
| mPEG3-O-Darunavir | 77.4 ± 9.14 | 17.9 |
| mPEG-5-O-Darunavir | 198 ± 22.1 | 7.00 |
| mPEG7-O-Darunavir | 113 ± 8.87 | 12.2 |

TABLE 10-continued

Metabolic Half-life in Human Liver Microsomes

| Compound | $CL_{int}$ (μL/min/mg protein) ± SEM | $t_{1/2}$ (min) |
|---|---|---|
| Saquinavir |  | 1.4 |
| (repeated tests) |  | 1.1 |
|  | 706 ± 436 | 1.96 |
| mPEG3-NHCO-Saquinavir |  | 1.1 |
| (repeated tests) | 550 ± 248 | 2.52 |
| mPEG5-NHCO-Saquinavir |  | 1.1 |
| (repeated tests) | 644 ± 26.2 | 2.15 |
| mPEG7-NHCO-Saquinavir |  | 1.1 |
| (repeated tests) | 521 ± 133 | 2.66 |

Metabolic Stability of PEG-PI Compounds in Human Hepatocytes

Metabolism of PI conjugates was investigated by monitoring the levels of unmetabolized parent compound following incubation with cryopreserved human or monkey hepatocytes. The use of whole hepatocytes rather than microsomes requires that the drugs cross the cell membrane to interact with intracellularly-localized metabolic enzymes, and thus provides the most relevant in vitro system for understanding overall metabolic stability of these compounds. The results of these hepatocyte stability studies are provided in Tables 11A and 11B.

TABLE 11A

Metabolic Stability in Human Hepatocytes

| Compound | Test compound conc (uM) | $CL_{int}$ ± SEM (μL/min/$10^6$ cells) | $t_{1/2}$ (min) |
|---|---|---|---|
| Atazanavir | 3 | 5.15 ± 1.13* |  |
| (repeated tests) | 0.1 | 6.09 ± 0.62 | 227 |
|  | 0.1 | 4.09 ± 0.44 | 339 |
|  | 0.1 | 21.5 ± 0.00162 | 64.5 |
| di-mPEG3-Atazanavir | 3 | 3.46 ± 0.896* |  |
|  | 0.1 | −2.18 ± 0.57 | −637 |
| di-mPEG5-Atazanavir | 3 | 0.824 ± 0.950* |  |
| di-mPEG7-Atazanavir | 3 | −1.33 ± 1.09* |  |
| Mono-mPEG1-Atazanavir | 0.1 | 15.3 ± 0.00173 | 90.5 |
| Mono-mPEG3-Atazanavir | 0.1 | 0.878 ± 0.467 | 1580 |
| (repeated tests) | 0.1 | 15.8 ± 0.00119 | 88.0 |
| Mono-mPEG5-Atazanavir | 0.1 | 3.98 ± 0.000356 | 348 |
| Mono-mPEG6-Atazanavir | 0.1 | 0.778 ± 0.000211 | 1781 |
| Mono-mPEG7-Atazanavir | 0.1 | −2.27 ± 0.000376 | −610 |
| Darunavir | 3 | 7.60 ± 1.14* |  |
| (repeated tests) | 0.1 | 15.4 ± 1.39 | 89.8 |
|  | 0.1 | 18.8 ± 1.48 | 73.9 |
| mPEG3-N-Darunavir | 3 | 18.2 ± 1.47* |  |
| (repeated tests) | 0.1 | 48.0 ± 4.75 | 28.9 |
| mPEG5-N-Darunavir | 3 | 11.9 ± 1.40* |  |
| (repeated tests) | 0.1 | 3.94 ± 0.386 | 352 |
| mPEG7-N-Darunavir | 3 | 5.13 ± 0.611* |  |
| (repeated tests) | 0.1 | −1.58 ± 0.727 | −875 |
| mPEG3-O-Darunavir | 0.1 | −0.0957 ± 0.260 | −14500 |
| mPEG5-O-Darunavir | 0.1 | −2.58 ± 0.580 | −537 |
| mPEG7-O-Darunavir | 0.1 | −4.52 ± 0.393 | −307 |
| Tipranavir | 3 | 0.111 ± 0.643* |  |
| (repeated tests) | 0.1 | −0.149 | −9310 |
| mPEG3-amide-Tipranavir | 3 | 1.66 ± 1.24* |  |
| mPEG5-amide-Tipranavir | 3 | 3.62 ± 0.527* |  |
| mPEG7-amide-Tipranavir | 3 | 0.162 ± 0.343* |  |
| mPEG0-OCO—NH-Tipranavir | 0.1 | −0.514 ± 0.240 | −2700 |
| mPEG1-OCO—NH-Tipranavir | 0.1 | −0.908 ± 0.341 | −1530 |
| mPEG3-OCO—NH-Tipranavir | 0.1 | −0.226 ± 0.266 | −6120 |
| mPEG5-OCO—NH-Tipranavir | 0.1 | −1.54 ± 0.203 | −900 |

TABLE 11A-continued

Metabolic Stability in Human Hepatocytes

| Compound | Test compound conc (uM) | $CL_{int}$ ± SEM (µL/min/$10^6$ cells) | $t_{1/2}$ (min) |
|---|---|---|---|
| Saquinavir | 3 | 0.6** | |
| (repeated tests) | 0.1 | 52.1 ± 4.61 | 26.6 |
| mPEG3-NHCO-Saquinavir | 3 | 1.6** | |
| (repeated tests) | 0.1 | 12.8 ± 1.43 | 108 |
| mPEG5-NHCO-Saquinavir | 3 | 1.0** | |
| (repeated tests) | 0.1 | −2.18 ± 2.59 | −636 |
| mPEG7-NHCO-Saquinavir | 3 | 0.6** | |
| (repeated tests) | | | |

*Test compounds incubated with human hepatocytes up to one hour.
**Test compounds incubated with human hepatocytes up to two hours.

Test compounds (0.1 µM or 3 µM, as indicated) are incubated with cryopreserved human hepatocytes at a cell density of 0.5×$10^6$ viable cells/mL. The final DMSO concentration in the incubation is 0.25%. Duplicate samples (50 µL) are removed from the incubation mixture at various timepoints up to four hours (for 0.1 µM test compound concentration), or one or two hours (for 3 µM test compound concentration), and the reaction is quenched by the addition of methanol containing internal standard (100 µL). The samples are centrifuged (2500 rpm at 4° C. for 20 min), and the supernatants at each time point pooled for cassette analysis by LC-MS/MS.

Initial studies performed in human hepatocytes to evaluate stability of 3 M test compound throughout a one-hour incubation period resulted in little to no metabolism of the parent molecule. Optimized assay conditions utilized to observe metabolism of the non-PEG protease inhibitors comprise a four-hour incubation with human hepatocytes at a concentration of 0.1 µM test compound. The data in Table 11A and FIG. 3 demonstrate that PEG conjugation greatly reduced the rate of metabolism of PI molecules in human hepatocytes in comparison with non-PEG parent, with the exception of mPEG3-N-darunavir.

Metabolic Stability of PEG-PI Compounds in Monkey Hepatocytes

Similar to the approach used to measure metabolic stability in human hepatocytes, metabolic stability of PEG-PI compounds in cynomolgus monkey hepatocytes was also measured. The results of these hepatocyte stability studies are provided in Table 11B.

TABLE 11B

Metabolic Stability in Cynomolgus Monkey Hepatocytes

| Compound | Test compound conc. (uM) | $Cl_{int}$ ± SEM (µL/min/$10^6$ cells) | $t_{1/2}$ (min) |
|---|---|---|---|
| Atazanavir | 0.1 | 6.87 ± 1.28 | 202 |
| (repeated tests) | 0.1 | 46.3 ± 0.000868 | 29.9 |
| mono-mPEG1-atazanavir | 0.1 | 70.3 ± 0.00270 | 19.7 |
| mono-mPEG3-atazanavir | 0.1 | 13.9 ± 0.904 | 99.5 |
| (repeated tests) | 0.1 | 21.0 ± 0.00203 | 65.9 |
| mono-mPEG5-atazanavir | 0.1 | 13.8 ± 0.00163 | 100 |
| mono-mPEG6-atazanavir | 0.1 | 0.245 ± 0.000245 | 5660 |
| mono-mPEG7-atazanavir | 0.1 | −0.972 ± 0.0000868 | −1425 |
| Darunavir | 0.1 | 68.8 ± 1.97 | 20.1 |
| mPEG3-O-daruanvir | 0.1 | 8.53 ± 0.563 | 163 |
| mPEG5-O-daruanvir | 0.1 | −1.09 ± 0.427 | −1270 |
| mPEG5-N-daruanvir | 0.1 | 26.5 ± 0.942 | 52.3 |
| mPEG7-N-daruanvir | 0.1 | 0.286 ± 0.504 | 4850 |

Table 11B demonstrates that stability in monkey hepatocytes is somewhat different from that in human hepatoctyes, suggesting that cynomolgus monkeys would not be a representative species for examining the activity of these molecules in order to predict their disposition in humans.

Metabolic Stability of PEG-PI Compounds in Rat Hepatocytes

Similar to the approach used to measure metabolic stability in human hepatocytes, metabolic stability of PEG-PI compounds in Sprague-Dawley rat hepatocytes was also measured. The results of these hepatocyte stability studies are provided in Table 11C.

TABLE 11C

Metabolic Stability in Sprague-Dawley Rat Hepatocytes

| Compound | Test compound conc. (uM) | $Cl_{int}$ ± SEM (µL/min/$10^6$ cells) | $t_{1/2}$ (min) |
|---|---|---|---|
| Atazanavir | 0.1 | 101 ± 0.00802 | 13.7 |
| mono-mPEG1-atazanavir | 0.1 | 82.5 ± 0.0100 | 16.8 |
| mono-mPEG3-atazanavir | 0.1 | 11.9 ± 0.00223 | 117 |
| mono-mPEG5-atazanavir | 0.1 | −3.86 ± 0.000293 | −359 |
| mono-mPEG6-atazanavir | 0.1 | −5.81 ± 0.000684 | −239 |
| mono-mPEG7-atazanavir | 0.1 | −4.38 ± 0.000127 | −317 |
| Darunavir | 0.1 | 112 ± 0.0104 | 12.4 |
| mPEG3-O-daruanvir | 0.1 | 28.4 ± 0.00359 | 48.8 |
| mPEG5-O-daruanvir | 0.1 | 37.0 ± 0.00425 | 37.5 |

Table 11C demonstrates that stability in rat hepatocytes is somewhat different from that in human hepatoctyes. There appears to be a clear PEG-length dependent trend towards increased stability in rat hepatocytes.

Metabolic Stability of PEG-PI Compounds in Dog Hepatocytes

Similar to the approach used to measure metabolic stability in human hepatocytes, metabolic stability of PEG-PI compounds in beagle dog hepatocytes was also measured. The results of these hepatocyte stability studies are provided in Table 11D.

TABLE 11D

Metabolic Stability in Beagle Dog Hepatocytes

| Compound | Test compound conc. (uM) | $Cl_{int}$ ± SEM (µL/min/$10^6$ cells) | $t_{1/2}$ (min) |
|---|---|---|---|
| Atazanavir | 0.1 | 1.83 ± 0.000561 | 758 |
| mono-mPEG1-atazanavir | 0.1 | 31.1 ± 0.000512 | 44.5 |
| mono-mPEG3-atazanavir | 0.1 | 16.1 ± 0.000914 | 86.0 |
| mono-mPEG5-atazanavir | 0.1 | −0.528 ± 0.000119 | −2623 |
| mono-mPEG6-atazanavir | 0.1 | 0.209 ± 0.000143 | 6635 |
| mono-mPEG7-atazanavir | 0.1 | −1.90 ± 0.000482 | −730 |
| Darunavir | 0.1 | 4.61 ± 0.00139 | 301 |
| mPEG3-O-daruanvir | 0.1 | 15.5 ± 0.000361 | 89.5 |
| mPEG5-O-daruanvir | 0.1 | 4.93 ± 0.000253 | 281 |

Table 11D demonstrates that stability in dog hepatocytes is somewhat different from that in human hepatoctyes, suggesting that beagle dog would not be a representative species for examining the activity of these molecules in order to predict their metabolism in humans.

Metabolic Stability in Bactosomes™

Compounds were evaluated for their propensity to act as substrates of individual human cytochrome P450 enzymes using a bacterial membrane preparation co-expressing human NADPH-cytochrome P450 reductase with either human CYP3A4 or CYP2D6 (Bactosomes™ Cypex, Ltd., Dundee, UK). In vitro metabolism studies using Bactosomes™ expressing individual human CYP isoforms monitor the extent to which a test compound is metabolized by a single CYP450 enzyme and allow identification of the CYP isoforms that may be responsible for the metabolism of a test compound. Timecourse analyses of test molecules (5 µM) with CYP2D6- or CYP3A4-expressing Bactosomes™ (100 pmol/mL) are performed in buffer (0.1 M phosphate, pH 7.4) in a final reaction volume of 25 µL. Samples are preincubated at 37° C., and each reaction is initiated by the addition of NADPH (1 mM final concentration). The final concentration of organic solvent is maintained at 0.25%. Reactions are terminated by the addition of methanol (50 µL) containing internal standard at 0, 5, 15, 30, and 45 minutes. Samples are centrifuged at 2500 rpm for 20 minutes at 4° C. to precipitate protein, and the supernatant is analyzed by liquid chromatography-tandem mass spectrometry.

Figure 4A:
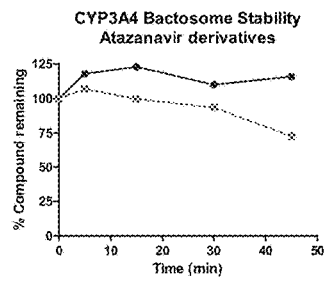
FIGS. 4A-4F are graphs showing the metabolic stability of PEG-protease inhibitors following incubation with CYP3A4- or CYP2D6-expressing Bactosomes™, as further described in Example 2 FIG. 4A (CYP3A4 Bactosome Stability, Atazanavir, di-mPEG3-atazanavir)
Figure 4B:
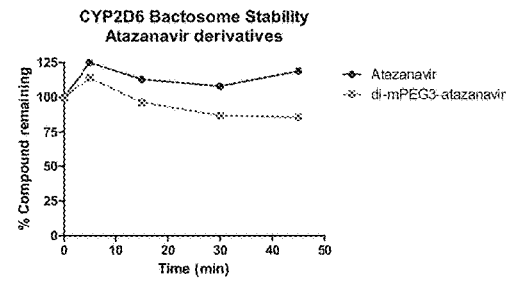
Figure 4C:
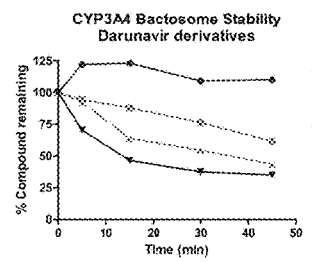
Figure 4D:
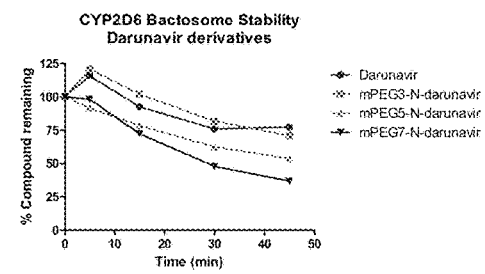
Figure 4E:
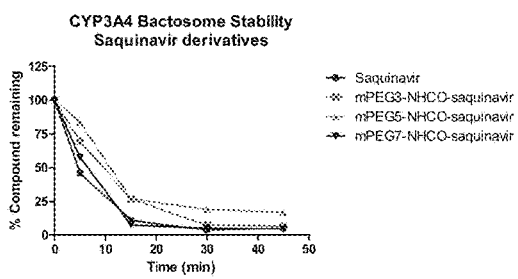
Figure 4F:
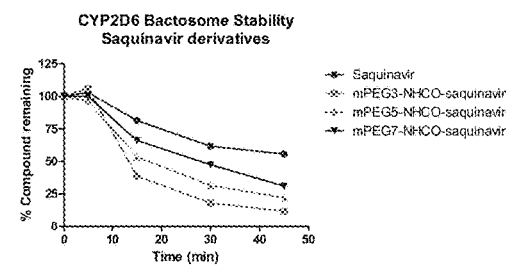

The di-mPEG3-Atazanavir derivative was metabolized to a similar level as ATZ in both CYP3A4- and CYP2D6-expressing Bactosomes™. Darunavir conjugates were metabolized more rapidly than non-PEG parent in both isoform-specific Bactosomes™, with a clear correlation between increased PEG length and decreased half-life. Saquinavir conjugates were also more rapidly metabolized in CYP2D6-expressing Bactosomes™ compared to saquinavir, however there was an inverse relationship between PEG length and improved metabolism. Parent and PEG-derivatives of saquinavir were rapidly metabolized by CYP3A4-Bactosomes™, and there was no differentiation in half-life. See Table 12 and FIGS. 4A-F.

TABLE 12

Metabolic Stability in Bactosomes ™

| Compound | 3A4 $t_{1/2}$ (min) ± SEM | 2D6 $t_{1/2}$ (min) ± SEM |
|---|---|---|
| Atazanavir | −525 ± 925 | −542 ± 1070 |
| di-mPEG3-Atazanavir | 95.8 ± 27.4 | 131 ± 48.5 |
| Darunavir | 2830 ± 31400 | 83.3 ± 27.0 |
| mPEG3-N-Darunavir | 66.6 ± 4.88 | 68.4 ± 18.9 |
| mPEG5-N-Darunavir | 37.4 ± 4.78 | 49.6 ± 2.63 |
| mPEG7-N-Darunavir | 13.9 ± 1.92 | 29.1 ± 1.95 |
| Saquinavir | 4.77 ± 0.102 | 47.1 ± 5.99 |
| mPEG3-NHCO-Saquinavir | 8.01 ± 0.188 | 11.1 ± 1.71 |
| mPEG5-NHCO-Saquinavir | 7.65 ± 1.60 | 19.4 ± 1.73 |
| mPEG7-NHCO-Saquinavir | 3.97 ± 0.509 | 25.6 ± 1.76 |

Metabolic Stability in Rat Microsomes

Metabolic stability of test compounds was studied in rat liver microsomes. Data presented in Table 13A. There was a clear PEG size-dependent increase in metabolic stability for conjugates of atazanavir and saquinavir.

TABLE 13A

Metabolism of Test Compounds in Rat Liver Microsomes

| Compound | PEG units | $t^{1/2}$ (min) |
|---|---|---|
| Atazanavir | 0 | 24.2 |
| Mono-mPEG3-Atazanavir | 3 | 26.8 |
| Mono-mPEG5-Atazanavir | 5 | 57.6 |
| Mono-mPEG6-Atazanavir | 6 | 104 |
| Saquinavir | 0 | 1.1 |
| mPEG3-NHCO-Saquinavir | 3 | 1.0 |
| mPEG5-NHCO-Saquinavir | 5 | 6.0 |
| mPEG7-NHCO-Saquinavir | 7 | 28.4 |

Metabolic Stability in Dog Microsomes

Metabolic stability of test compounds was studied in dog liver microsomes. PEGylated conjugates of atazanavir had faster clearance rates compared to atazanavir. Data presented in Table 13B.

TABLE 13B

Metabolism of Test Compounds in Dog Liver Microsomes

| Compound | PEG units | $Cl_{int}$ (µL/min/mg protein) | ±SEM $Cl_{int}$ | $t_{1/2}$ (min) |
|---|---|---|---|---|
| Atazanavir | 0 | 26.8 | ±1.54 | 51.8 |
| Mono-mPEG3-Atazanavir | 3 | 187 | ±7.94 | 7.42 |
| Mono-mPEG5-Atazanavir | 5 | 93.0 | ±2.38 | 14.9 |
| Mono-mPEG6-Atazanavir | 6 | 67.1 | ±1.64 | 20.7 |

Metabolic Stability in Monkey Microsomes

Metabolic stability of test compounds was studied in monkey liver microsomes. The mono-mPEGn-Atazanavir conjugates were cleared at significantly faster rates from monkey liver microsomes compared to atazanavir. Data presented in Table 13C.

TABLE 13C

Metabolism of Test Compounds in Monkey Liver Microsomes

| Compound | PEG units | $Cl_{int}$ (µL/min/mg protein) | ± SEM $Cl_{int}$ | $t^{1/2}$ (min) |
|---|---|---|---|---|
| Atazanavir | 0 | 42.9 | ±3.70 | 24.2 |
| Mono-mPEG3-Atazanavir | 3 | 249 | ±10.6 | 26.8 |
| Mono-mPEG5-Atazanavir | 5 | 175 | ±5.49 | 57.6 |
| Mono-mPEG6-Atazanavir | 6 | 238 | ±9.50 | 104 |

Metabolic Stability in Primary Rat Hepatocytes

The clearance of saquinavir conjugates was evaluated following incubation with primary rat hepatocytes. There was a clear trend in increased clearance in response to PEG-modification. This correlates with the rat liver microsome stability results, but does not exclude the possibility that PEG reduces the ability of saquinavir to cross cell membranes and interact with metabolizing enzymes.

TABLE 14

Metabolism of Test Compounds in Primary Rat Hepatocytes

| Compound | PEG units | $t^{1/2}$ (min) |
|---|---|---|
| Saquinavir | 0 | 32.5 |
| mPEG3-NHCO-Saquinavir | 3 | 125 |
| mPEG5-NHCO-Saquinavir | 5 | 150 |
| mPEG7-NHCO-Saquinavir | 7 | 2000 |

Protein Binding

PEGylated protease inhibitors were evaluated for their propensity to be bound by proteins in normal human plasma or in human liver microsome preparations using equilibrium dialysis analysis. For microsomal protein binding, test compound (final concentration=3 µM) was diluted into either buffer alone or buffer containing human liver microsomes. The protein-free and microsome-containing solutions were then added to either side of an equilibrium dialysis system and allowed to reach equilibrium at 37° C. The concentration of compound on both sides of the membrane at equilibrium was quantified by LC-MS/MS, and the fraction of compound that remains unbound ($F_u$) is calculated.

In assays to estimate binding of test compounds to plasma proteins, test compound solutions (5 μM) are prepared in buffer and species-specific plasma (final DMSO concentration 0.5%). The plasma-containing solution is added to one side of the membrane of an equilibrium dialysis system, and the plasma-free is added to the other side. Dialysis was allowed to reach equilibrium by incubation for two hours at 37° C. The concentration of compound on both sides of the membrane was measured using LC-MS/MS.

PEGylation of protease inhibitors demonstrated significantly reduced binding to proteins in human, rat, dog, mouse, and monkey plasma in comparison to non-PEGylated parent molecules, as demonstrated by increased free fraction ($F_u$). There was very little binding of both PEG-protease inhibitors and non-PEG protease inhibitors to proteins present in human liver microsomal preparations. Data presented in Tables 15A and 15B.

TABLE 15A

Binding of Test Compounds to Human Plasma Proteins and Human Liver Microsomal Proteins

| Compound | Plasma Protein Binding $F_u \pm SD$ | Microsomal Protein Binding $F_u \pm SD$ |
| --- | --- | --- |
| Atazanavir | 0.106 ± 0.0000525 | 0.846 ± 0.0308 |
| di-mPEG3-Atazanavir | 0.376 ± 0.00639 | highly unbound |
| di-mPEG5-Atazanavir | 0.537 ± 0.0412 | highly unbound |
| di-mPEG6-Atazanavir | 0.868 ± 0.0163 | highly unbound |
| di-mPEG7-Atazanavir | highly unbound | highly unbound |
| mono-m-PEG3-Atazanavir | 0.217 ± 0.000495 | 0.852 ± 0.0495 |
| Darunavir | 0.144 ± 0.0051 | 0.957 ± 0.0328 |
| mPEG3-N-Darunavir | 0.236 ± 0.0292 | 0.96 ± 0.0407 |
| mPEG5-N-Darunavir | 0.338 ± 0.0368 | 0.864 ± 0.011 |
| mPEG7-N-Darunavir | 0.364 ± 0.0298 | 0.973 ± 0.0139 |
| mPEG3-O-Darunavir | 0.274 ± 0.0194 | 0.936 ± 0.0109 |
| mPEG-5-O-Darunavir | 0.448 ± 0.0195 | 0.804 ± 0.253 |
| mPEG7-O-Darunavir | 0.314 ± 0.0116 | 0.84 ± 0.0131 |
| Tipranavir | 0.00866 ± 0.0013 | 0.302 ± 0.0853 |
| mPEG3-amide-Tipranavir | 0.014 ± 0.00166 | 0.73 ± 0.0153 |
| mPEG5-amide-Tipranavir | 0.0308 ± 0.00399 | highly unbound |
| mPEG7-amide-Tipranavir | 0.029 ± 0.00436 | highly unbound |
| mPEG0-OCO—NH-Tipranavir | 0.0105 ± 0.00848 | 0.887 ± 0.0749 |
| mPEG1-OCO—NH-Tipranavir | 0.0145 ± 0.000403 | 0.85 ± 0.184 |
| mPEG3-OCO—NH-Tipranavir | 0.0292 ± 0.000428 | 0.816 ± 0.0104 |
| mPEG5-OCO—NH-Tipranavir | 0.0304 ± 0.000274 | highly unbound |
| Saquinavir | 0.0353 ± 0.00151 | 0.493 ± 0.054 |
| mPEG3-NHCO-Saquinavir | 0.0748 ± 0.000319 | 0.941 ± 0.0604 |
| mPEG5-NHCO-Saquinavir | 0.144 ± 0.00327 | 0.954 |
| mPEG7-NHCO-Saquinavir | 0.115 ± 0.003 | highly unbound |

Anti-HIV-1 Activity in Monocyte-Derived Dendritic Cells:

Freshly separated human PBMCs from a single donor were suspended in DPBS at $4 \times 10^6$ cells/mL and incubated in a 75 cm² cell culture flask for 90 minutes at 37° C., 5% $CO_2$. Non-adherent cells were removed by washing with DPBS. Differentiation to dendritic cells was induced by 7 day incubation in RPMI 1640 medium supplemented with 10% fetal bovine serum, 2 mmol/L L-glutamine, 25 mM HEPES, 100 Units/mL penicllin, 10 μg/mL streptomycin, 50 ng/mL recombinant human granulocyte-macrophage-colony stimulating factor (GM-CSF), and 50 ng/mL recombinant human Interleukin (IL)-4 at 37° C., 5% $CO_2$. The cells were further incubated for two days in the same cytokine cocktail supplemented with 10 ng/mL lipopolysaccharide (LPS). The monocyte-derived dendritic cells were then suspended at $10 \times 10^6$ cells/mL in complete medium (RPMI 1640 medium supplemented with 10% fetal bovine serum, 2 mmol/L L-glutamine, 25 mM HEPES, 100 Units/mL penicllin, 10 μg/mL streptomycin) and infected for 2 h at 37 C, 5% $CO_2$ with HIV-$1_{Ba-L}$ at MOI=50-150 $TCID_{50}$. The infected cells were washed and resuspended at 1×106 cells/mL in complete medium, then 100 μL of the cell suspension was aliquoted to individual wells of a 96-well plate. Compound diluted in complete medium was added to cells. After seven days in culture, HIV-1 replication was quantified by measuring HIV-1 reverse transcriptase activity in cell-free supernatants using a standard radioactive tritiated thymidine triphosphate (TTP) polymerization incorporation assay. For each reaction, 1 μL of TTP (1 Ci/mL) was combined with 4 μL of $dH_2O$, 2.5 μL of poly rA and oligo dT (0.5 mg/mL and 1.7 Units/mL, respectively), and 2.5 μL reaction buffer (125 μL 1 mol/L EGTA, 125 μL $dH_2O$, 125 μL 20% Triton X-100, 50 μL 1 mol/L Tris, pH 7.4, 50 μL 1 mol/L DTT, 40 μL 1 mol/L $MgCl_2$), then 10 μL of the resulting mixture was combined with 15 L of virus-containing supernatant in a round-bottom microtiter plate and the plate incubated at 37° C. in a humidified incubator for 90 minutes. Following incubation, 10 μL of the reaction volume was spotted onto a DEAD filter mat, then washed 5×5 min with 5% sodium phosphate buffer, 2×1 minute in distilled water, 2×1 minute in 70% ethanol, then air dried. The filter mat was incubated with Opti-Fluor O scintillation fluid, and radioactivity quantified using a Wallac 1450 Microbeta Trilux liquid scintillation counter.

Test compound-induced cytotoxicity was evaluated by monitoring the reduction of the tetrazolium dye XTT in microtiter plates containing compound-treated cells in the absence of HIV-1 virus. XTT solution was prepared at 0.15

TABLE 15B

Binding of Test Compounds to Rat, Dog, Monkey, and Mouse Plasma Proteins

| Compound | Rat Plasma Protein Binding $F_u \pm SD$ | Dog Plasma Protein Binding $F_u \pm SD$ | Monkey Plasma Protein Binding $F_u \pm SD$ | Mouse Plasma Protein Binding $F_u \pm SD$ |
| --- | --- | --- | --- | --- |
| Atazanavir | 0.0790 ± 0.00684 | 0.139 ± 0.0167 | 0.201 ± 0.0183 | 0.0574 ± 0.00286 |
| mono-mPEG1-Atazanavir | 0.0793 ± 0.00541 | 0.208 ± 0.0317 | 0.246 ± 0.0239 | 0.0666 ± 0.00662 |
| mono-mPEG3-Atazanavir | 0.138 ± 0.0104 | 0.252 ± 0.0397 | 0.204 ± 0.196 | 0.159 ± 0.0161 |
| mono-mPEG5-Atazanavir | 0.307 ± 0.0493 | 0.695 ± 0.118 | 0.383 ± 0.359 | 0.217 ± 0.0103 |
| mono-mPEG6-Atazanavir | 0.451 ± 0.0385 | 0.497 ± 0.0386 | 0.598 ± 0.00839 | 0.159 ± 0.0167 |
| mono-mPEG7-Atazanavir | 0.255 ± 0.0778 | 0.306 ± 0.0478 | 0.570 ± 0.0439 | 0.174 ± 0.00791 | mg/mL in phosphate buffered saline. Phenazine methosulfate (PMS) solution was prepared at 0.15 mg/mL in phosphate buffered saline. A XTT/PMS stock solution was prepared immediately before use by combining 40 uL of PMS per mL of XTT solution. Fifty microliters of the XTT/PMS stock was added to each well of the microtiter plate, the plate was incubated for four hours at 37° C., and the amount of reduced XTT was measured as the absorbance at 450 nm. Cell viability is directly proportional to the amount of reduced XTT product formed.

Results obtained from this assay are provided in Table 16.

TABLE 16

Dendritic Cell Data

| Compound | $TC_{50}$ | $EC_{50}$ First | Second | Third | Mean $EC_{50}$ | SD |
|---|---|---|---|---|---|---|
| Atazanavir (μM) | >200 | 0.02 | 0.004 | 0.004 | 0.0093 | ±0.0072 |
|  | >1.0 | 0.00013 | 0.00058 | 0.00010 | 0.00027 | ±0.0002577 |
| mono-mPEG1-atazanavir (μM) | >1.0 | 0.00016 | 0.00025 | 0.00014 | 0.0001833 | ±0.0000572 |
| mono-mPEG3-atazanavir (μM) | >200 | 0.001 | 0.003 | 0.001 | 0.0017 | ±0.0011 |
| (repeated tests) | >1.0 | 0.00028 | 0.0143 | 0.00016 | 0.0049133 | ±0.007723 |
| mono-mPEG5-atazanavir (μM) | >1.0 | 0.00015 | 0.00342 | 0.00014 | 0.0012367 | ±0.0017947 |
| mono-mPEG6-atazanavir (μM) | >1.0 | 0.00016 | 0.00021 | 0.00023 | 0.0002 | ±0.0000286 |
| mono-mPEG7-atazanavir (μM) | >1.0 | 0.00013 | 0.0117 | 0.00025 | 0.0040267 | ±0.0010439 |
| Darunavir (μM) | >200 | 0.002 | 0.003 | 0.003 | 0.0027 | ±0.0004 |
| mPEG5-N-darunavir (μM) | >200 | 0.008 | 0.002 | 0.04 | 0.0167 | ±0.0199 |
| mPEG7-N-darunavir (μM) | >200 | 0.07 | 0.04 | 0.08 | 0.0633 | ±0.0205 |
| mPEG3-O-darunavir (μM) | >200 | 0.00017 | 0.00084 | 0.0167 | 0.0059 | ±0.0088 |
| mPEG5-O-darunavir (μM) | >200 | 0.06 | 0.06 | 0.05 | 0.0567 | ±0.0055 |
| AZT (nM) | >200 | 0.38 | 1.12 | 0.18 | 0.5600 | ±0.4853 |

As with the earlier cell-based activity assays, mono-mPEG3 atazanavir displayed greater potency than the unconjugated parent atazanavir. PEGylated conjugates of darunavir displayed reduced potency compared with the parent darunavir, but nevertheless retained significant anti-HIV effect in these cells.

CEM-SS Cytotoxicity

CEM-SS cells were passaged in T-75 flasks in RPMI 1640 medium supplemented with 10% fetal bovine serum, 2 mmol/L L-glutamine, 100 Units/mL penicillin and 100 μg/mL streptomycin. One day prior to assay initiation, cells were split 1:2 to assure exponential growth at the time of the assay. Cells were counted using a hemocytometer, and viability measured by Trypan Blue dye exclusion. Cell viability was greater than 95% in all assays. CEM-SS cells were resuspended at $5 \times 10^4$ cells/mL in medium, and 100 μL of the cell suspension was aliquoted to individual wells of a 96-well microtiter plate containing 100 μL 2× concentration test compound. Plates were incubated for 7 days at 37° C., 5% $CO_2$ until cytotoxicity evaluation.

Test compound-induced cytotoxicity was evaluated by monitoring the reduction of the tetrazolium dye XTT to a soluble formazan product in microtiter plates containing compound-treated cells in the absence of HIV-1 virus. XTT solution was prepared at 0.15 mg/mL in phosphate buffered saline. Phenazine methosulfate (PMS) solution was prepared at 0.15 mg/mL in phosphate buffered saline. A XTT/PMS stock solution was prepared immediately before use by combining 40 uL of PMS per mL of XTT solution. Fifty microliters of the XTT/PMS stock was added to each well of the microtiter plate, the plate was incubated for four hours at 37° C., and the amount of soluble formazan product was measured as the absorbance at 450 nm. Cell viability is directly proportional to the amount of soluble formazan product formed.

Cellular macromolecule synthesis was evaluated using tritiated precursor incorporation assays. CEM-SS cells (2.5× 103 cells/well) were cultured in the presence or absence of test compound for 7 days at 37 C, 5% CO2 in a 96-well microtiter plate. On day 6 of the incubation, 1 uCi of [methyl-3H]-thymidine for DNA synthesis, [5-3H]-uridine for RNA synthesis, or [3,4,5-3H]-leucine for protein synthesis was added to compound-treated cells, and the plate was further incubated for 16 hours. The cells were transferred to a glass fiber filtermat using an Inotech cell harvester. The filtermats were washed with distilled water then sealed in a bag with scintillation fluid. Incorporated radioactivity was measured using a Wallac scintillation counter.

Results obtained from this assay are provided in Table 17.

TABLE 17

Cytotoxicity in CEM-SS Cells

| Compound | XTT (CEM-SS) $TC_{50}$ (μM) | Thymidine incorporation (CEM-SS) $TC_{50}$ (μM) | Uridine incorporation (CEM-SS) $TC_{50}$ (μM) | Leucine Incorporation (CEM-SS) $TC_{50}$ (μM) |
|---|---|---|---|---|
| Atazanavir | 302.1 | 288.3 | 281.4 | 259.6 |
| mono-mPEG3-Atazanavir | >400 | 396.2 | 396.6 | >400 |
| Darunavir | 338.6 | 223.2 | >400 | 285.8 |
| mPEG3-O-Darunavir | >400 | 262.9 | >400 | >400 |
| mPEG5-O-Darunavir | >400 | 165.7 | >400 | >400 |

PBMC Cytotoxicity

Mononuclear cells were isolated from fresh human peripheral blood cells by Ficoll-Hypaque density gradient by centrifugation at 600 g for 30 minutes. Banded peripheral blood mononuclear cells (PBMCs) were aspirated from the resulting interface and washed with phosphate buffered saline by low speed centrifugation. Cell viability was evaluated by Trypan Blue dye exclusion. Cells were resuspended at 1×10$^6$ cells/mL in RPMI 1640 with 15% fetal bovine serum, 2 mmol/L L-glutamine, 2 µg/mL PHA-P, 100 Units/mL penicillin and 100 µg/mL streptomycin, and incubated at 37 C, 5% CO$_2$ for 48-72 hours. Following incubation, PBMCs were centrifuged and resuspended in growth medium (RPMI 1640 with 15% fetal bovine serum, 2 mmol/L L-glutamine, 3.6 ng/mL recombinant human interleukin (IL)-2, 100 Units/mL penicillin and 100 µg/mL streptomycin to induce proliferation. Assays were initiated with PBMCs that had been induced to proliferate for 72 hours. PHA-P stimulated PBMCs from three donors were pooled and resuspended at 1×10$^6$ cells/mL and 50 µL of the cell suspension were aliquoted to individual wells of a 96-well microtiter plate. Test compound was then added to cells to the desired final concentration. Plates were incubated at 37° C., 5% CO$_2$ for 7 days prior to cytotoxicity evaluation. XTT measurement for cytotoxicity.

Test compound-induced cytotoxicity was evaluated by monitoring the reduction of the tetrazolium dye XTT to a soluble formazan product in microtiter plates containing compound-treated cells in the absence of HIV-1 virus. XTT solution was prepared at 0.15 mg/mL in phosphate buffered saline. Phenazine methosulfate (PMS) solution was prepared at 0.15 mg/mL in phosphate buffered saline. A XTT/PMS stock solution was prepared immediately before use by combining 40 uL of PMS per mL of XTT solution. Fifty microliters of the XTT/PMS stock was added to each well of the microtiter plate, the plate was incubated for four hour at 37° C., and the amount of soluble formazan product was measured as the absorbance at 450 nm. Cell viability is directly proportional to the amount of soluble formazan product formed.

Cellular macromolecule synthesis was evaluated using tritiated precursor incorporation assays. PBMCs (5×104 cells/well) were cultured in the presence or absence of test compound for 7 days at 37 C, 5% CO2 in a 96-well microtiter plate. On day 6 of the incubation, 1 uCi of [methyl-3H]-thymidine for DNA synthesis, [5-3H]-uridine for RNA synthesis, or [3,4,5-3H]-leucine for protein synthesis was added to compound-treated cells, and the plate was further incubated for 16 hours. The cells were transferred to a glass fiber filtermat using an Inotech cell harvester. The filtermats were washed with distilled water then sealed in a bag with scintillation fluid. Incorporated radioactivity was measured using a Wallac scintillation counter.

Results obtained from this assay are provided in Table 18.

TABLE 18

| | Cytotoxicity in PMBC Cells | | | |
|---|---|---|---|---|
| Compound | XTT (PBMC) TC$_{50}$ (µM) | Thymidine Incorporation (PBMC) TC$_{50}$ (µM) | Uridine Incorporation (PBMC) TC$_{50}$ (µM) | Leucine Incorporation (PBMC) TC$_{50}$ (µM) |
| Atazanavir | 109.4 | 81.1 | 87.2 | 94.7 |
| mono-mPEG3-atazanavir | 338.9 | 36.6 | 27.7 | 82.0 |
| Darunavir | 328.4 | 184.3 | 189.3 | 258.3 |
| mPEG7-N-Darunavir | 381.3 | 67.5 | 57.7 | 72.9 |
| mPEG5-N-Darunavir | 223.5 | 41.3 | 73.2 | 98.5 |
| mPEG3-O-Darunavir | >400.0 | 109.6 | 139.4 | 218.9 |
| mPEG5-O-Darunavir | >400.0 | >400.0 | >400.0 | >400.0 |
| DMSO (%) | >2.0 | >2.0 | 0.06 | 0.19 |
| Triton X-100 (%) | 0.003 | 0.002 | 0.0009 | 0.0006 |

In CEM-SS cells, mono-mPEG3-atazanavir displayed comparable or lower toxicity than atazanavir, as evident from a higher TC$_{50}$ value, determined by four different assay methods. One of these methods (XTT) produced a similar result in PBMC cells, while the other assay methods in PBMCs displayed slightly lower TC$_{50}$ values. Together with the increased potency observed in multiple cell types, this suggests that mono-mPEG3-atazanavir could have not only greater potency, but also comparable or greater therapeutic index than atazanavir in antiviral use against HIV. mPEGn-O-Darunavir conjugates demonstrated a similar pattern to mono-mPEG3-atazanavir; thus in CEM-SS cells they displayed higher TC$_{50}$ values by all experimental readouts, with the exception of mPEG5-O-Darunavir in the Thymidine Incorporation assay. In PBMC cells, however, mPEG-O-Darunavir conjugates displayed an improved toxicity profile compared with darunavir using all experimental approaches tried, while mPEG-3-O-Darunavir had comparable TC50 values to darunavir. Thus, the mPEG-O-Darunavir conjugates are likely to have good activity and therapeutic indices in antiviral use against HIV. The mPEG-N-Darunavir conjugates, however, displayed somewhat lower TC$_{50}$ values in PBMC cells than darunavir.

Example 3

In Vitro Effect of PEGylated Protease Inhibitors on hERG Current (I$_{Kr}$) Expressed in Human Embryonic Kidney Cells The ion channel blocking profile of compounds NKT-10315, NKT-10404, NKT-10496, NKT-10497 were characterized on hERG current recorded from a human cell line stably expressing hERG (HEK-293). Currents were measured using the whole-cell variant of the patch clamp method. Glass pipettes were produced with tip openings of 1 to 2 m for K current recordings. Pipette tip resistance was approximately 1.0 to 2.0 MΩ when filled with K internal solutions (130 mM KCl, 5 mM MgCl$_2$, 10 mM HEPES, 5 mM EGTA, 5 mM ATP-Na$_2$, pH7.2). An Axopatch 1-B amplifier (Axon Instruments, Foster City, Calif.) was used for whole-cell voltage clamping. Voltage clamp pulses were controlled by pClamp software (ver 9.2, Axon Instruments).

After rupture of the cell membrane, current kinetics and amplitudes were allowed to stabilize as the cell was dialyzed with internal solution and paced at 0.1 Hz (−75 mV; 500 msec, +10 mV; 500 msec, −40 mV; typically 2-4 minutes). Currents were considered stable if the currents elicited by a series of voltage pulses given at 0.1 Hz were superimposed. Peak hERG current was measured as the maximum outward deflection of the tail current elicited upon return to −40 mV.

Data are presented in Table 19 as the percent reduction of current amplitude. This was measured as current reduction after a steady-state effect had been reached in the presence of drug relative to current amplitude before drug was introduced (control). Each cell served as its own control.

The ability of mono-mPEGn-Atazanavir conjugates to block hERG was somewhat decreased in comparison to atazanavir, as demonstrated by increased $IC_{50}$ values. This suggests that mono-mPEGn-Atazanavir conjugates have a low liability for hERG inhibition associated with adverse cardiac events.

TABLE 19

Block of hERG at 0.1 Hz by indicated compounds

| Compound | $IC_{50}$ (µM) | 10 µM Mean % inhibition ± SEM | 30 µM Mean % inhibition ± SEM | 100 µM Mean % inhibition ± SEM |
|---|---|---|---|---|
| Atazanavir | 63.9 | 15.6 ± 1.9 | 32.5 ± 3.7 | 60.5 ± 2.5 |
| mono-mPEG3-Atazanavir | 88.3 | 5.4 ± 0.6 | 23.7 ± 3.7 | 53.1 ± 2.6 |
| mono-mPEG5-Atazanavir | >100 | 11.2 ± 1.4 | 26.3 ± 2.9 | 43.8 ± 3.9 |
| mono-mPEG6-Atazanavir | >100 | 4.4 ± 0.4 | 12.7 ± 1.3 | 26.0 ± 1.0 |

What is claimed is:

1. A method comprising:
orally administering an HIV protease inhibitor conjugate to an individual infected with HIV, wherein the HIV protease inhibitor conjugate is mono-MPEG$_n$-darunavir having the structure selected from:

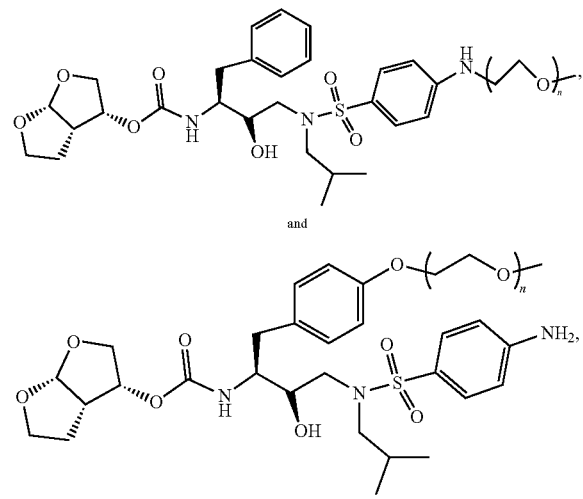

where n is selected from 3, 5, and 7, and
administering a second active agent in addition to the HIV protease inhibitor conjugate,
wherein the HIV protease inhibitor has an increased therapeutic index and/or increased potency relative to darunavir in unconjugated form, and
wherein said administering does not include co-administration of a CYP3A4 inhibitor.

2. The method of claim 1, wherein the dose of the conjugate administered is (i) different than the dose of the corresponding HIV protease inhibitor in unconjugated form, when compared on a molar basis, and (ii) retains at least about the same HIV protease inhibitor activity on a molar basis, when evaluated in a suitable model or individual.

3. The method of claim 2, wherein the dose of the conjugate administered is less than the dose of the corresponding HIV protease inhibitor in unconjugated form.

4. The method of claim 1, wherein the potent protease inhibitor is administered in a CYP3A4-competent biological system and said administering does not include co-administration of ritonavir.

5. A method comprising administering an HIV protease inhibitor conjugate as a protease inhibitor therapy to a biological system infected with HIV, wherein: (i) in a biological model in which the HIV protease inhibitor conjugate is periodically added in a given molar amount over time, and in the same biological model in which the same HIV protease inhibitor in unconjugated form is periodically added over time in the same given molar amount, the biological model in which the corresponding HIV protease inhibitor in unconjugated form is added is more likely to exhibit HIV protease resistance, and (ii) the HIV protease inhibitor conjugate retains at least substantially the same HIV protease inhibitor activity on a molar basis in a suitable model or patient, and (iii) the HIV protease inhibitor conjugate is mono-mPEG$_n$-darunavir having a structure selected from:

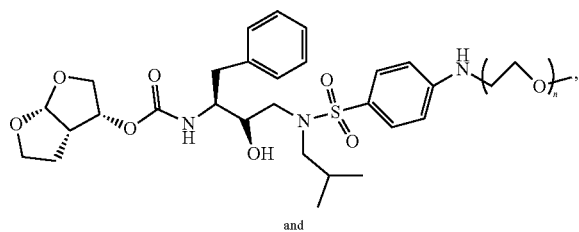

and

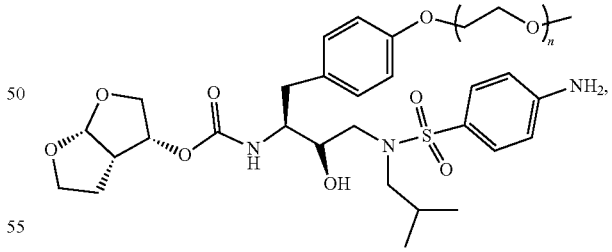

where n is selected from 3, 5, and 7, and administering a second active agent in addition to the HIV protease inhibitor conjugate.

6. The method of claim 5, wherein the potency of the protease inhibitor covalently attached to the water-soluble oligomer has a greater potency than the small drug molecule darunavir in unconjugated form.

7. In a method that comprises administering to an individual infected with HIV, darunavir in combination with a CYP3A4 inhibitor, the improvement comprising administering darunavir as a mono-mPEG$_n$-darunavir conjugate having a structure selected from:
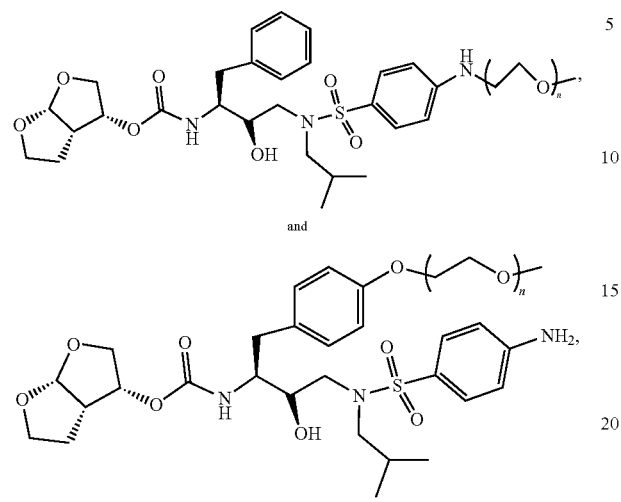
where n is selected from 3, 5, and 7, and further wherein said administering does not include co-administration of ritonavir.
* * * * *